(12) United States Patent
Chen

(10) Patent No.: US 12,121,722 B2
(45) Date of Patent: Oct. 22, 2024

(54) WIRELESS ELECTRICAL STIMULATION SYSTEM

(71) Applicant: Eric Chen, St. Louis, MO (US)

(72) Inventor: Eric Chen, St. Louis, MO (US)

(73) Assignee: HI-DOW IPHC, INC., Saint Louis, MO (US)

(*) Notice: Subject to any disclaimer, the term of this patent is extended or adjusted under 35 U.S.C. 154(b) by 207 days.

(21) Appl. No.: 16/703,603

(22) Filed: Dec. 4, 2019

(65) Prior Publication Data

US 2020/0139106 A1 May 7, 2020

Related U.S. Application Data

(63) Continuation-in-part of application No. 15/237,492, filed on Aug. 15, 2016, now Pat. No. 10,668,282, and a continuation-in-part of application No. 14/796,456, filed on Jul. 10, 2015, now Pat. No. 11,351,361, which is a continuation-in-part of application No. 14/328,433, filed on Jul. 10, 2014, now Pat. No. 9,415,217.

(30) Foreign Application Priority Data

Jan. 7, 2015 (CN) .......................... 201520007315.9

(51) Int. Cl.
*A61N 1/04* (2006.01)
*A61F 7/00* (2006.01)
*A61N 1/36* (2006.01)
*A61N 1/40* (2006.01)
*H05B 6/02* (2006.01)

(52) U.S. Cl.
CPC ............ *A61N 1/3603* (2017.08); *A61F 7/007* (2013.01); *A61N 1/0452* (2013.01); *A61N 1/0456* (2013.01); *A61N 1/0484* (2013.01); *A61N 1/403* (2013.01); *A61F 2007/0078* (2013.01); *A61F 2007/0094* (2013.01); *A61F 2007/0095* (2013.01); *A61N 1/36021* (2013.01); *H05B 6/02* (2013.01)

(58) Field of Classification Search
CPC .. A61N 1/3603; A61N 1/0452; A61N 1/0456; A61N 1/0484; A61N 1/36021; A61N 1/403; A61F 7/007; H05B 6/02
See application file for complete search history.

(56) References Cited

U.S. PATENT DOCUMENTS 8,579,953 B1* 11/2013 Dunbar .................. A61F 7/007
607/99
2002/0026226 A1* 2/2002 Ein .......................... A61F 7/007
607/108

(Continued)

*Primary Examiner* — Pamela M. Bays
(74) *Attorney, Agent, or Firm* — Arch & Lake LLP

(57) ABSTRACT

An apparatus, system and method are provided for a wireless electrical stimulation. The apparatus generally includes at least two electrical stimulation units. Each electrical stimulation unit includes electrodes connected to the unit. The apparatus also includes a receiver configured for receiving the one or more control signals from a remote controller for remotely, wirelessly controlling each of the electrical stimulation units to selectively apply a time-varying electric potential to the electrodes to provide an electrical stimulation to tissue in electrical contact with the electrodes. The apparatus generally includes a heating device.

5 Claims, 38 Drawing Sheets

(56) References Cited

U.S. PATENT DOCUMENTS

| | | | |
|---|---|---|---|
| 2004/0173220 A1* | 9/2004 | Harry | A61N 1/0492 128/892 |
| 2007/0173906 A1* | 7/2007 | Yamazaki | A61N 1/0452 607/60 |
| 2008/0288035 A1* | 11/2008 | Gill | A61N 2/02 607/108 |
| 2011/0130796 A1* | 6/2011 | Louise | A61F 7/007 607/3 |
| 2012/0109233 A1* | 5/2012 | Lee | A61F 7/007 607/3 |
| 2013/0085553 A1* | 4/2013 | Kang | A61F 7/08 607/100 |
| 2013/0158627 A1* | 6/2013 | Gozani | A61N 1/321 607/46 |
| 2014/0005759 A1* | 1/2014 | Fahey | A61N 1/0476 607/114 |
| 2014/0052199 A1* | 2/2014 | Mohn | A61N 1/0492 607/3 |
| 2014/0222102 A1* | 8/2014 | Lemus | A61N 1/36031 607/48 |
| 2014/0277220 A1* | 9/2014 | Brennan | A61N 1/0452 607/3 |
| 2017/0216592 A1* | 8/2017 | Dai | A61F 7/02 |

* cited by examiner

WIRELESS ELECTRICAL STIMULATION SYSTEM

CROSS-REFERENCE TO RELATED APPLICATIONS

This application is a continuation-in-part application which claims priority to U.S. patent application Ser. No. 14/796,456 filed Jul. 10, 2015 which claims priority and is a continuation-in-part of U.S. patent application Ser. No. 14/328,433 that is patented to U.S. Pat. No. 9,415,217, and U.S. patent application Ser. No. 15/237,492 filed on Aug. 15, 2016 which is a also continuation-in-part of U.S. patent application Ser. No. 14/328,433 that is patented to U.S. Pat. No. 9,415,217, and Chinese Patent Application No. 20150007315.9 filed Jan. 7, 2015. The entire disclosures of the above are incorporated herein by reference in their entireties.

FIELD

The present disclosure relates to wireless electrical stimulation systems, such as Transcutaneous Electrical Nerve Stimulation (TENS) and Electrical Muscle Stimulation (EMS) systems.

BACKGROUND

This section provides background information related to the present disclosure which is not necessarily prior art.

Electrical stimulation systems, such as Transcutaneous Electrical Nerve Stimulation (TENS) devices, Electrical Muscle Stimulation (EMS) devices, etc., can provide a stimulating waveform and electrical pulses to muscle groups and or nerve areas of the body, more particularly using electrode pads to deliver electrical pulses to particular areas of human bodies for pain relief.

Conventional electrical stimulation systems typically have a control unit hard-wired to a set of electrodes. Typical tethered control units are inconvenient to use, allow for only one treatment at a time, and provide little information to the user regarding the therapy being delivered. Wireless controls have been proposed, but for the most part they function similarly to the tethered control units.

Additionally, many conventional electrical stimulation systems typically have the electrodes connected directly to stimulation units, making it very difficult to treat parts of a subject's body spaced apart from the electrical stimulation unit and from each other.

SUMMARY

This section provides a general summary of the disclosure, and is not a comprehensive disclosure of its full scope or all of its features.

Examples of the present disclosure provide wireless electrical stimulation systems. According to an example, the system generally includes at least two electrical stimulation units. Each electrical stimulation unit includes electrodes connected to the unit. The system also includes a transmitter or a wireless controller for remotely, wirelessly controlling each of the electrical stimulation units to selectively apply a time-varying electric potential to the electrodes to provide an electrical stimulation to tissue in electrical contact with the electrodes. In some examples, a processor may be used to apply the time-varying electric potential to the electrodes to provide the electrical stimulation to tissue in electrical contact with the electrodes.

In some examples, the electrodes can be releasably connected to the electrical stimulation unit.

In some examples, the transmitter can include a unit selector for selecting one of the at least two electrical stimulation units to control with the transmitter.

In some examples, the transmitter can include a display for indicating which of the electrical stimulation units has been selected, and/or other information about the operation of the electrical stimulation units.

In some examples, at least some of the electrical stimulation units can have at least two operating modes, each of which applies a time-varying electrical potential to the electrodes in a different pattern. In these examples, the transmitter can have a mode selector for selecting one of the at least two operating modes. The transmitter can also include a display for indicating which of the operating modes has been selected.

In some examples, at least some of the electrical stimulation units are capable of operating at at least two intensities. In these examples, the transmitter can have an intensity selector for selecting one of the at least two intensities of operation. The intensity selector can additionally or alternatively include controls for increasing and decreasing intensity. The transmitter can also include a display for indicating the intensity that has been selected. In some examples, at least some of the electrical stimulation units are capable of operating for a selectable time period, and the transmitter has a time selector for selecting the time period of operation. The transmitter can also include a display for indicating the selected operating time period.

In some examples, the transmitter is a smart phone running an application.

In some examples, the electrical stimulation unit is carried on a flexible substrate adapted to be applied on a body surface. In some examples, the electrical stimulation unit is carried on an article of clothing (e.g., gloves, socks, slippers, etc.) that can directly contact particular areas of a body surface.

In some examples, the transmitter communicates with the electrical stimulation units via a radio frequency (RF) protocol.

In some examples, at least some of the electrical stimulation units turn off when communication with the transmitter is interrupted. In some examples, at least some of the electrical stimulation units turn off a predetermined time after communication with the transmitter is interrupted.

In some examples, at least some of the electrical stimulation units have a power switch and an indicator that indicates when the power is on. The electrical stimulation unit may further include an internal power supply, and an indicator for indicating the status of the internal power supply.

According to another aspect of the present disclosure, a method is provided for operating a plurality of wireless electrical stimulation units on a subject. The method generally includes remotely, wirelessly transmitting operating instructions to each of the plurality of wireless electrical stimulation units on separate channels using a single remote control.

In some examples, each of the wireless electrical stimulation units ceases operation within a predetermined period of time losing communication with the remote control.

In some examples, the operating instructions include at least one of intensity and duration.

In some examples, each of the wireless electrical stimulation units has at least two modes of operation, and wherein the operating instructions include a user selected one of the at least two modes of operation.

According to yet another aspect of the present disclosure, an electrical stimulation system is provided for providing electrical stimulation to a subject's body. The system includes a transmitter or a wireless controller, an electrical stimulation unit generating electrical stimulation signals in response to the wireless controller, at least two electrodes adapted to be disposed in electrical contact with the subject's body spaced apart from the electrical stimulation unit and from each other, and a cable electrically connecting the electrical stimulation unit to the at least two electrodes to apply electrical stimulation signals from the electrical stimulation unit to the electrodes positioned remotely from the electrical stimulation unit.

In some examples, the system includes a substrate adapted to be applied to a body surface with the at least two electrodes carried on the substrate.

In some examples, the substrate is an article of clothing to be worn by the subject, for example, a sock.

In some examples, the cable is a Y-cable having a stem and two branches, with a plug disposed on the end of the stem, and a connector disposed on each of the branches. The plug is configured to couple with a socket on the electrical stimulation unit and each of the connectors is configured for attaching and electrically connecting to an electrode.

In some example, the connectors are configured for permanently attaching to the electrodes.

In some examples, each of the connectors includes a metal fastener configured for removably attaching with corresponding structures configured on the at least two electrodes.

In some examples, the cable is an X-cable having first and second input branches, and first and second output branches. Connectors on each of the input branches are adapted to be connected to the electrical stimulation unit, and connectors on each of the output branches are adapted to connect to an electrode.

In some examples, the connectors on the input branches of the X-cable are configured for permanently attaching to the electrical stimulation unit.

In some examples, the connectors on the input branches of the X-cable include metal fasteners configured for removably coupling with corresponding structures of the electrical stimulation unit.

In some examples, the connectors on the output branches of the X-cable are configured for permanently attaching to an electrode.

In some examples, the connectors on the output branches of the X-cable include metal fasteners configured for removably coupling with corresponding structures on the electrodes.

Another aspect of the present disclosure provides an electrical stimulation apparatus for providing electrical stimulation to a surface of a human body. The electrical stimulation apparatus includes an electrical stimulation unit configured to generate at least one electrical waveform, and two electrodes operatively coupled to the electrical stimulation unit and configured to receive the at least one electrical waveform from the electrical stimulation unit. The two electrodes are insulated from each other, wherein the two electrodes are configured to be placed on or in proximity to the surface. The two electrodes are configured to deliver the at least one electrical waveform to muscle groups or nerve areas within the surface to which the electrodes are applied. The electrodes are configured to be applied externally to the surface. A remote controller is configured for controlling the electrical stimulation unit by generating and transmitting a first set of one or more control signals. The electrical stimulation unit includes a receiver configured for receiving the first set of one or more control signals from the remote controller. In response to receiving the first set of one or more control signals from the remote controller, the electrical stimulation unit generates the at least one electrical waveform and applies the at least one electrical waveform to the two electrodes. A heating device is operatively coupled to the receiver of the electrical simulation unit. The heating device comprises one or more heating pads configured for generating heat in response to a second set of one or more control signals received from the remote controller. The heating device is further configured for providing the generated heat to the surface proximate to where the electrodes are applied. The remote controller is further configured for controlling the heating device by generating and transmitting a second set of one or more control signals. The electrical stimulation unit includes a receiver configured for receiving the second set of one or more control signals from the remote controller. In response to receiving the second set of one or more control signals from the remote controller, the electrical stimulation unit activates the heating device to generate heat and to provide the generated heat to the surface proximate to where the electrodes are applied.

In some examples, the electrical stimulation apparatus is a therapy belt comprising at least an outer portion and an inner portion. The therapy belt includes a heating device and an electrical stimulation devices. The electrical stimulation device includes at least two therapy electrodes that are placed in an interlayer that is situated between the outer portion of the therapy belt and the inner portion of the therapy belt. The heating device includes at least two heating pads that are placed on or adjoining the inner portion of the therapy belt and configured for direct contact or thermal coupling with a subject's skin.

Another aspect of the present disclosure provides a wireless electrical stimulation system for providing electrical stimulation. The system comprises an electrical stimulation unit configured to generate at least one electrical waveform, and two electrodes operatively coupled to the electrical stimulation unit and configured to receive the at least one electrical waveform from the electrical stimulation unit. The two electrodes are insulated from each other. The two electrodes are configured to be placed on or in proximity to the surface, wherein the two electrodes are configured to deliver the at least one electrical waveform to muscle groups or nerve areas within the surface to which the electrodes are applied. The electrodes are configured to be applied externally to the surface. A wireless remote controller is configured for controlling the electrical stimulation unit by generating and wirelessly transmitting a first set of one or more control signals. The electrical stimulation unit includes a wireless receiver configured for receiving the first set of one or more control signals from the wireless remote controller. In response to receiving the first set of one or more control signals from the wireless remote controller, the electrical stimulation unit generates the at least one electrical waveform and applies the at least one electrical waveform to the two electrodes. A heating device is operatively coupled to the receiver of the electrical simulation unit. The heating device comprises one or more heating pads configured for generating heat in response to a second set of one or more control signals received from the wireless remote controller, and is further configured for providing the generated heat to the surface proximate to where the electrodes are applied. The wireless remote controller further configured for controlling the heating device by generating and transmitting a second set of one or more control signals. The electrical stimulation unit includes a wireless receiver configured for wirelessly receiving the second set of one or more control signals from the wireless remote controller. In response to receiving the second set of one or more control signals from the wireless remote controller, the electrical stimulation unit activates the heating device to generate heat and to provide the generated heat to the surface proximate to where the electrodes are applied.

Another aspect of the present disclosure provides a method of utilizing an electrical stimulation device on a surface of a human body. The method comprises providing an electrical stimulation unit configured to generate at least one electrical waveform. The method further comprises providing a structure that is substantially belt-shaped and is capable of being adjustably placed around a waist of a human body, the structure comprising a first electrode, a second electrode, and an insulating material that insulates the first electrode from the second electrode. The generated at least one electrical waveform is applied to the first and second electrodes using a remote controller configured for controlling the electrical stimulation unit by generating and transmitting a first set of one or more control signals, wherein the electrical stimulation unit includes a receiver configured for receiving the first set of one or more control signals from the remote controller. The generated at least one electrical waveform is applied by delivering the electrical waveform to a set of muscle groups or nerve areas within the surface that are electromagnetically coupled to the first and second electrodes. The first and second electrodes are configured to be applied externally to the surface. The one or more control signals cause the electrical stimulation unit to apply an electric potential across the first electrode and the second electrode to provide an electrical stimulation to the set of muscle groups or nerve areas within the surface. A heating device is provided proximate to the first and second electrodes. The heating device is operatively coupled to the receiver of the electrical stimulation unit. The receiver is configured for receiving a second set of one or more control signals from the remote controller, and the heating device is activated to generate heat in response to the second set of one or more control signals being received by the electrical stimulation unit from the remote controller. In some examples, the remote controller includes a power button and a power indicator. When the power button is first depressed, the controller turns ON and starts being supplied with power. When the power button is depressed again, the controller turns OFF and stops being supplied with power. Additionally, the power button may incorporate the power indicator, such that the power indicator is electrically coupled to a power supply in the controller and/or a processor to indicate whether or not the controller is provided with power. Illustratively, the power indicator may be an LED light, an incandescent lamp, a neon lamp, an audible alarm, a flashing light, or any of various combinations thereof.

In some examples, the controller includes its own internal power supply. The internal power supply can be a rechargeable battery, or other suitable energy storage device. The controller may further include a charging connector through which the internal power supply in the controller may be charged. The charging connector can be a USB charge connector.

In some examples, the therapy electrodes include Pulsed Electromagnetic Field (PEMF) radiating antennas.

In some examples, the controller may control the PEMF radiating antennas emitting a radio frequency signal. In some examples, the radio frequency signal may be in the range of 27-30 MHz. In some examples, the radio frequency signal may be emitted at 27.12 MHz.

In some examples, the position of each heating pad on the inner portion of the therapy belt is corresponding to the position of one therapy electrode on the outer portion of the therapy belt.

In some examples, the heating device may be a heating pad with a removable and changeable gel pack that provides rapid initial warming when exposed to the air.

In some examples, the controller further includes an electrical stimulation control button and an electrical stimulation indicator. When the electrical stimulation control button is first depressed for a short amount of time, the electrical stimulation apparatus turns ON and begins generating therapeutic electrical signals. When the electrical stimulation control button is depressed again for a short amount of time, the electrical stimulation apparatus turns OFF and stops generating the therapeutic electrical signals. Additionally, the electrical stimulation control button may incorporate the electrical stimulation indicator, such that the electrical stimulation indicator is electrically coupled to a portable power supply and/or a power supply in the controller and/or a processor, to indicate whether or not the electrical stimulation apparatus is working. Illustratively, the electrical stimulation indicator may be an LED light, an incandescent lamp, a neon lamp, an audible alarm, a flashing light, or any of various combinations thereof.

In some examples, the controller may further include a heating control button and a heating indicator. When the heating control button is first depressed for a short amount of time, the heating apparatus turns ON and begins heating. When the heating control button is depressed again for a short amount of time, the heating apparatus turns OFF and stops heating. Additionally, the heating control button may incorporate the heating indicator, such that the heating indicator is electrically coupled to a portable power supply and/or a power supply in the controller and/or a processor, to indicate whether or not the heating apparatus is working. Illustratively, the heating indicator may be an LED light, an incandescent lamp, a neon lamp, an audible alarm, a flashing light, or any of various combinations thereof.

In some examples, the controller may further include a connector through which power is provided to the controller. The therapy belt may further include a portable power source that is placed in a pocket attached on the outside of the therapy belt. Illustratively, a USB cable connects the portable power source and the connector, and provides power for the controller, and/or the heating apparatus, and/or the electrical stimulation apparatus from the portable power source.

In some examples, the therapy belt further includes a heating device that is placed in the interlayer of the therapy belt. The heating device may include at least two heaters. The heaters may comprise any of resistance wires, graphene sheets, heating films, or any of various combinations thereof.

Another aspect of the present disclosure provides an apparatus for applying electrical stimulation to a foot of a human body. The apparatus includes an electrical stimulation unit configured to generate at least one electrical waveform. Two electrodes, operatively coupled to the electrical stimulation unit, are configured to receive the at least one electrical waveform from the electrical stimulation unit. The two electrodes are insulated from each other. The two electrodes are provided in a structure that is wearable on the foot of the human body. The structure is configured for providing electrical stimulation to the foot. A remote controller is configured for controlling the electrical stimulation unit by generating and transmitting one or more control signals. The electrical stimulation unit includes a receiver configured for receiving the one or more control signals from the remote controller. In response to receiving the one or more control signals from the remote controller, the electrical stimulation unit generates the at least one electrical waveform and applies the at least one electrical waveform to the two electrodes. The two electrodes are configured to deliver the generated at least one electrical waveform to a set of muscle groups or nerve areas within the foot that are electromagnetically coupled to the two electrodes. At least one of the two electrodes is configured to be applied externally to the foot, underneath the foot, and in contact with the foot. The one or more control signals cause the electrical stimulation unit to apply an electric potential to the two electrodes to provide an electrical stimulation to the set of muscle groups or nerve areas within the foot that are electromagnetically coupled to the two electrodes.

According to another aspect of the present disclosure, a wireless electrical stimulation system provides electrical stimulation to a foot of a human body. The system comprises an electrical stimulation unit configured to generate at least one electrical waveform, and two electrodes operatively coupled to the electrical stimulation unit and configured to receive the at least one electrical waveform from the electrical stimulation unit. The two electrodes are insulated from each other, and the two electrodes are provided in a structure that is wearable on the foot. The structure is configured for providing electrical stimulation to the foot. A wireless remote controller is configured for wirelessly controlling the electrical stimulation unit by generating and transmitting one or more wireless control signals. The electrical stimulation unit includes a wireless receiver configured for wirelessly receiving the one or more control signals from the remote controller. In response to receiving the one or more wireless control signals from the remote controller, the electrical stimulation unit generates the at least one electrical waveform and applies the at least one electrical waveform to the two electrodes. The two electrodes are configured to deliver the generated at least one electrical waveform to a set of muscle groups or nerve areas within the foot that are electromagnetically coupled to the two electrodes. At least one of the two electrodes is configured to be applied externally to the foot, underneath the foot, and in contact with the foot; and the one or more control signals cause the electrical stimulation unit to apply an electric potential to the two electrodes to provide an electrical stimulation to the set of muscle groups or nerve areas within the foot that are electromagnetically coupled to the two electrodes.

According to another aspect of the present disclosure, a method of utilizing an electrical stimulation device on a foot of a human body is provided. The method comprises providing an electrical stimulation unit configured to generate at least one electrical waveform, and providing a structure that is wearable on the foot of the human body. The structure comprises a first electrode, a second electrode, and an insulating material that insulates the first electrode from the second electrode, the structure being configured for providing electrical stimulation to the foot. The structure is applied to the foot, and the generated at least one electrical waveform is applied to the first and second electrodes using a remote controller configured for controlling the electrical stimulation unit by generating and transmitting one or more control signals. The electrical stimulation unit includes a receiver configured for receiving the one or more control signals from the remote controller. The generated at least one electrical waveform is applied by delivering the electrical waveform to a set of muscle groups or nerve areas within the foot that are electromagnetically coupled to the first and second electrodes. The first and second electrodes are configured to be applied externally to the foot and underneath the foot. The first electrode or the second electrode is configured to be in contact with the foot; and the one or more control signals cause the electrical stimulation unit to apply an electric potential across the first electrode and the second electrode to provide an electrical stimulation to the set of muscle groups or nerve areas within the foot.

According to a further aspect of the present disclosure, the structure that is wearable on the foot of the human body comprises a pair of insoles. According to an illustrative example, the insole comprises a base, and a pair of stimulation electrodes placed on or in the base. The pair of stimulation electrodes are insulated from each other, wherein the pair of stimulation electrodes are configured for connecting with at least one stimulation unit that delivers electrical waveforms or pulses to foot tissue by the pair of stimulation electrodes.

In some examples, the insole further comprises a pair of male metal fasteners, each respective male metal fastener of the pair of metal fasteners being connected to a corresponding electrode of the pair of stimulation electrodes, wherein the pair of male metal fasteners are configured for attachment to a pair of female metal fasteners, and the pair of male metal fasteners are configured for connection with at least one stimulation unit using the pair of female metal fasteners.

In some examples, the insole may be used in a sandal.

Another aspect of the present disclosure provides a glove incorporating electrical stimulation. Thus, examples of the present disclosure can be used to conveniently control a glove to deliver electrical stimulation waveforms or pulses to particular areas of the human hand and/or body for performing nerve and/or muscle stimulation.

According to an illustrative example, the glove includes at least a layer comprising a conductive portion woven with an insulating portion. The glove further includes a male fastener that is electrically connected with the layer and configured for attachment to a female fastener that is located on an electrical stimulation unit.

In some examples, the electrical stimulation unit further includes a connector configured for connection to an electrode pad via an electrode wire.

In some examples, the electrode pad includes a flexible substrate so that it can be easily applied on a body surface.

In some examples, the electrode pad includes at least an electrode.

In some examples, the electrical stimulation unit is remotely and wirelessly controlled by a transmitter to deliver time-varying electrical waveforms or pulses to tissue via the electrodes connected with the electrical stimulation unit.

In some examples, the conductive portion of the layer of the glove is made of silver threads.

Further areas of applicability will become apparent from the description provided herein. The description and specific examples in this summary are intended for purposes of illustration only, and are not intended to limit the scope of the present disclosure.

DRAWINGS

The drawings described herein are for illustrative purposes only of selected examples and not all possible implementations, and are not intended to limit the scope of the present disclosure.

Corresponding reference numerals indicate corresponding parts throughout the several views of the drawings.

DETAILED DESCRIPTION

Example will now be described more fully with reference to the accompanying drawings.

Examples of the present disclosure provide wireless electrical stimulation systems and operating methods of a plurality of wireless electrical stimulation units on a subject. Thus examples of the present disclosure can be used to conveniently control electrode pads to deliver electrical pulses to particular areas of human bodies for nerve and/or muscle stimulation.

Figure 1:
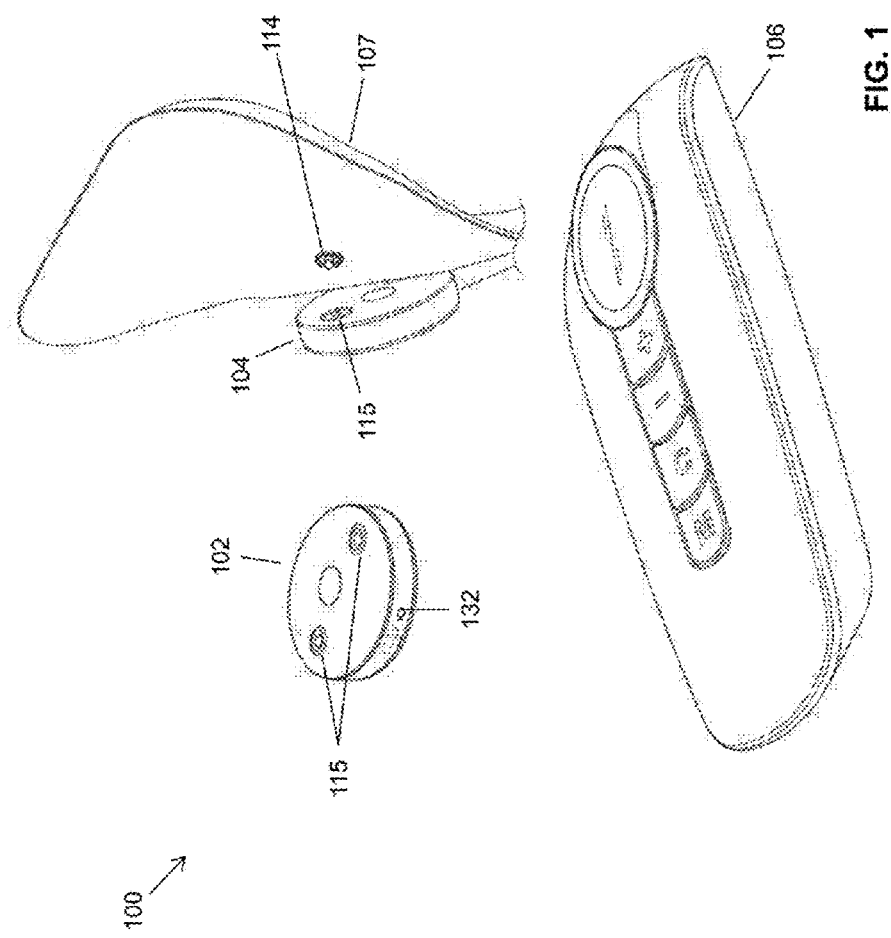
FIG. 1 is a view of an example of an electrical stimulation system according to the present disclosure.

As shown in FIG. 1, an example of a wireless electrical stimulation system 100 generally includes at least two electrical stimulation units 102, 104, and a transmitter 106.

The transmitter 106 remotely, wirelessly controls each of the electrical stimulation units 102, 104 to deliver electrical pulses to body tissue via electrode pads 107 connected to the electrical stimulation unit. The number of the electrical stimulation units can be as many as desired.

Figure 2:
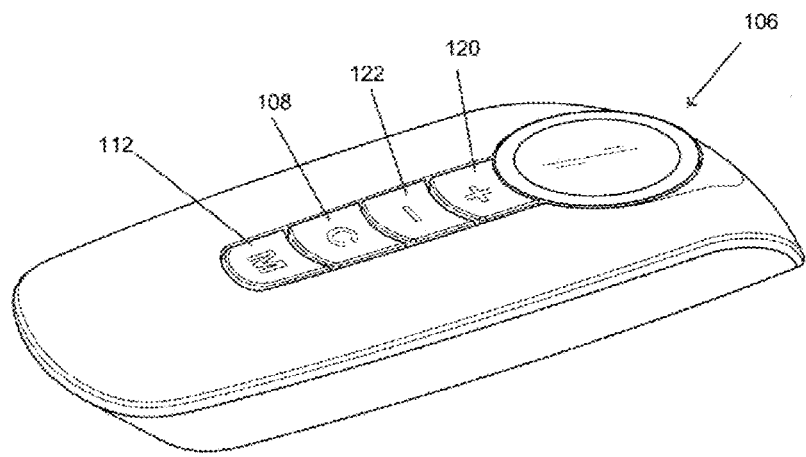
FIG. 2 is a perspective view of a transmitter of the wireless electrical stimulation system.
Figure 3:
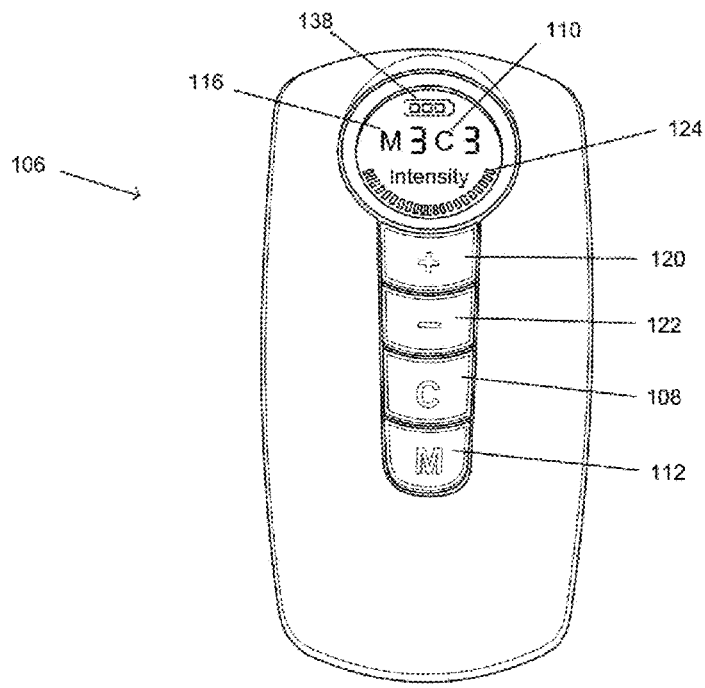
FIG. 3 is a front elevation view of the transmitter.
Figure 4:
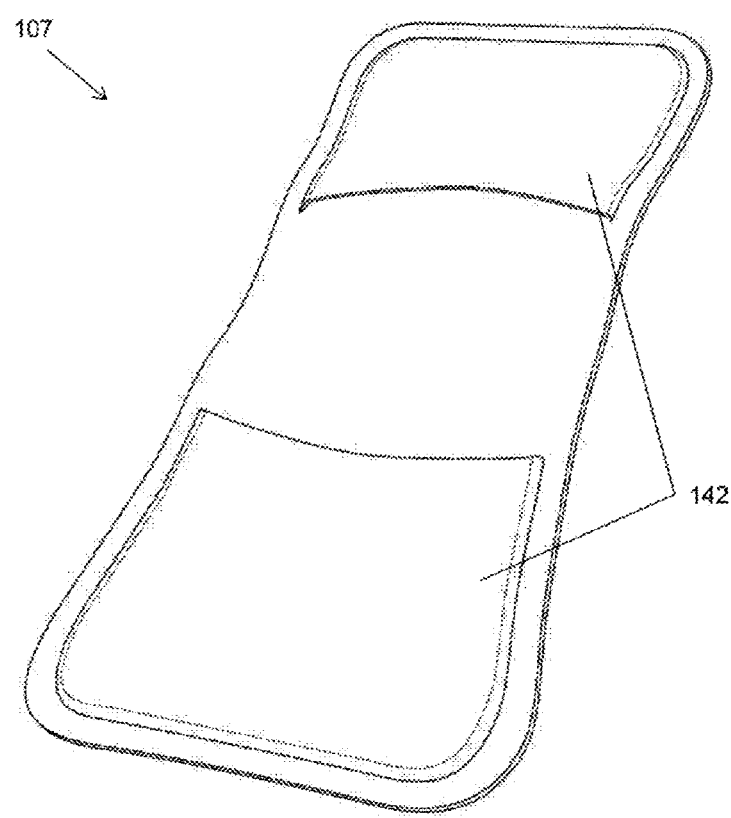
FIG. 4 is a front elevation view of the electrode substrate.
Figure 6:
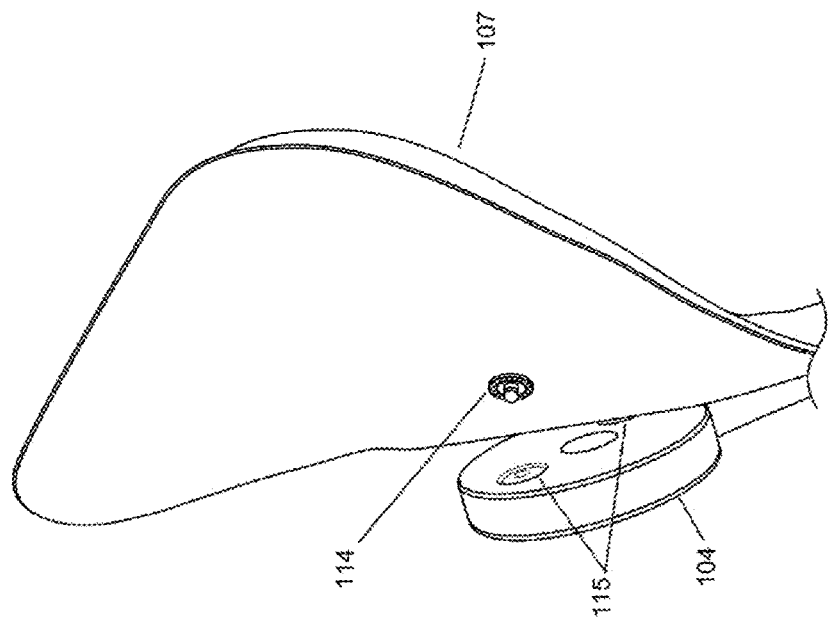
FIGS. 6 and 7 are perspective views illustrating attachment of the electrode substrate of FIGS. 4 and 5 to the electrical stimulation unit.
Figure 5:
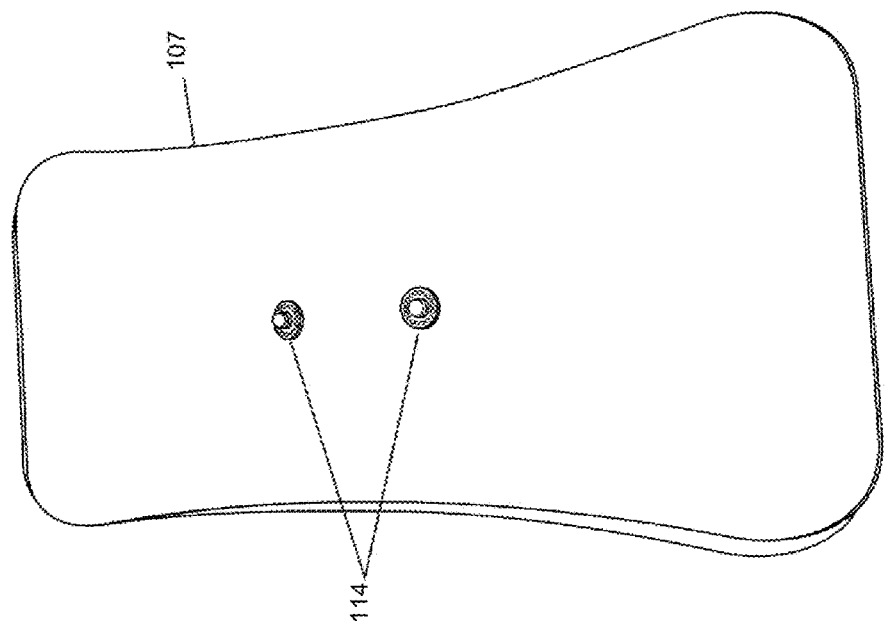
FIG. 5 is a back elevation view of the electrode substrate.

As shown in FIGS. 2-3, the transmitter 106 generally includes a unit selector 108 for selecting one electrical stimulation units to control with the transmitter 106. In this example the unit selector 108 is a single remote control button that allows the user to select a channel to remotely, wirelessly transmit operating instructions to one of the plurality of wireless electrical stimulation units. The unit selector button 108 preferably has a letter "C" on it, indicating to the user that the button 108 controls the channel selection. A user can select different wireless electrical stimulation unit by pressing the button 108, which can cycle through the available channels. In an alternative example, pressing the button 108 switches the transmitter to the channel mode, and the channel can be increased by pressing increase and decrease buttons 120 and 122, described in more detail below.

The transmitter 106 preferably also includes a display 110 for indicating which of the electrical stimulation units has been selected. When the user presses the button 108, the letter "C" on the display 110 flashes and indicates that the transmitter 106 is selecting a channel thereby selecting an electrical stimulation unit to control with. For example, as shown in FIG. 3, a number "3" displayed by the letter "C" on the display 110 indicates a communication connection to the number 3 electrical stimulation unit. Pressing the button 108 again changes the channel on which the transmitter 106 operates and thus changes the electrical stimulation unit the transmitter 106 controls, and changes the number displayed on the display 110.

As shown in FIGS. 4-7, an electrode pad 107 having a pair of electrodes 142 is provided. An electrode pad 107 is preferably releasably connected with each electrical stimulation unit to apply a time-varying electric potential to the electrodes 142 to provide an electrical stimulation to tissue in electrical contact with the electrodes. In some examples, a processor (not shown) may be provided in the electrical stimulation units to apply time-varying electric potential to the electrodes. The electrode pads 107 preferably have a pair of male metal snaps 114 for attaching to a pair of female metal snaps 115 on the electrical stimulation units. The metal snaps can alternatively be some other type or design of fastener for releasably engaging and electrically connecting the electrode pad 107 to the electrical stimulation unit.

The electrode pad 107 preferably includes a flexible substrate so that it can be easily applied on a body surface, for example, ankles, knees, wrists, shoulders, neck, etc. In other examples, the electrodes can also be carried on an article of clothing (e.g., accessories as gloves, socks, slippers, hats, etc.). The article of clothing preferably includes a pair of fasteners for removably attaching and electrically connecting with the electrical stimulation unit, forming an electronic circuit to apply an electrical stimulation to tissue in electrical contact with the electrodes.

At least some of the electrical stimulation units have at least two operating modes, each of which applies a time-varying electrical potential to the electrodes in a different pattern. FIGS. 8-19 illustrate some exemplary waveforms for four exemplary operating modes. Of course fewer or additional, or different operating modes having different pulse frequencies, pulse-widths, treatment pattern repetition cycles and amplitudes, can be provided. Below is a table summarizing the four example operating modes:

TABLE 1

Parameters for four Modes Testing With a Load of 1 KΩ

|  | Pulse frequency (Hz) | Pulse-width (µs) | Treatment pattern repetition cycle(s) | Amplitude (V) |
|---|---|---|---|---|
| Mode 1 (FIGS. 8-9) | 52 | 100 | 4.5 | 60 |
| Mode 2 (FIGS. 10-12) | 11 | 100 | 4.5 | 75 |
| Mode 3 (FIGS. 13-14) | 1.2 | 100 | continuous | 75 |
| Mode 4 (FIGS. 15-19) |  |  |  |  |
| $1^{st}$ Stage: | 1.9-8.3 | 100 |  | 75 |
| $2^{nd}$ Stage: | 60 | 100 | 90 (total) | 58 |
| $3^{rd}$ Stage: | 1-11.5 | 100 |  | 75 |
| $4^{th}$ Stage: | 53.5 | 100 |  | 60 |

The transmitter 106 preferably further includes a mode selector for selecting an operating mode for each electrical stimulation unit. The mode selector is preferably a single remote control button 112 that can be used to remotely, wirelessly transmit operating instructions of a user selected operating mode to the selected one of the plurality of wireless electrical stimulation units. The unit selector button 108 preferably has a letter "M" on it, indicating to the user that the button controls the mode. A user can select different operating modes by pressing the button 112, which cycles through the available modes. A user can select different wireless electrical stimulation unit by pressing the button 108, which can cycle through the available channels. In an alternative example, pressing the button 112 switches the transmitter to the operating mode, and the mode can be changed by pressing increase and decrease buttons 120 and 122, described in more detail below.

The transmitter 106 can further include a display 116 for indicating which of the operating modes has been selected. When the user presses the mode selector 112, the letter "M" on the display 116 flashes and indicates that the transmitter 106 is selecting an operating mode for a selected electrical stimulation unit. For example shown in FIG. 3, a number "3" displayed adjacent the letter "M" on the display 110 indicates an operating mode 3 is selected for the selected electrical stimulation unit. Pressing the mode selector 112 can change the number displayed and thereby change the operating modes of the selected electrical stimulation unit to be controlled with. Alternatively, the mode selector button 112 can be pressed to enter the mode selection mode, and then the increase and decrease buttons 120 and 122 can be operated to select the desired mode.

Figure 7:
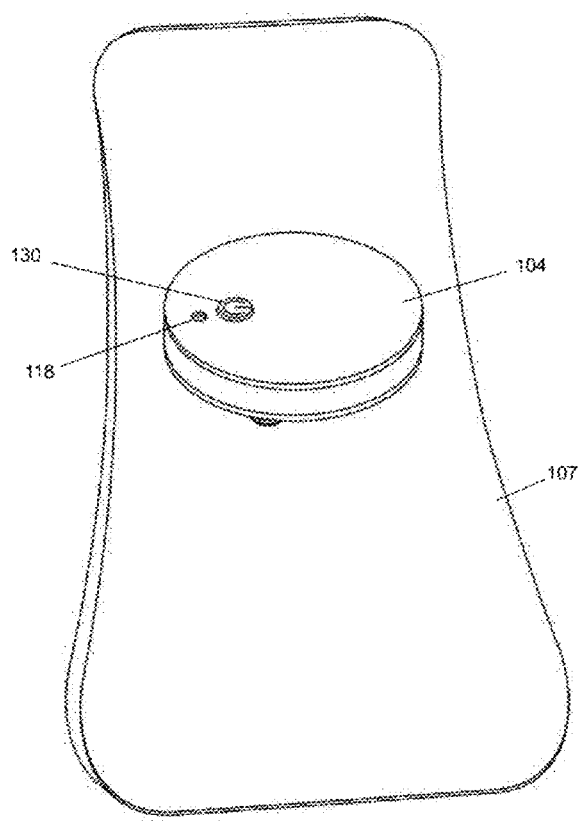
Figure 8:
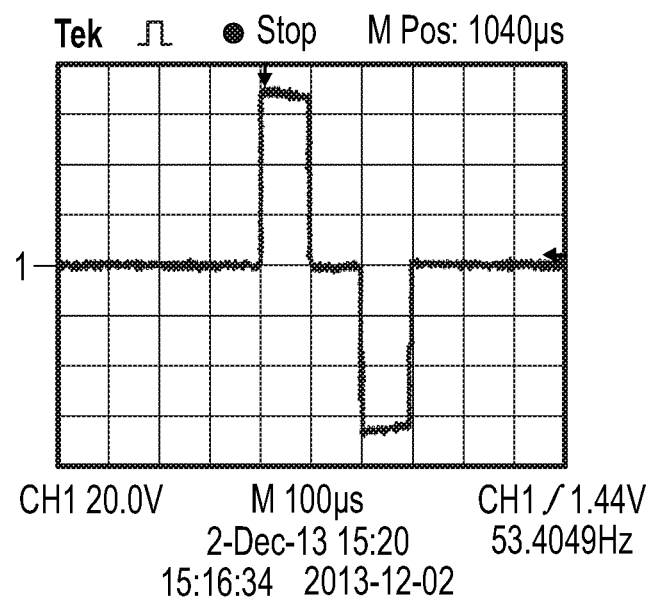
FIGS. 8 and 9 illustrate exemplary waveforms for an operating mode 1.
Figure 9:
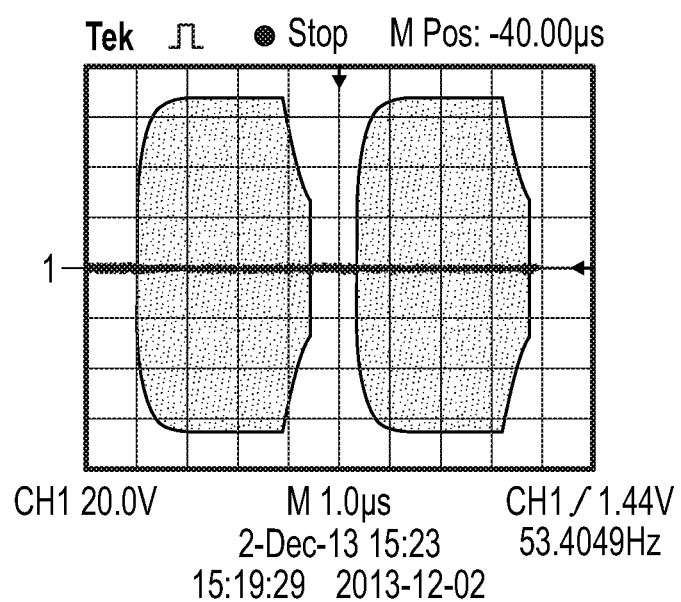
Figure 10:
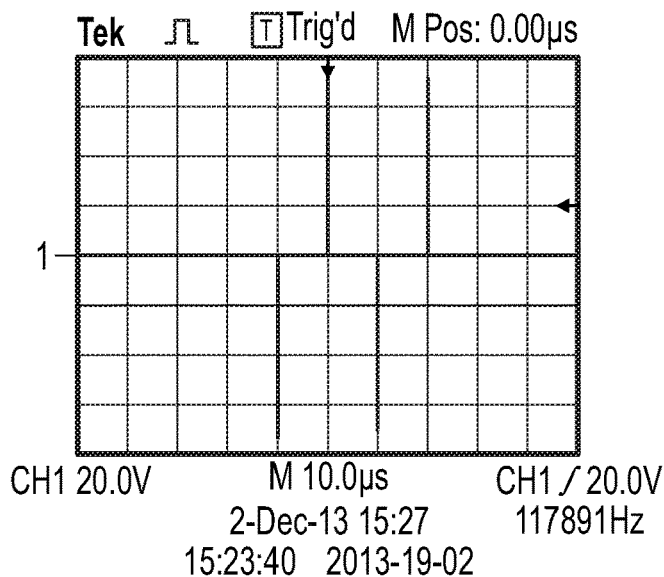
FIGS. 10-12 illustrate exemplary waveforms for an operating mode 2.
Figure 11:
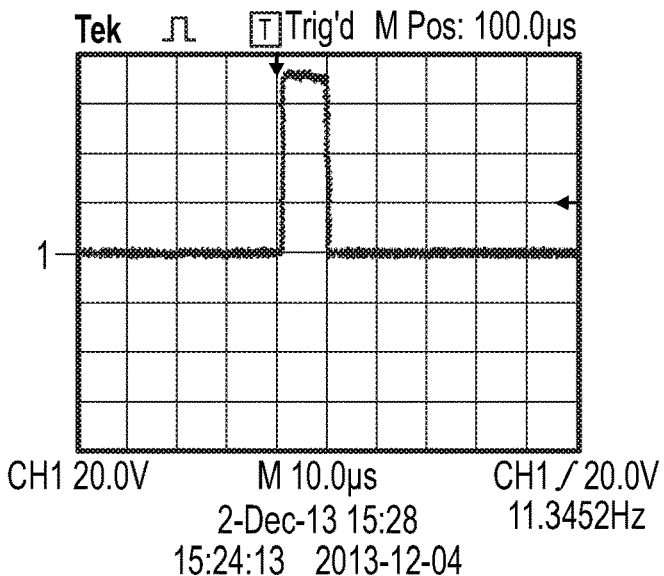
Figure 12:
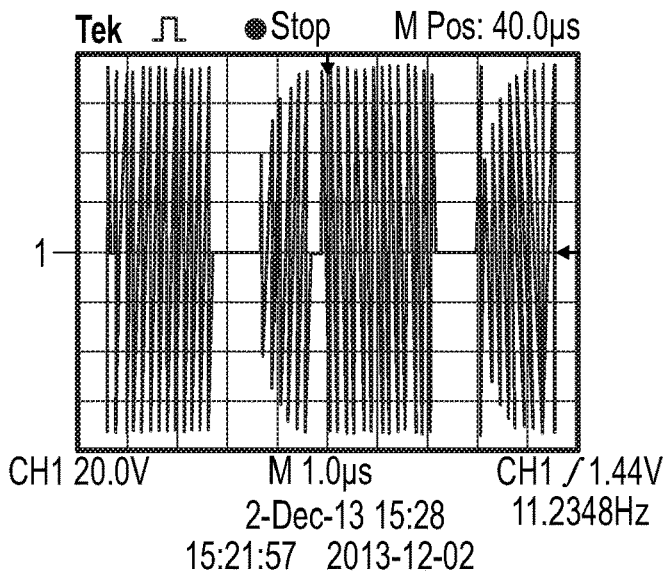
Figure 13:
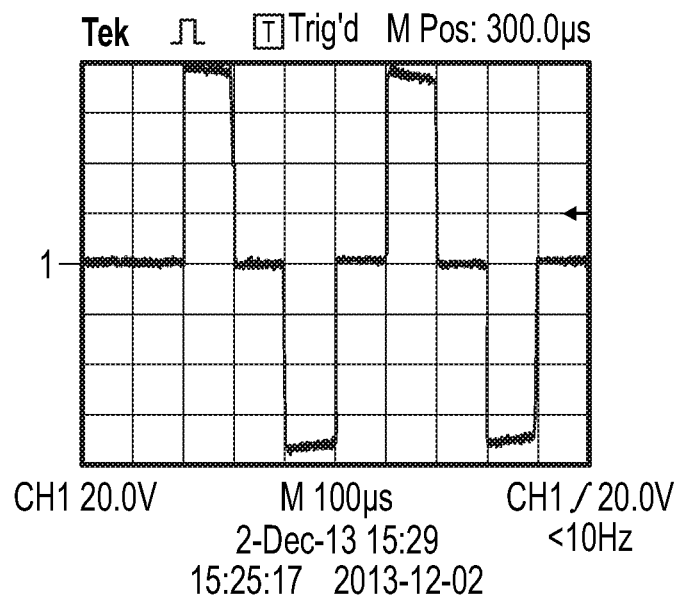
FIGS. 13 and 14 illustrate exemplary waveforms for an operating mode 3.
Figure 14:
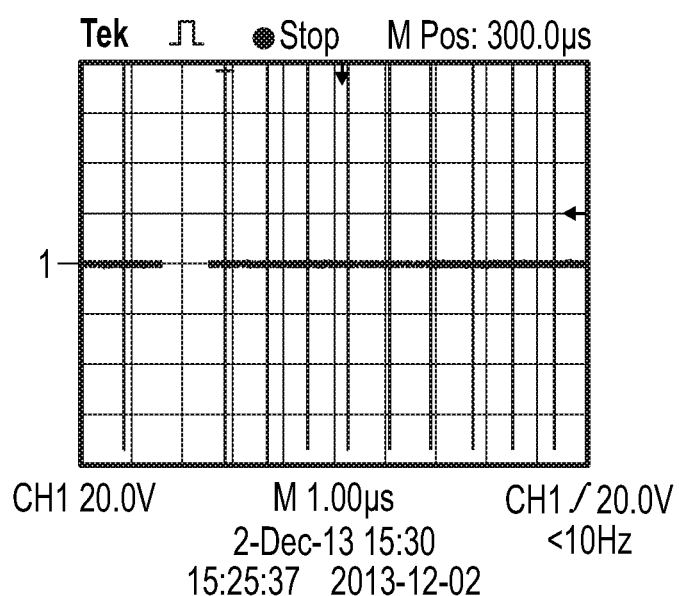
Figure 15:
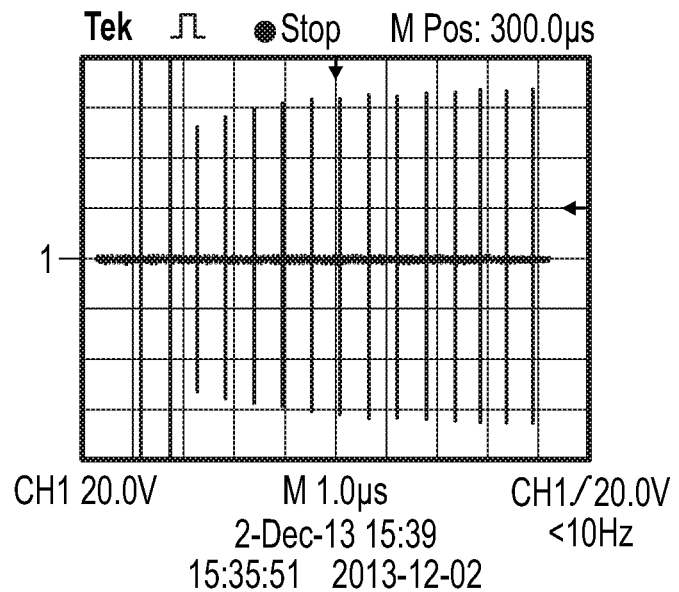
FIGS. 15-19 illustrate exemplary waveforms for an operating mode 4.
Figure 16:
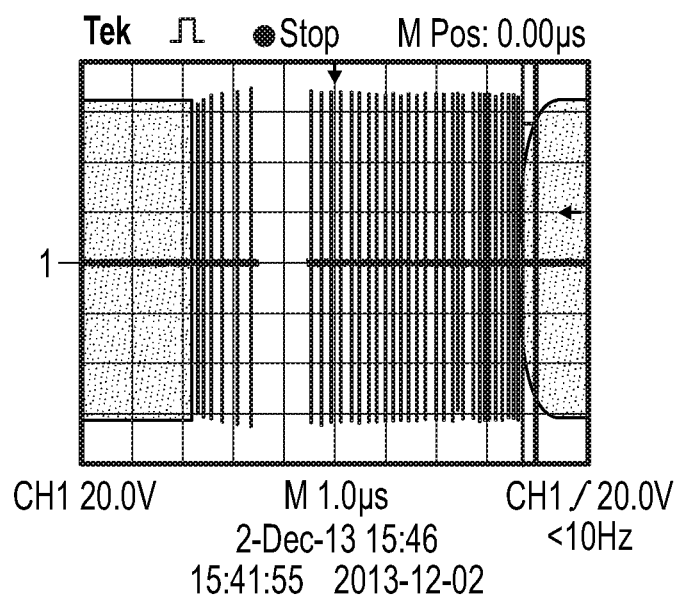
Figure 17:
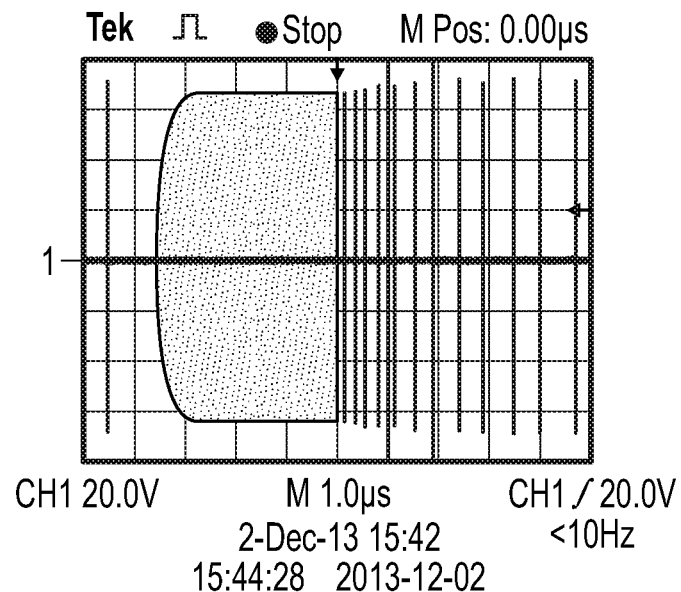
Figure 18:
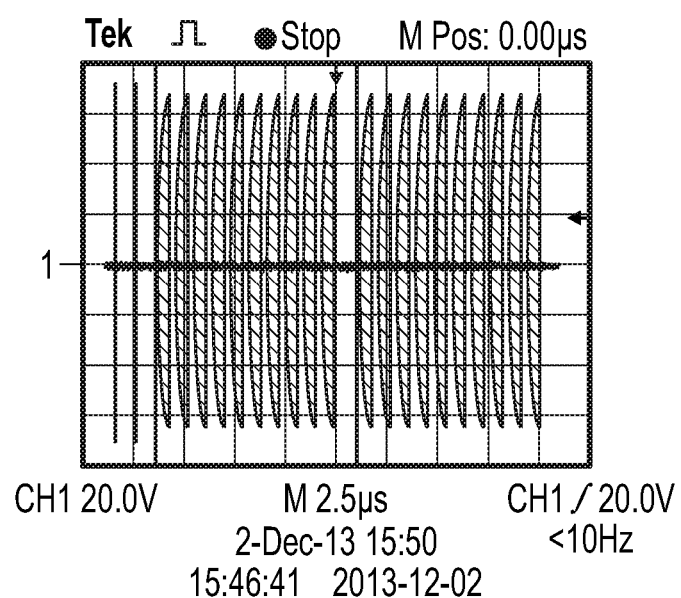
Figure 19:
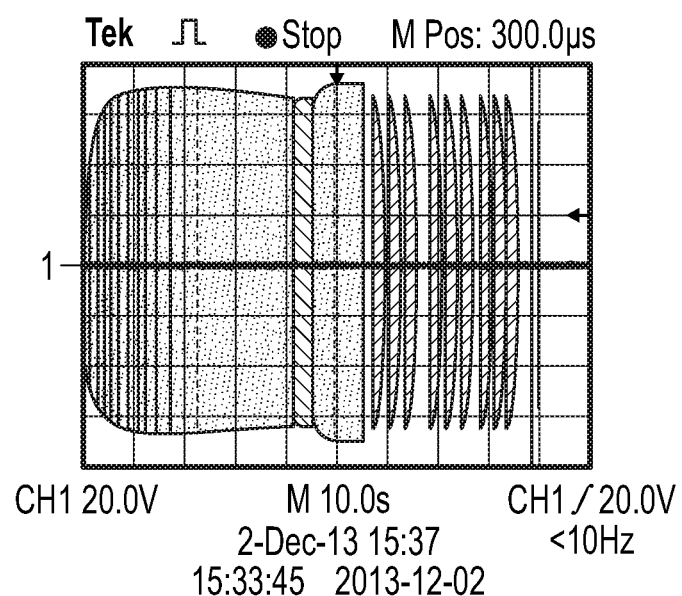

As shown in FIG. 7, at least some of the electrical stimulation units preferably include a working status indicator 118. The working status indicator 118 is "on" when the electrical stimulation unit is powered on. When an electrical stimulation unit 102, 104 is selected to be controlled, the working status indicator 118 of this selected electrical stimulation unit 102, 104 flashes or blinks in response to the operating instructions transmitted from the transmitter 106.

At least some of the electrical stimulation units are capable of operating at at least two intensities. As shown in FIG. 3, the transmitter 106 includes an intensity selector for selecting different intensities. In the example shown in FIGS. 1-3, the intensity selector consists of an increase button 120 and a decrease button 122 for increasing and decreasing the operating intensity for the electrical stimulation unit to be controlled with. The increase button 120 and decrease button 122 are remote control buttons that remotely, wirelessly transmits operating instructions of a user selected intensity to a selected one of the plurality of wireless electrical stimulation units. The increase and decrease buttons 120 and 122 preferably have "+" and "−" signs respectively, to indicate their function to the user. A user can adjust the operating intensity by pressing the buttons 120 and 122 to a level the user desires.

As shown in FIG. 3, the transmitter 106 can further include a display 124 for indicating the level of the operating intensity that has been selected. When the user presses either the increase button 120 or the decrease button 122, the word "intensity" on the display 124 flashes and indicates that the transmitter 106 is selecting an operating intensity for the selected electrical stimulation unit. The display 124 preferably shows a number of bars along the circumferential edge of the display indicating the level of the intensity.

Figure 20:
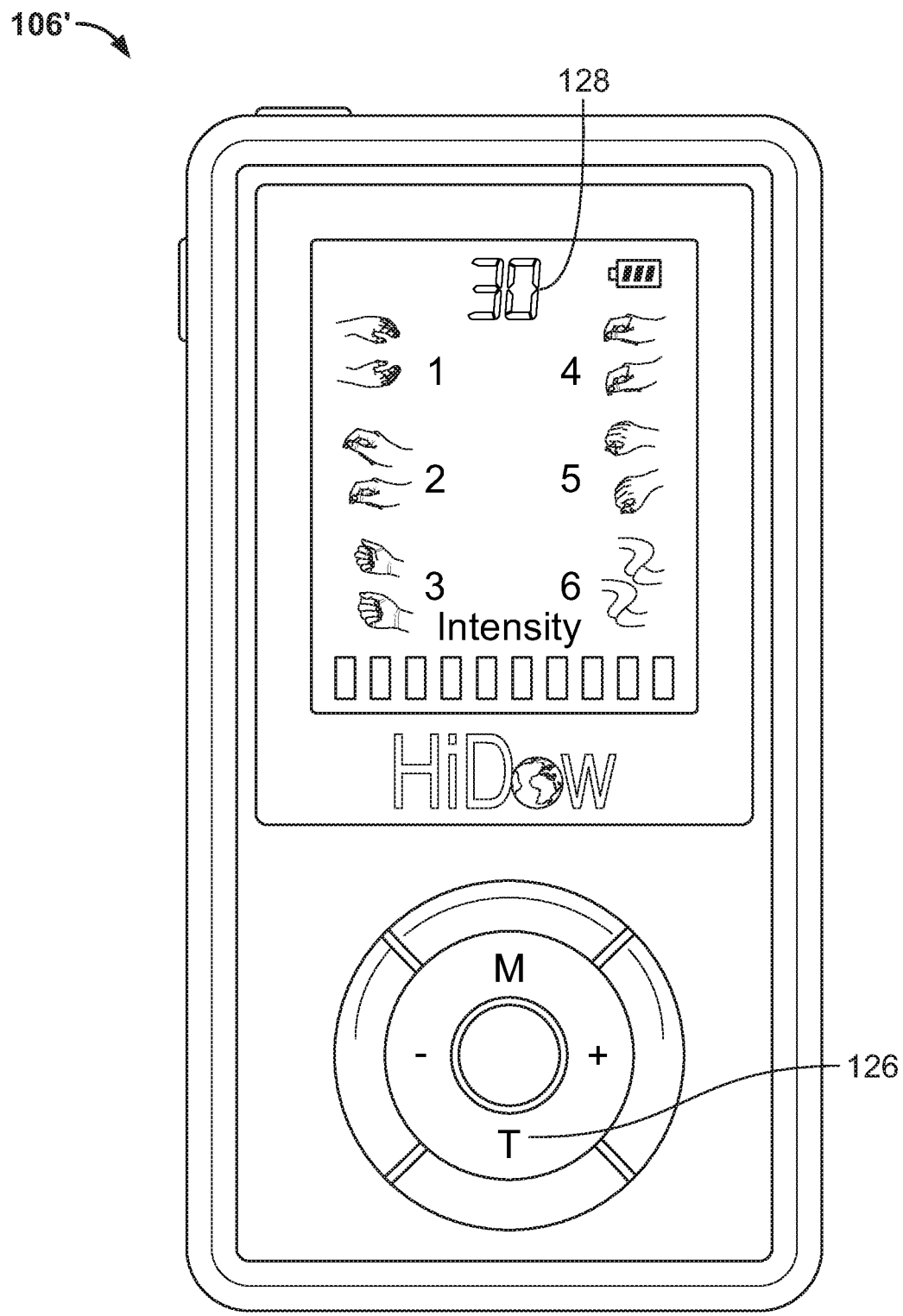
FIG. 20 is a front elevation view of another transmitter having a time selector button.

In an alternative example shown in FIG. 20, the transmitter 106' preferably includes a time selector 126 for selecting a preferred operating time period for at least some of the electrical stimulation units. The time selector 126 is a single remote control button that remotely, wirelessly transmits operating instructions of a user selected operating time period/duration to a selected electrical stimulation unit. The time selector button 126 preferably has a letter "T" on it. A user can select different operating time period by continuing to press the button 126.

As shown in FIG. 20, the transmitter 106' further can include a display 128 for indicating the operating time period selected. When the user presses the time selector button 126, the number on the digital display 128 changes and indicates the operating time (preferably in minutes) being selected for a selected electrical stimulation unit to control with. The display 124 is preferably a digital display showing the number of minutes selected by the user.

In some examples, at least some of the electrical stimulation units turn off when communication with the transmitter 106 is interrupted. In some examples, at least some of the electrical stimulation unit turns off a predetermined time after communication with the transmitter is interrupted. The predetermined time, for example, can be one quarter hour, one half an hour, or an hour. The communication may be interrupted due to a long distance between the electrical stimulation unit and the transmitter. For example, wireless communication technologies typically have a range of about 15 meters outdoors and about 10 meters indoors. The communication may alternatively be interrupted because the transmitter is turned off, or runs out of power. Accordingly, the user can turn off the transmitter to save battery, while the electrical stimulation units can continue operating at the preselected intensity and mode for the predetermined time. This feature may help the user stay safer when using the wireless electrical stimulation system.

In some examples, at least some of the electrical stimulation units preferably include a power switch 130 as shown in FIG. 7. The working status indicator 118 is on/off when the power switch is pressed on/off respectively.

Figure 21:
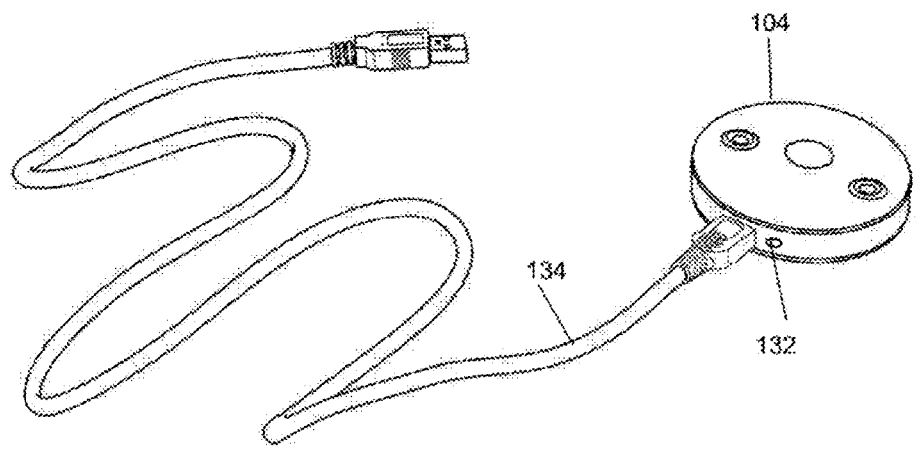
FIG. 21 is a perspective view of an electrode substrate of the wireless electrical stimulation system.
Figure 22:
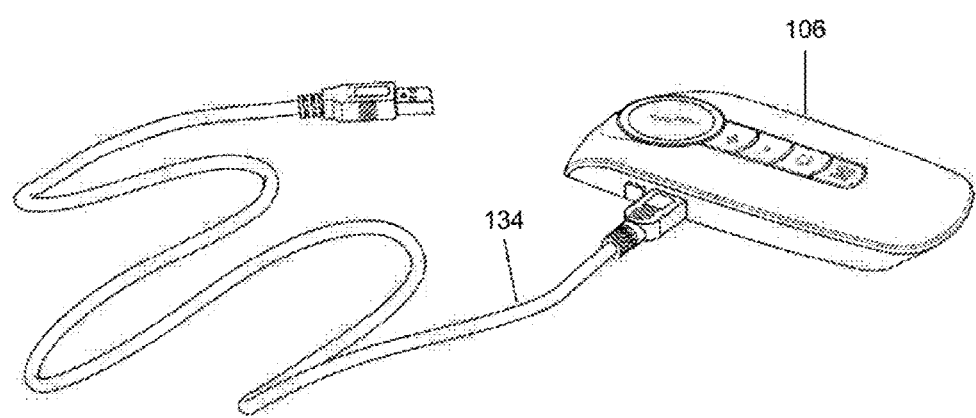
FIG. 22 is a receiver connected with the charging cable of the wireless electrical stimulation system.
Figure 23:
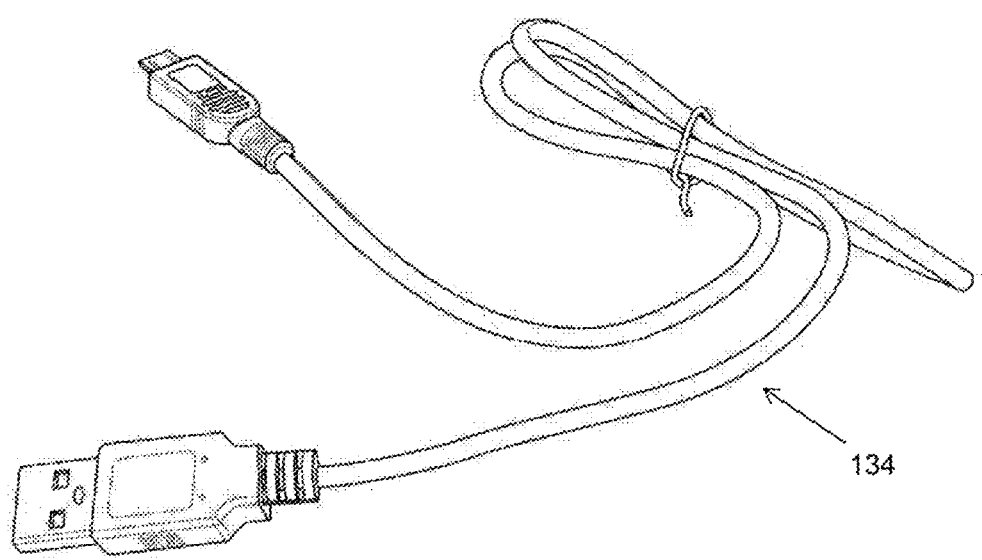
FIG. 23 is a charging cable of the wireless electrical stimulation system.
Figure 24:
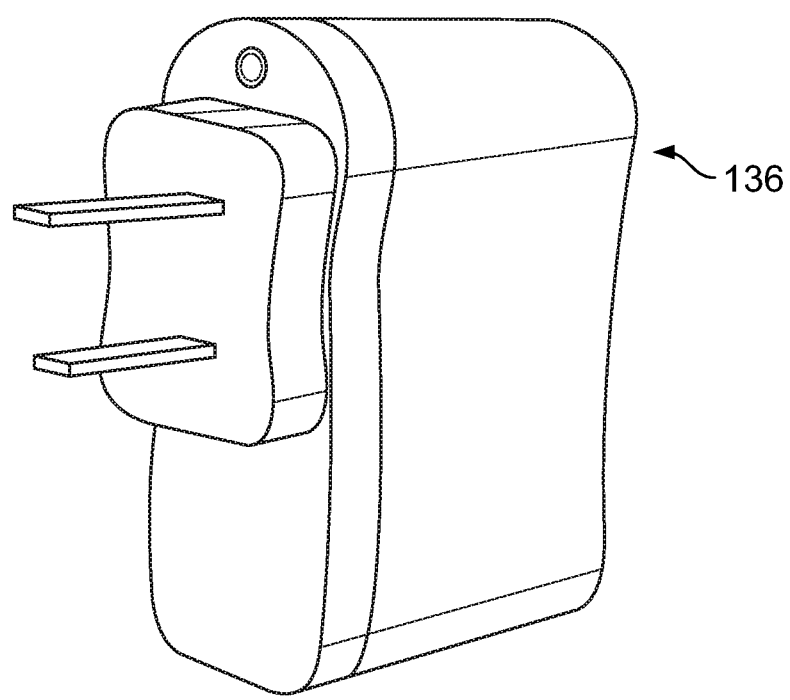
FIG. 24 is the transmitter connected with the charging cable.

Additionally, the transmitter and each electrical stimulation unit preferably include their own internal power supply (not shown). The internal power supply is preferably a rechargeable battery, or other suitable energy storage device. Each electrical stimulation unit preferably includes a charging indicator 132 as shown in FIG. 21. The charging indicator 132 is on when the electrical stimulation unit 104 is charging, and turns off when the electrical stimulation unit 104 is either disconnected form the charging source or is fully charged. Each electrical stimulation unit is preferably charged using a USB connector 134 connecting to an AC adapter 136. As shown in FIGS. 22-24, the USB connector 134 and the AC adapter 136 can also be used to charge a rechargeable battery in the transmitter 106. The transmitter 106 preferably includes a battery display 138 indicates the state of charge and/or charging status.

Figure 25:
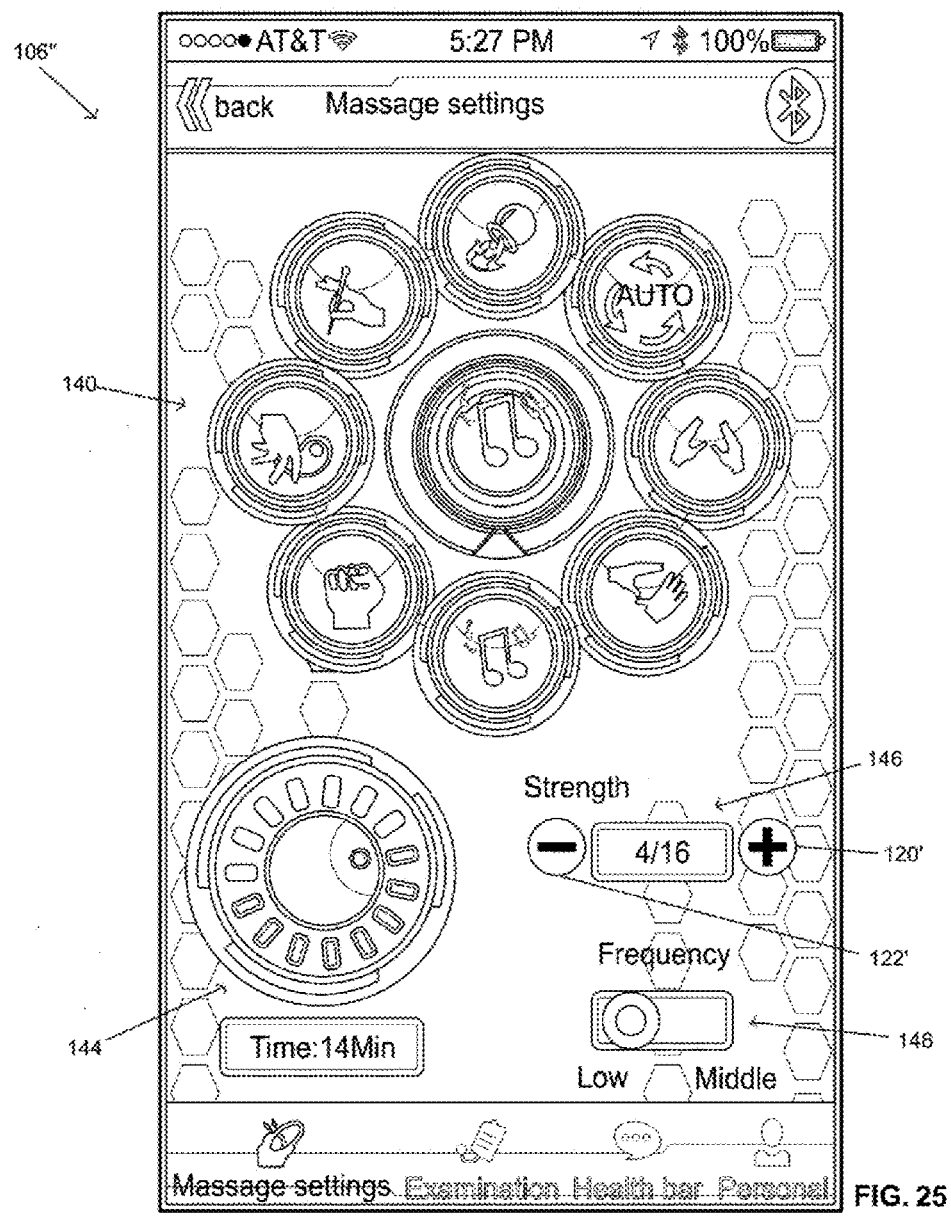
FIG. 25 is a smart phone having an application running as a transmitter of the wireless electrical stimulation system.

Alternatively, the transmitter 106" can be a smart phone running an application as shown in FIG. 25. The smart phone applications have different control buttons for the user to tap on to select the operating modes, operating time period, channels, intensity, massage strength and frequency, etc. For example shown in FIG. 25, the smart phone application can have a mode selector 140 for selecting an operating mode for at least some of the electrical stimulation units. The mode selector 140 preferably includes a group of buttons indicating different operating modes to choose from. The smart phone application preferably includes a time selector 144 for selecting/displaying a preferred operating time period for at least some of the electrical stimulation units. The time selector 144 preferably includes a virtual dial timer. A user can select a preferred operating time period by dialing the virtual dial timer of the time selector 144. The smart phone application further preferably includes an intensity selector 146 and a frequency selector 148 for selecting a preferred operating intensity and a preferred operating frequency respectively. The intensity selector 146 preferably includes an increasing button 120' and a decreasing button 122'. A user can adjust the operating intensity by pressing the buttons 120' and 122' to a level the user desires. The frequency selector 148 preferably includes a virtual slider control. A user can adjust the operating frequency by sliding the virtual slider control of the frequency selector 148 to a frequency the user desires.

In some examples, the transmitter wirelessly communicates with the electrical stimulation units via RF protocol operating in the 2.4 GHz band. For example, Bluetooth or Wifi technologies may be used.

Figure 26:
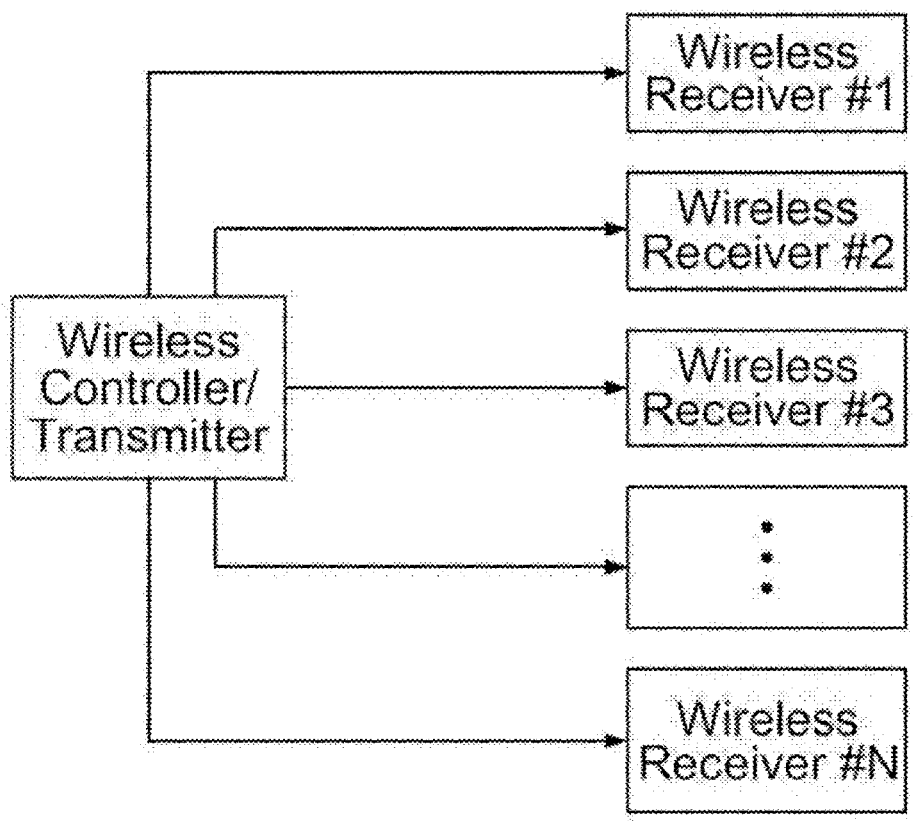
FIG. 26 is a schematic illustration of the wireless electrical stimulation system according to the present disclosure.

As shown in FIG. 26, one transmitter having a master RF transceiver chip can wirelessly control multiple electrical stimulation units having slave RF transceiver chips as receivers through 2.4 GHz wireless connections.

Figure 27:
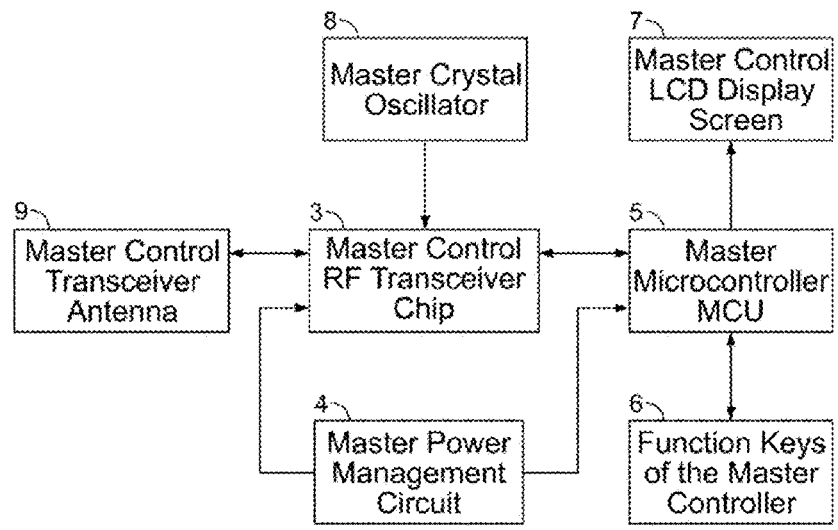
FIG. 27 is a schematic illustration of the transmitter of the wireless electrical stimulation system.

FIG. 27 is a schematic illustration of the transmitter of the wireless electrical stimulation system. The transmitter generally includes the master RF transceiver chip (3) with its input and output connected to a master transceiver antenna (9) and a master microcontroller (5). All the function keys of the master controller (6) are connected to the inputs of the master microcontroller (5). The master control LCD display screen (7) is connected to the output of master microcontroller (5). The input of the master RF transceiver chip (3) may also be connected to an output of a master crystal oscillator (8). A master power management circuit (4) generally supplies the electrical power to the master RF transceiver chip (3) and the master microcontroller (5). The master controller function keys (6) preferably include a channel selector "C", a mode selector "M", a time selector "T", an intensity increaser "+", and an intensity decreaser "−", etc.

Figure 28:
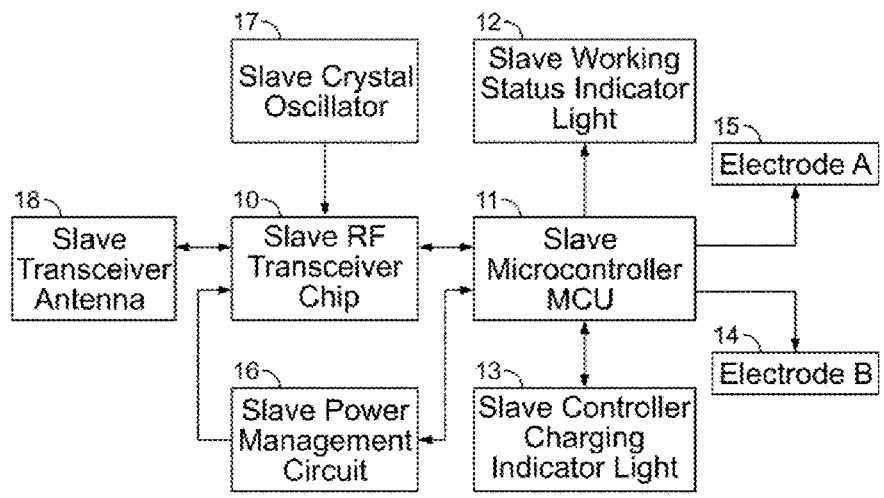
FIG. 28 is a schematic illustration of the receiver/electrical stimulation unit of the wireless electrical stimulation system.

FIG. 28 is a schematic illustration of the receiver/electrical stimulation unit of the wireless electrical stimulation system. The receiver/electrical stimulation unit generally includes a slave RF transceiver chip (10) with its input and output connected to a slave transceiver antenna (18) and a slave microcontroller (11). A slave working status indicator light (12) and a slave controller charging indicator light (13) are connected to the input and output of the slave microcontroller (11). A power switch is connected to the input and output of the slave microcontroller (11). An electrode A (15) and an electrode B (14) are connected to the outputs of the slave microcontroller (12). The input of the slave RF transceiver chip (10) is connected to an output of a slave crystal oscillator (17). A slave power management circuit (16) generally supplies the electrical power to the slave RF transceiver chip (10) and the slave microcontroller (11). The slave microcontroller may also control a slave working status indicator light (12) and a slave charging indicator light.

The wireless operation of a plurality of electrical stimulation units is implemented with the communication between the master RF transceiver chip (3) of the wireless transmitter (1) and the wireless slave RF transceiver chip (10) of the wireless receiver (2).

The master and slave RF transceiver chip (3), (10) is a highly integrated 2.4 GHz wireless transceiver chip. The master and slave microcontrollers (5) and (11) communicate with each other by using a transmit-receive FIFO register on the chip to store the data, and then transfer at a maximum 2 Mbps rate in the air to accomplish the wireless control.

The slave RF transceiver chip (10) is preferably a highly integrated 2.4 GHz RF transceiver chip. The slave RF transceiver chip (10) receives a data packet from the transmitter. The data packet is preferably an 8-bit unsigned data packet and is preferably stored in a First-In-First-Out (FIFO) register. The slave RF transceiver chip (10) then sends an Acknowledgement (ACK) signal to the transmitter to notify the transmitter that the data packet has been safely received. The maximum data transfer rate is preferably 2 Mbps. The buffer of the FIFO register is cleared after a communication is finished and the register is ready for the next communication.

The transmitter of the wireless electrical stimulation system preferably matches the code sent by each electrical stimulation units with a predetermined code before connecting with one of the plurality of the electrical stimulation units to further control the operation of each electrical stimulation unit. The transmitter preferably communicates with different electrical stimulation units on different channels at different frequencies. Alternatively the communication could be on the same channel at the same frequency, with each message encoded for a particular electrical stimulation unit. Of course in some applications it may be desirable that a transmitter simultaneously control multiple electrical stimulation units, and thus in some examples at least some of the electrical stimulation units operate on the same channel or frequency, or are responsive to the same encoded signals.

Further, in order to allow more convenient control, the transmitter of the wireless electrical stimulation system preferably consolidates all the necessary selector displays on one single LCD screen. The LCD screen also displays the working status of the electrical stimulation units, such as the operating modes, the operating intensities, the operation time periods, etc., and the status of the transmitter, such as the state of the charge and the receivers currently being controlled, etc.

In an alternative example, an electrical stimulation system may further include a cable configured to electrically connect the electrical stimulation unit to at least two electrodes to apply electrical stimulation signals from the electrical stimulation unit to the electrodes positioned remotely from the electrical stimulation unit. Thus, the electrodes can be adapted to be disposed in electrical contact with a subject's body located far away from the single electrical stimulation unit. Further, the electrodes can also be disposed spaced apart from each other so that parts of the subject's body spaced further apart from each other can be treated. For example, limbs of the body, sides of the back, and/or sides of the waist, etc. This has largely increased applications of the electrical stimulation system.

Figure 29:
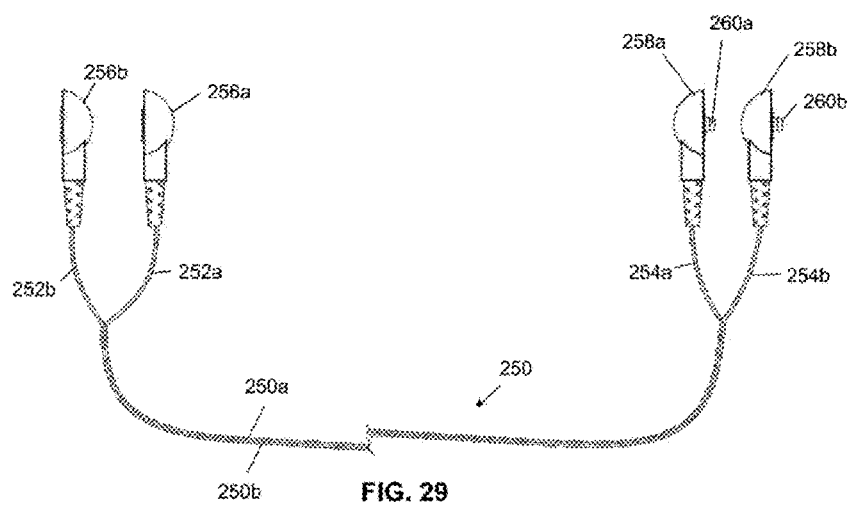
FIG. 29 is an exemplary X-cable of the wireless electrical stimulation system.
Figure 30:
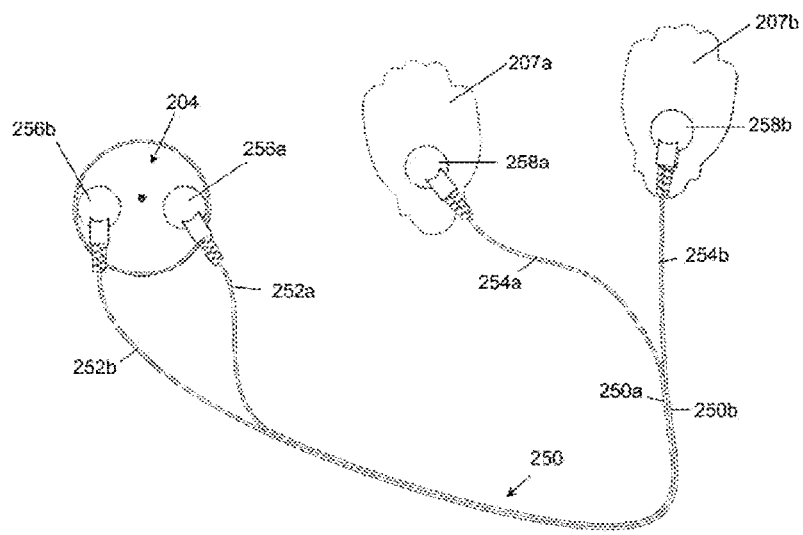
FIG. 30 illustrates a receiver/electrical stimulation unit connected with electrodes using the exemplary X-cable of FIG. 29.

FIGS. 29-30 illustrate an exemplary cable 250 that can be used to electrically connect an electrical stimulation unit 204 to the two electrodes 207a, 207b to apply electrical stimulation signals from the electrical stimulation unit 204 to the electrodes 207a, 207b positioned remotely from the electrical stimulation unit 204, As shown in FIGS. 29-30, the exemplary cable 250 is an X-cable having two input branches 252a, 252b and two output branches 254a, 254b, connectors 256a, 256b on each of the input branches 252a, 252b adapted to be connected to the electrical stimulation unit 204, and connectors 258a, 258b on each of the output branches 254a, 254b adapted to connected to electrodes 207a, 207b respectively. The cable 250 may include two plastic wrapped flexible copper wires 250a, 250b that are bonded with each other in parallel. The two bonded wrapped wires may be easily torn apart so that the two branches 254a, 254b can become longer and connectors 258a, 258b can be spaced further apart from each other, such that parts of the body spaced further apart from each other and from the electrical stimulation unit 204 can be treated.

In some examples, the connectors 256a, 256b on the input branches 252a, 252b can be permanently attached (e.g., soldered, welded, brazed, cemented, etc.) to the electrical stimulation unit 204.

Additionally, the connectors 258a, 258b on the output branches 254a, 254b of some examples can be permanently attached (e.g., soldered, welded, brazed, cemented, etc.) to electrodes 207a, 207b respectively.

In some examples, the connectors 256a, 256b on the input branches 252a, 252b may include metal fasteners configured for removably coupling with corresponding structures of the electrical stimulation unit 204. For example, as shown in FIGS. 29-30, the metal fasteners on the connectors 256a, 256b may be a pair of female metal snaps for attaching to a pair of male metal snaps on the electrical stimulation unit 204, or vice versa.

In some examples, the connectors 258a, 258b on the output branches 254a, 254b may also include fasteners configured for removably coupling with corresponding structures on the electrodes 207a, 207b respectively. For example, as shown in FIGS. 29-30, the metal fasteners on the connectors 258a, 258b may be a pair of male metal snaps 260a, 260b for attaching to a pair of female metal snaps on the electrodes 207a, 207b, or vice versa.

The metal snaps can alternatively be some other type or design of fastener for releasably engaging and electrically connecting the cable 250 to the electrical stimulation unit 204 and/or the electrodes 207a, 207b. Some other fastening force may also be used, such as with magnets, vacuum (like suction cups), or even friction.

An electronic circuit is formed by the cable 250 connecting from the electrical stimulation unit 204 to the electrodes 207a, 207b to apply an electrical stimulation to tissue in electrical contact with the electrodes 207a, 207b.

The electrodes 207a, 207b can be carried on substrates adapted to be applied on a body surface. In some examples, the electrodes 207a, 207b can be carried on a pair of articles of clothing (e.g., a pair of gloves, a pair of socks, a pair of slippers, etc.) that can directly contact particular areas of the body surface.

Figure 31:
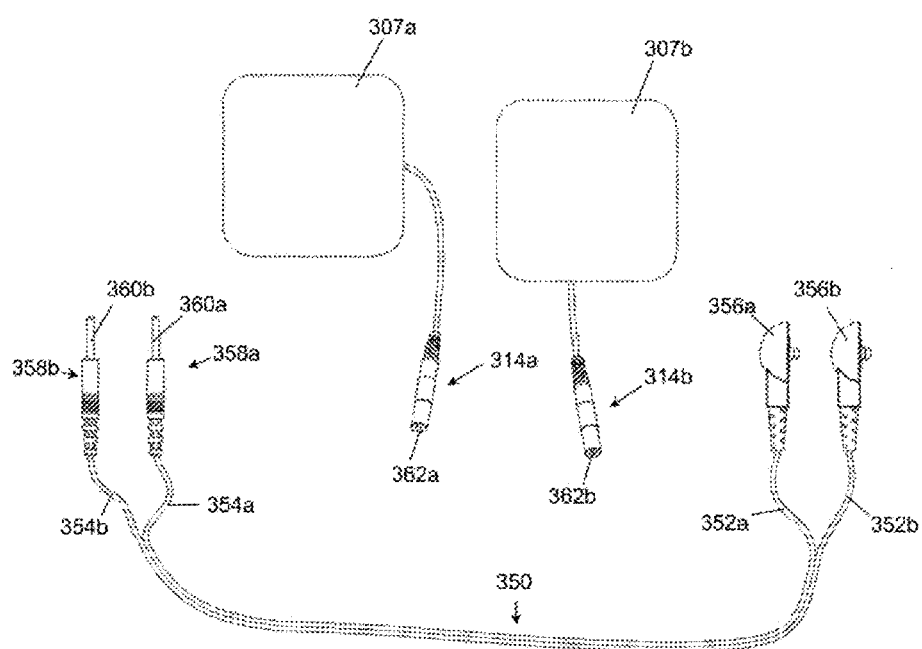
FIG. 31 illustrates another exemplary X-cable adapted to connect with electrodes of the wireless electrical stimulation system.

FIG. 31 shows an alternative X-cable 350 that is used to electrically connect an electrical stimulation unit to the two electrodes 307a, 307b, The X-cable includes similar features/structures as the X-cable 250 except that the connectors 358a, 358b of the output branches 354a, 354b may include needle/plug style connectors configured for removably interfacing with corresponding needle/plug style connectors 314a, 314b attached on the electrodes 207a, 207b respectively. For example, as shown in FIG. 31, the connectors 358a, 358b may include metal pins 360a, 360b for inserting into sockets 362a, 362b of connectors 314a, 314b of the electrodes 307a, 307b, or vice versa. Specifically, the needle/plug style connectors may be 3.5 mm standard connectors.

Figure 32:
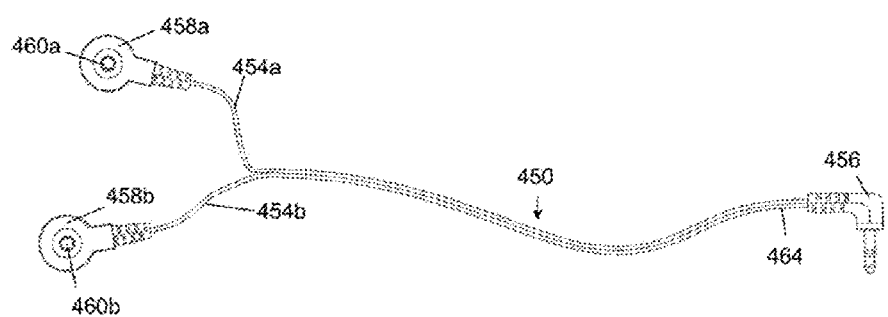
FIG. 32 is an exemplary Y-cable of the wireless electrical stimulation system.
Figure 33:
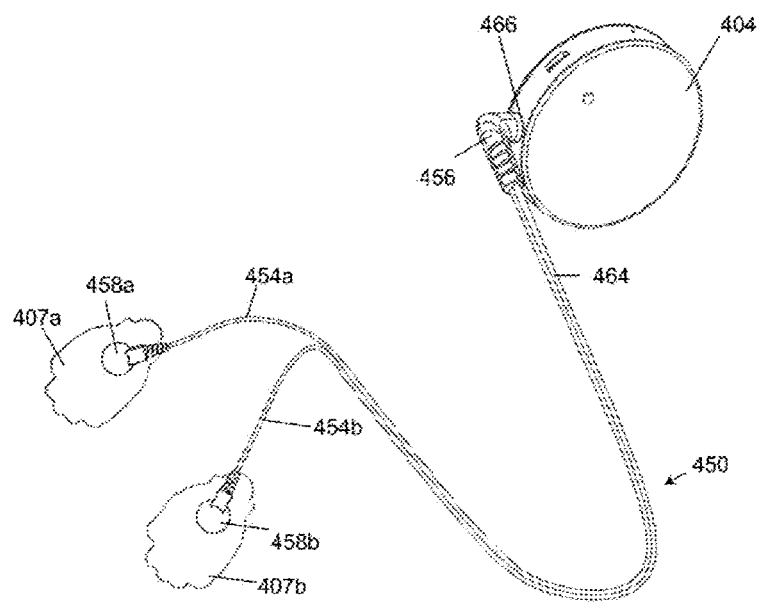
FIG. 33 illustrates a receiver/electrical stimulation unit connected with electrodes using the exemplary Y-cable of FIG. 32.

FIGS. 32-33 illustrate a Y-cable 450 that can be used to electrically connect an electrical stimulation unit 404 to the two electrodes 407a, 407b to apply electrical stimulation signals from the electrical stimulation unit 404 to the electrodes 407a, 407b positioned remotely from the electrical stimulation unit 404, As shown in FIGS. 32-33, the Y-cable 450 includes a stem 464 and two branches 454a, 454b, with a plug 456 disposed on the end of the stem 464 and connectors 458a, 458b disposed on the branches 454a, 454b respectively. The plug 456 is configured to couple with a socket 466 on the electrical stimulation unit 404. Similar to the X-cables 250, 350, each of the connectors 458a, 458b are configured for attaching and electrically connecting to electrodes 407a, 407b respectively. Also similar to cables 250, 350, the two bonded wrapped wires of the stem 464 can be easily torn apart so that the two branches 454a, 454b become longer and connectors 458a, 458b can be spaced further apart from each other, such that the electrodes 407a, 407b can treat further apart spaced parts of the body.

Similar to the cable 250, the connectors 458a, 458b on the branches 454a, 454b of some examples can be permanently attached (e.g., soldered, welded, brazed, cemented, etc.) with electrodes 407a, 407b respectively.

In some examples, the connectors 458a, 458b on the output branches 454a, 454b may also include fasteners configured for removably coupling with corresponding structures on the electrodes 407a, 407b respectively. For example, the metal fasteners on the connectors 458a, 458b may be a pair of male metal snaps 460a, 460b for attaching to a pair of female metal snaps on the electrodes 407a, 407b, or vice versa.

The metal snaps can alternatively be some other type or design of fastener for releasably engaging and electrically connecting the cable 450 to the electrodes 407a, 407b. Some other fastening force may also be used, such as with magnets, vacuum (like suction cups), or even friction.

In some examples, the plug 456 may be a 3.5 mm standard plug configured for inserting into the socket 468 of the stimulation unit 404 to receive electrical stimulation signals from the electrical stimulation unit 404.

FIGS. 34-38 illustrate another example of an electrical stimulation system 200 according to the present disclosure. In the example shown by FIG. 34, the system 200 generally includes at least two electrodes carried on a single substrate 507 adapted to be disposed in electrical contact with a body surface, and an electrical stimulation unit 202 configured to deliver electrical pulses to muscle groups or nerve endings adjacent a body surface that is in electrical contact with the at least two electrodes. The electrical stimulation unit 202 includes an on-board controller configured for controlling the stimulation unit 202 to deliver electrical pulses for pain relief and/or muscle relaxation.

Figure 34:
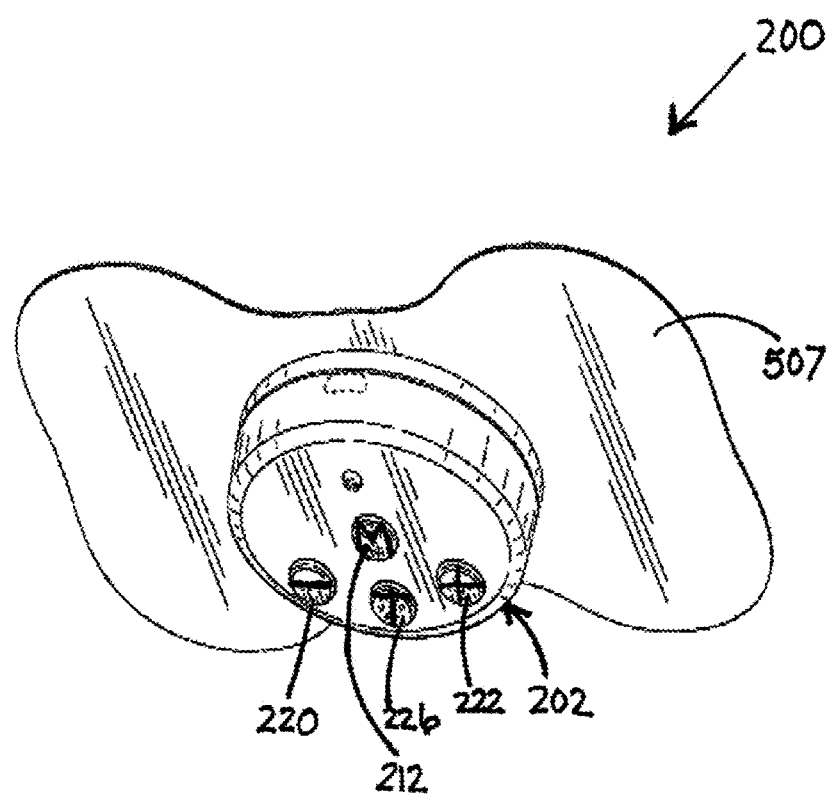
FIG. 34 is a perspective view illustrating another example of an electrical stimulation system according to the present disclosure, where the electrical stimulation unit is attached to another exemplary electrode substrate having a butter-fly shape.

In some examples, at least some of the electrical stimulation units are capable of operating at at least two intensities. As shown in FIG. 34, the electrical stimulation unit 202 includes intensity selectors, 220, 222 for selecting different intensities. In the example shown in FIG. 34, the intensity selectors include an increase button 220 and a decrease button 222 for increasing and decreasing the operating intensity for the electrical stimulation unit to be controlled with the on-board controller. For example, the increase button 220 and decrease button 222 are pressed and transmit operating instructions of a user selected intensity to the on-board controller thereby operating the electrical stimulation unit 202 at the selected intensity. The increase and decrease buttons 220 and 222 preferably have "+" and '−' signs respectively, to indicate their function to the user. A user can adjust the operating intensity by pressing the buttons 220 and 222 to a level the user desires.

In some examples, the electrical stimulation unit is operable at a plurality of operating modes, each of which applies a different time-varying electrical potential to the at least two electrodes. The on-board controller includes a mode selector for selecting one of the plurality of operating modes for the electrical stimulation unit.

The electrical stimulation unit 202 preferably further includes a mode selector 212 for selecting an operating mode for the electrical stimulation unit 202. The mode selector 212 is configured for a user to select one of a plurality of operating modes for the electrical stimulation unit 202. The mode selector button 212 preferably has a letter "M" on it, indicating to the user that the button controls the mode. A user can select different operating modes by pressing the button 212, which cycles through the available modes. The mode selector button 212 can be pressed to enter the mode selection mode, and the increase and decrease buttons 220 and 222 can be operated to select the desired mode.

In some examples, the electrical stimulation unit 202 includes a time selector 226 for selecting a preferred operating time period. The time selector 226 is a single remote control button that transmits operating instructions of a user selected operating time period/duration to the on-board controller thereby operating the electrical stimulation unit for the selected time period. The time selector button 226 preferably has a letter "T" on it. A user can select different operating time period by continuing to press the button 226.

In some examples, the electrical stimulation unit 202 may further include an audible alarm configured to send an alert in response to at least one operating instruction.

Figure 35:
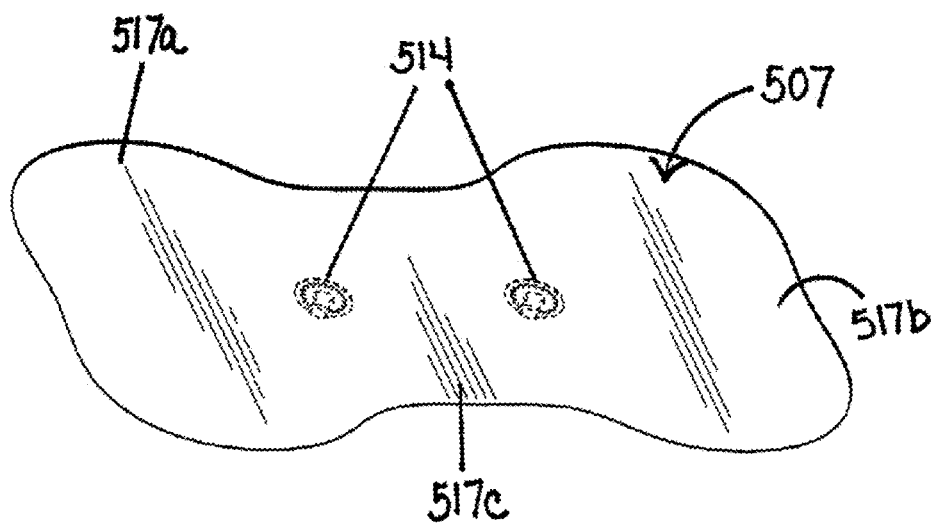
FIG. 35 is a front elevation view of the electrode substrate of FIG. 34.
Figure 37:
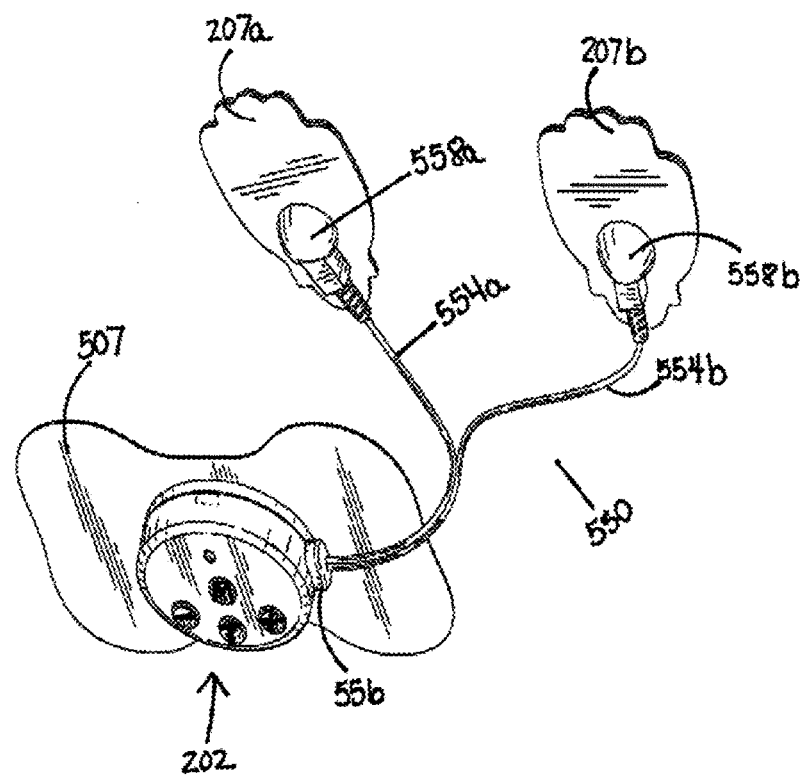
FIG. 37 is a perspective view illustrating the electrical stimulation unit of FIG. 34 attached with electrode substrate of FIG. 35 and connected with additional electrodes using the exemplary Y-cable of FIG. 36.

As shown in FIGS. 34-35, the single substrate 507 has a general butterfly or a bone shape, with first and second lobes 517a, 517b joined at a central junction or portion 517c. The substrate 507 is a generally thin, flexible planar adapted to be disposed in electrical contact with a body surface. As shown in FIG. 35, the two lobes 517a, 517b extend from the central junction or portion 517c to the two opposite sides of the central portion 517c. The widths of the two lobes are substantially the same and larger than the width of the central portion 517c. Although FIGS. 34, 35, and 37 illustrate that the single substrate 507 generally includes a butterfly or bone shape. Other geometric shapes of the single substrate 507 are contemplated with the scope of the invention. Example shapes include, without limitation, circular, rectangular, square, oval, triangular, and polygonal shapes.

Similar to the substrate 107, as shown in FIG. 35, the single substrate 507 may preferably include a pair of male metal snaps 514 for attaching to a pair of female metal snaps on the electrical stimulation unit 202. The metal snaps can alternatively be some other type or design of fastener for releasably engaging and electrically connecting the electrode pad 507 to the electrical stimulation unit.

In some examples, the system 200 further includes a cable electrically connecting the electrical stimulation unit 202 to at least two electrodes to deliver the electrical pulses from the electrical stimulation unit 202 to the at least two electrodes positioned remotely from the electrical stimulation unit. The cable can be, for example, the X-shaped cable 250 or the Y-shaped cable 450, as disclosed above.

Figure 36:
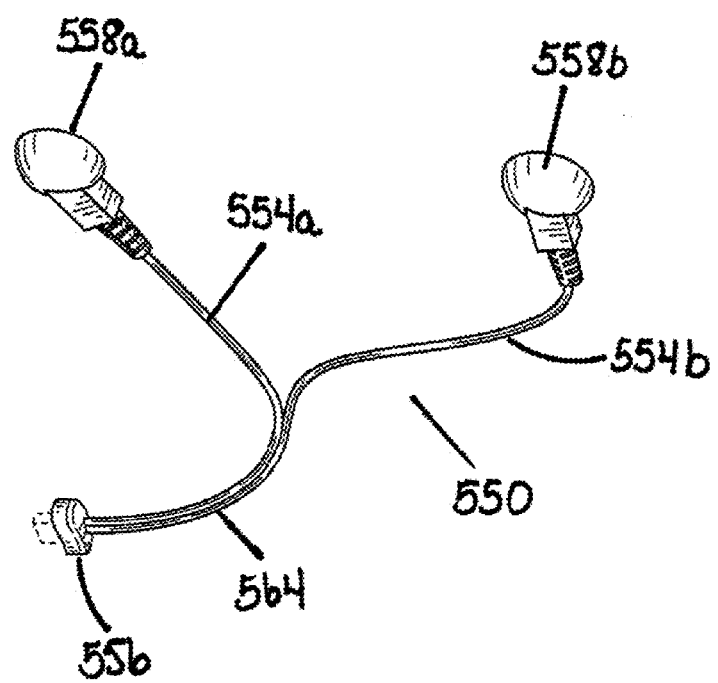
FIG. 36 is another exemplary Y-cable of the wireless electrical stimulation system.

Alternatively, as shown in FIG. 36, the cable can be a Y-shaped cable with a stem 564 and two branches 554a, 554b, with a connector 556 disposed on the free end of the stem 564, and connectors 558a, 558b respectively disposed on each end of the branches. Unlike the Y-shaped cable 450 of FIG. 32 with a regular plug 456 disposed on the end of the stem 464, the Y-shaped cable 550 shown in FIG. 37 includes a different type of connector 556 (e.g., a Centronics connector, a DB connector, an Internal connector, or a USB connector, etc.) disposed on the end of the stem 564 configured to electrically couple with a mating connector on the electrical stimulation unit 202, and each of the connectors 558a, 558b on the branches 554a, 554b is configured for electrically connecting to each electrode of two additional auxiliary substrates.

Similar to Y-shaped cable 450 of FIG. 32, the connector on each of the branches may permanently attach the branches to the electrodes on the substrate. Alternatively, the connector on each of the branches may include a metal fastener configured for removably connection to the electrodes on the substrate.

In this example shown in FIGS. 34 and 37, the at least two electrodes carried on the single substrate 507 are connected directly to the electrical stimulation unit 202.

As shown in FIG. 37, the system additionally includes a first auxiliary electrode carried on the first auxiliary substrate 207a, and a second auxiliary elected carried on a second auxiliary substrate 207b, and a cable having at least one connector configured to electrically couple with a mating connector on the electrical stimulation unit 202, and connectors configured for electrically connecting to each of the first and second auxiliary electrodes, spaced remotely from the electrical stimulation unit 202 and from each other.

In this example shown in FIG. 37, the first and the second auxiliary substrates 207a, 207b each have a leaf or a hand shape.

Figure 38:
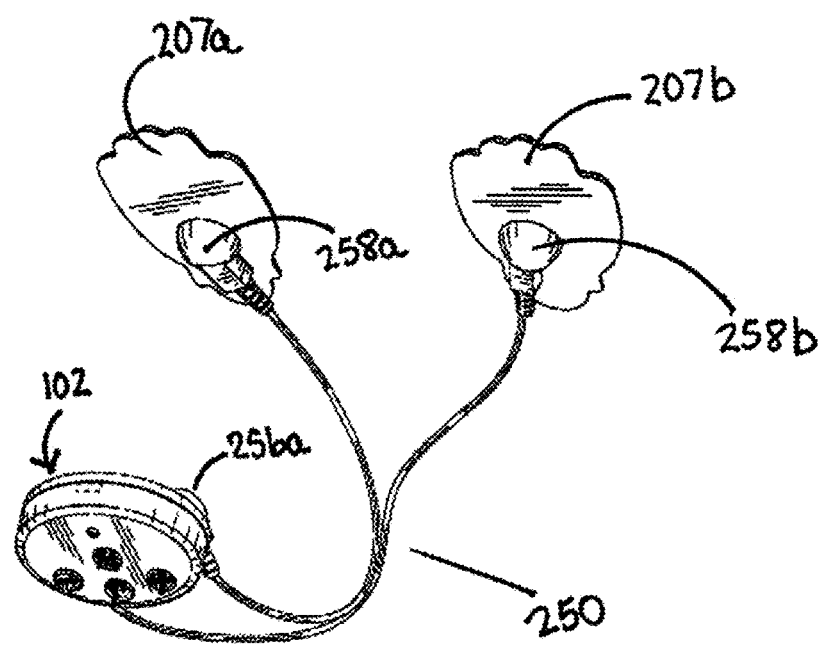
FIG. 38 is a perspective view illustrating the electrical stimulation unit of FIG. 34 connected with electrodes using the exemplary X-cable of FIG. 29.

Alternative, as shown in FIG. 38, when the cable has an X-shaped configuration, which includes first and second input branches, and first and second output branches, connectors 256a, 256b on each of the input branches adapted to be connected to the electrical stimulation unit 202, and connectors 258a, 258b on each of the output branches configured for electrically connecting to one of the first and second auxiliary electrodes 207a, 207b.

In some examples, the connectors 256a, 256b on the input branches of the X-shaped cable 250 are configured for permanently attaching with the electrical stimulation unit 202.

Alternatively, in some other examples, the connectors 256a, 256b on the input branches of the X-shaped cable 250 include metal fasteners configured for removably coupling with corresponding structures of the electrical stimulation unit 202.

In some examples, the connectors 258a, 258b on the output branches of the X-shaped cable 250 are configured for permanently attaching to the first and second auxiliary electrodes 207a, 207b.

In some examples, the connectors 258a, 258b on the output branches of the X-cable 250 include metal fasteners configured for removably attaching to the first and second auxiliary electrodes 207a, 207b.

Sometimes, heat may increase blood flow and make connective tissue more flexible. The heat may temporarily block pain, help reduce inflammation and stiffness, and improve range of motion. Thus, heat may be applied to a body surface or to deep tissues. Hot packs, infrared heat and hydrotherapy provide surface heat. Electric currents or ultrasound generate heat in deep tissues. Therefore, there may be a need to incorporate a body surface heating function and a deep tissues heating function so as to improve the therapeutic effect of electrical stimulation systems.

Acupoints are stimulated by acupuncture. With the implementation of electrical stimulation systems, however, electrotherapy can be a major means of acupoint stimulation, given the fact that acupoints have low electrical resistance and high conductivity. Therefore, there may be a need to incorporate electrical stimulation and acupuncture to treat, for example, feet and hands, where many acupoints are located.

Figure 39:
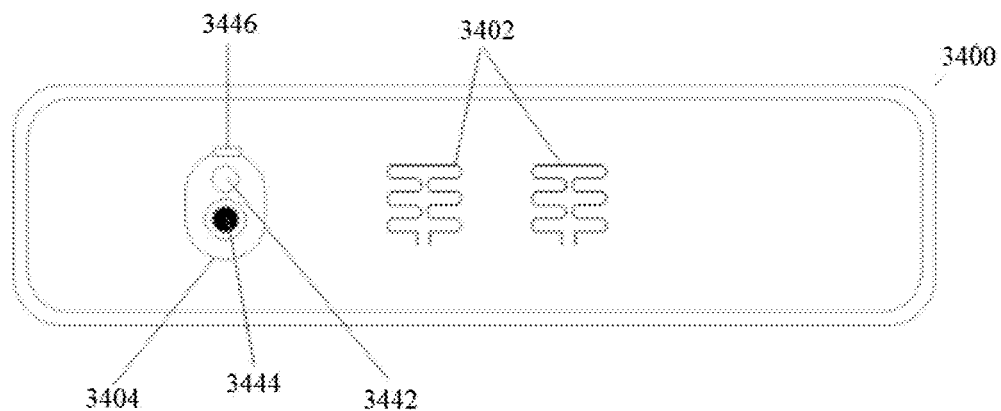
FIG. 39 is a view of an outer portion of a therapy belt according to one example of the present disclosure.
Figure 40:
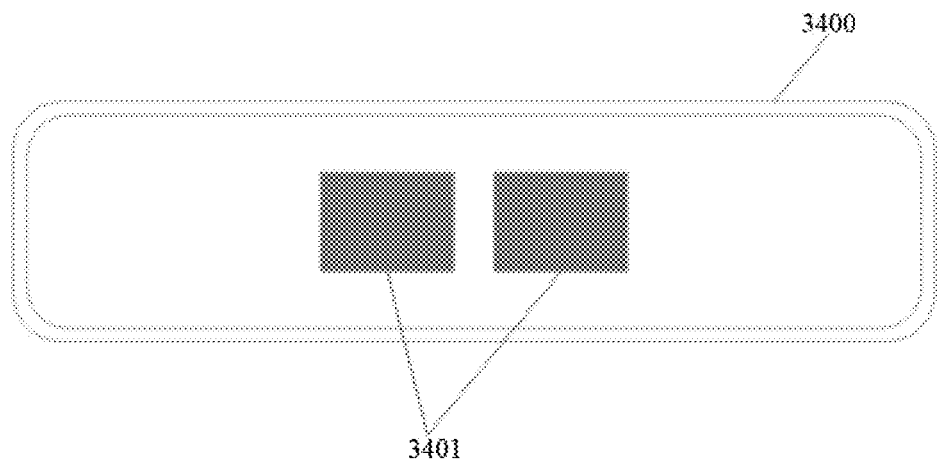
FIG. 40 is a view of an inner portion of the therapy belt of FIG. 39 according to one example of the present disclosure.

FIG. 39 is a view of an outer portion of a therapy belt according to one example of the present disclosure. A therapy belt 3400 includes an outer portion as shown in FIG. 39, and the therapy belt 3400 also includes an inner portion as shown in FIG. 40. The outer portion of the therapy belt 3400 (FIG. 39) illustrates the therapy belt 3400 along an outer circumference, and the inner portion of the therapy belt 3400 (FIG. 40) illustrates the therapy belt 3400 along an inner circumference. An interlayer is formed between the outer portion of the therapy belt 3400 (FIG. 39) and the inner portion of the therapy belt 3400 (FIG. 40). As shown in FIG. 39, the therapy belt 3400 includes at least two therapy electrodes 3402 that are placed in the interlayer of the therapy belt 3400. The therapy electrodes 3402 may each include a corresponding Pulsed Electro-Magnetic Field (PEMF) radiating antenna or another type of antenna. Alternatively or additionally, one or more antennas may be located anywhere on the therapy belt 3400. When more than one antenna is provided, each antenna can each be implemented using the same type of antenna, or alternatively, each antenna can be implemented using a different type of antenna. In some examples, each of the antennas may be positioned such that no antenna overlaps any of the therapy electrodes 3402.

The therapy belt 3400 may also include a controller 3404 that is placed on the outer portion of the therapy belt 3400. The controller 3404 is configured for controlling each of the therapy electrodes 3402 to apply a time-varying electrical signal or waveform to body tissue. For example, the controller 3404 may control the PEMF radiating antennas to emit a radio frequency signal. In some examples, the radio frequency signal may be in the range of 27-30 MHz, or at a frequency of 27.12 MHz.

As illustrated in FIG. 39, the controller 3404 may include a power button 3444 and a power indicator 3442. In one example, when the power button 3444 is first depressed or is simply pushed, the controller 3404 turns ON and begins being supplied with power. When the power button 3444 is depressed or is pushed again, the controller turns OFF and stops being supplied with power. Additionally, the power button 3444 may incorporate the power indicator 3442, such that the power indicator 3442 is electrically coupled to a power supply (not illustrated) in the controller 3404, and/or a processor, to indicate whether or not the controller 3404 is working, which is indicative of whether the power supply is in an ON condition versus an OFF condition. For example, the power indicator 3442 may be a light that illuminates in response to the power supply being ON. The power indicator 3442 may be a light that is in an off state which indicates that the power supply is OFF. Illustratively, the power indicator 3442 may be an LED light, an incandescent lamp, a neon lamp, an audible alarm, a flashing light, or any of various combinations thereof.

The controller 3404 may include its own internal power supply (not shown). The internal power supply may be a battery, or other suitable energy storage device. The battery may be rechargeable, or removable or both rechargeable and removable. The controller 3404 may further include a charging connector 3446 through which the internal power supply in the controller 3404 may be charged. The charging connector 3446 may be a USB charging connector or the like.

FIG. 40 is a view of the inner portion of the therapy belt 3400 of FIG. 39 according to one example of the present disclosure. The inner portion of the therapy belt 3400 (FIG. 40) illustrates the therapy belt 3400 along an inner circumference. The therapy belt 3400 may further include at least two heating pads 3401 that may be placed along the inner circumference of the therapy belt 3400 and may be in direct contact, or thermally coupled, with a person's skin when the person wears the therapy belt 3400. The position of each respective heating pad of the heating pads 3401 (FIG. 40) on the inner portion of the therapy belt 3400 may or may not be arranged to correspond to the position of a corresponding therapy electrode of the therapy electrodes 3402 (FIG. 39) on the outer portion of the therapy belt 3400. The heating pads 3401 (FIG. 40) may each be a heating pad with a removable and changeable gel pack that provides rapid initial warming when exposed to the air.

Figure 41:
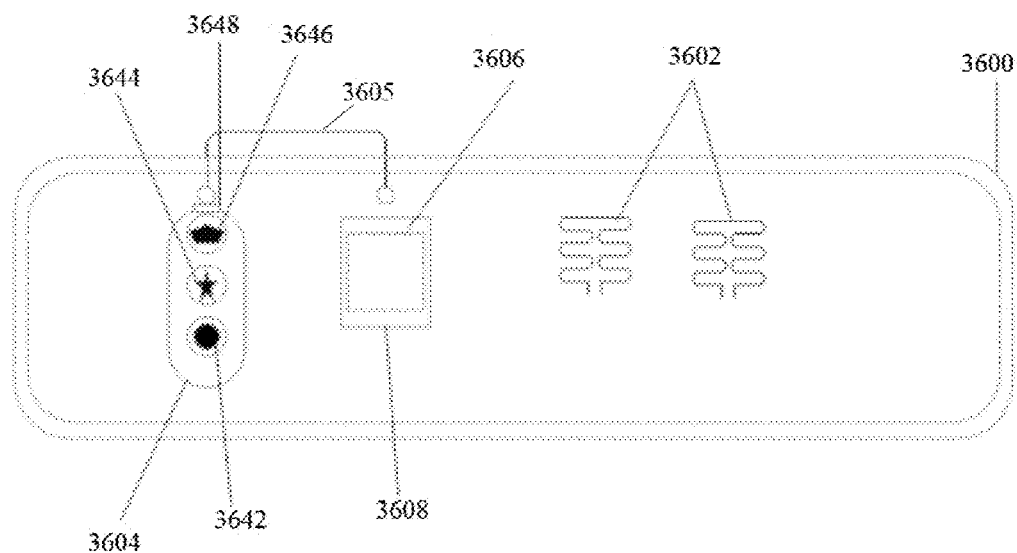
FIG. 41 is a view of an outer portion of a therapy belt according to another example of the present disclosure.

FIG. 41 is a view of an outer portion of a therapy belt 3600 according to one example of the present disclosure. The outer portion of the therapy belt 3600 illustrates the therapy belt 3600 along an outer circumference. In this example, the therapy belt 3600 includes a heating device and an electrical stimulation device. The electrical stimulation device includes at least two therapy electrodes 3602 that are each configured to emit electrical or radio frequency (RF) signals.

Figure 42:
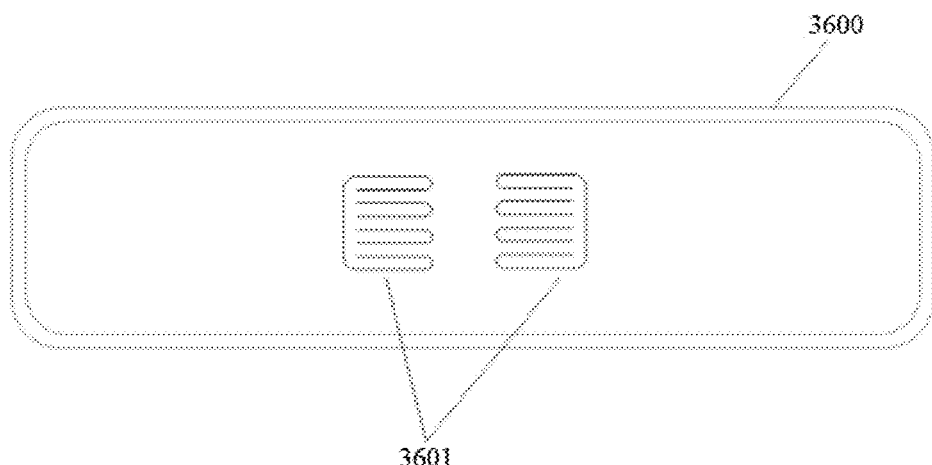
FIG. 42 is a view of an inner portion of the therapy belt of FIG. 41 according to another example of the present disclosure.

In this example, the therapy belt 3600 includes the outer portion (FIG. 41) as well as an inner portion (FIG. 42). An interlayer is formed between the outer portion of the therapy belt 3600 (FIG. 41) and the inner portion of the therapy belt 3600 (FIG. 42). The at least two therapy electrodes 3602 (FIG. 41) are placed in the interlayer of the therapy belt 3600. One or more respective therapy electrodes of the at least two therapy electrodes 3602 may include a corresponding PEMF radiating antenna that communicates with a controller to control or activate the one or more respective therapy electrodes. In some implementations, one PEMF radiating antenna may be used. In other implementations, a plurality of PEMF radiating antennas may be provided, and in still other implementations, one or more antennas other than PEMF radiating antennas are provided. Illustratively, one or more antennas may be configured to accept RF power remotely and generate heat locally.

The therapy belt 3600 (FIG. 41) may also include a controller 3604 that is placed on the outer portion of the therapy belt 3600. The controller 3604 is configured for controlling each of the at least two therapy electrodes 3602 to selectively apply a time-varying electrical signal to body tissue. For example, the controller 3604 may control the PEMF radiating antennas to emit a radio frequency signal. According to a further example disclosed herein, the radio frequency signal may be within the range of 27 MHz to 30 MHz. According to a still further example, the radio frequency signal may be at 27.12 MHz. The controller 3604 may be connected to the at least two therapy electrodes 3602 via a wire connection or a wireless connection, or any of various combinations thereof.

The controller 3604 may include a power button 3642. The power button 3642 may be provided with a power indicator. In one example, when the power button 3642 is depressed for a period of time that meets or exceeds a predetermined length of time, the power button 3642 is placed in an ON state wherein the controller 3604 turns ON and starts being supplied with power. When the power button 3642 is depressed again for the period of time that meets or exceeds the predetermined length of time, the power button 3642 is placed in an OFF state wherein the controller 3604 turns OFF and stops being supplied with power. Additionally, the power button 3642 may incorporate a power indicator, such as an LED light, incandescent light, neon bulb, flashing light, audible alarm, or any of various combinations thereof, which is electrically coupled to a portable power supply 3606 and/or a power supply (not illustrated) in the controller 3604, and/or a processor, to indicate whether or not the controller 3604 is being provided with power. For example, when the power button 3642 is in the ON state, the power indicator is illuminated, and when the power button 3642 is in the OFF state, the power indicator is not illuminated. Alternatively or additionally, the power indicator may be configured to provide a first visual display or audible annunciation for the ON state of the power button 3642, and a second visual display or audible annunciation for the OFF state of the power button 3642, where the first visual display or audible annunciation is different from the second visual display or audible annunciation.

The controller 3604 may include a PEMF control button 3644. The PEMF control button may include a PEMF indicator integrated therein. In one example, when the PEMF control button 3644 is first depressed for a short period of time less than the predetermined length of time, the electrical stimulation apparatus turns ON and begins generating therapeutic electrical or RF signals. When the PEMF control button 3644 is depressed again for the short period of time, the electrical stimulation apparatus turns OFF and stops generating the therapeutic electrical or RF signals. Additionally, the PEMF control button 3644 may incorporate the PEMF indicator, such as an LED light, incandescent light, neon bulb, flashing light, audible alarm, or any of various combinations thereof, that are electrically coupled to a portable power supply 3606, and/or a power supply (not illustrated) in the controller 3604, and/or a processor, to indicate whether or not the electrical stimulation apparatus is working.

The controller 3604 may include a heating control button 3646 and a heating indicator (not illustrated). In one example, when the heating control button 3646 is first depressed for the short amount of time less than the predetermined length of time, the heating apparatus turns ON and begins heating. When the heating control button 3646 is depressed again for the short amount of time, the heating apparatus turns OFF and stops heating. The heating apparatus may be included in one or both of the at least two therapy electrodes 3602. The heating apparatus may also be placed separately from the therapy electrodes 3602, on or within the therapy belt 3600. Additionally, the heating control button 3646 may incorporate the heating indicator, such as an LED light, incandescent light, neon bulb, flashing light, audible alarm, or any of various combinations thereof, that are electrically coupled to a portable power supply 3606 and/or a power supply (not illustrated) in the controller 3604, and/or a processor, to indicate whether or not the heating apparatus is working.

The controller 3604 may further include a connector 3648 through which power is provided for the controller 3604. The connector 3648 may be a USB connector. The therapy belt 3600 may include a portable power source 3606 that is placed in a pocket 3608. The pocket 3608 may be attached to, formed within, sewed on, and/or affixed to the outer portion of the therapy belt 3600. A USB cable 3605 may connect the portable power source 3606 and the connector 3648, to provide power for the controller 3604, and/or the heating device, and/or the electrical stimulation device, from the portable power source 3606.

FIG. 42 is a view of the inner portion of the therapy belt 3600 of FIG. 41 according to one example of the present disclosure. The inner portion of the therapy belt 3400 (FIG. 42) illustrates the therapy belt 3400 along an inner circumference. The therapy belt 3600 may include a heating device that is placed in the interlayer of the therapy belt 3600. The heating apparatus may include at least two heaters 3601. The therapy electrodes 3602 may be insulated from the heaters 3601. The heaters 3601 may comprise resistance wires, graphene sheets, heating films, or any of various combinations thereof. In one example, the position of each respective heater of the heaters 3601 along the inner circumference of the therapy belt 3600 (FIG. 42) is arranged to at least partially overlap a corresponding therapy electrode of the at least two therapy electrodes 3602 along the outer circumference of the therapy belt 3600 (FIG. 41). The portable power source 3606 may provide power to the heaters 3601 (FIG. 42) by connecting the portable power source 3606 to the connector 3648 (FIG. 41). In some implementations, the heaters 3601 may be located in locations on the therapy belt 3600 that do not overlap any of the therapy electrodes 3602. In some examples, the heaters 3601 may be replaced with only one heater. In other implementations, the heaters 3601 may be powered with power received via one or more antennas or inductive loops. The antennas or inductive loops may be included in one or more of the therapy electrodes 3602. Alternatively or additionally, the one or more antennas may be located separately from the therapy electrodes 3602. When the heater or the heaters 3601 is heated via the power from the one or more antennas, the heater and the antenna may be connected via one or more conductive wires.

Figure 43:
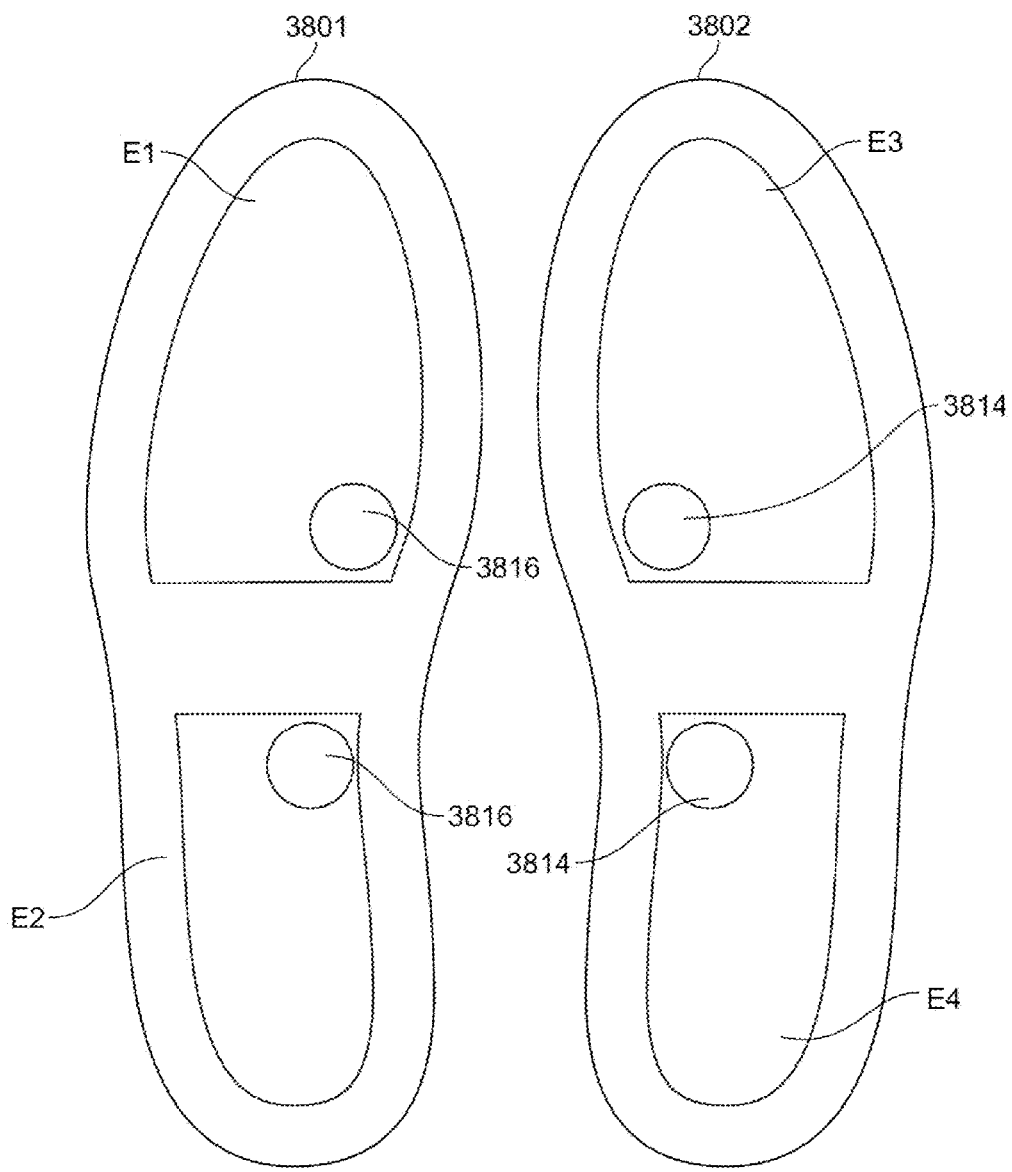
FIG. 43 is a top view of an insole according to one example of the present disclosure.

FIG. 43 illustrates the layout of one example of insoles for a pair of shoes. Foot shaped bases 3801, 3802 of insole material, such as plastic, rubber, polyurethane, foam, or the like, form the basis of the insoles. The bases 3801 and 3802 may alternatively be used in a pair of sandals or integrated into a pair of sandals. Likewise, the bases 3801 and 3802 may be used in any structure that is wearable on a foot of a human body as illustrated in FIG. 43, a first pair of stimulation electrodes E1 and E2 are placed on the base 3801. A second pair of stimulation electrodes E3 and E4 are placed on the base 3802. For purposes of illustration, the stimulation electrode E1 could be placed on an upper surface of the base 3801, with the stimulation electrode E2 being placed on a lower surface of the base 3801. Alternatively, the stimulation electrode E1 could be placed in a side-by-side arrangement with the stimulation electrode E2, where both of the stimulation electrodes E1 and E2 are placed on the upper surface of the base 3801. Regardless of the specific physical placement that is adopted for the stimulation electrodes E1 and E2, the first pair of stimulation electrodes E1 and E2 are insulated from each other.

For purposes of illustration, the stimulation electrode E3 can be placed on an upper surface of the base 3802, and the stimulation electrode E4 can be placed on a lower surface of the base 3802. Alternatively, the stimulation electrode E3 could be placed in a side-by-side arrangement with the stimulation electrode E4, where both of the stimulation electrodes E3 and E4 are placed on the upper surface of the base 3802. Regardless of the specific physical placement that is adopted for the stimulation electrodes, the second pair of stimulation electrodes E3 and E4 are insulated from each other.

In general, the first pair of stimulation electrodes E1 and E2 can be placed on any portion or surface of the base 3801, as long as the stimulation electrode E1 is insulated from the stimulation electrode E2. Likewise, the second pair of stimulation electrodes E3 and E4 can also be placed on any portion or surface of the base 3802, as long as the stimulation electrode E3 is insulated from the stimulation electrode E4. For example, the stimulation electrode E1 may be placed on the upper surface of the base 3801 and proximate to the left edge of the base 3801, while the simulation electrode E2 may be placed on the upper surface of the base 3801 and proximate to the right edge of the base 3801. Similarly, the stimulation electrode E3 may be placed on the upper surface of the base 3802 and proximate to the left edge of the base 3802, while the simulation electrode E4 may be placed on the upper surface of the base 3802 and proximate to the right edge of the base 3802. These examples are provided solely for purposes of illustration, as other placements are possible for the first pair of stimulation electrodes E1 and E2, as well as the second pair of stimulation electrodes E3 and E4.

At least one of the stimulation electrodes E1 or E2 is configured to be applied externally to the foot, underneath the foot, and in contact with the foot. In operation, the first pair of stimulation electrodes E1 and E2 are electromagnetically coupled to a set of muscle groups or nerve areas within a left foot that has been inserted above the base 3801. Likewise, at least one of the stimulation electrodes E3 or E4 is configured to be applied externally to the foot, underneath the foot, and in contact with the foot. In operation, the second pair of stimulation electrodes E3 and E4 are electromagnetically coupled to a set of muscle groups or nerve areas within a right foot that has been inserted above the base 3802.

Figure 44:
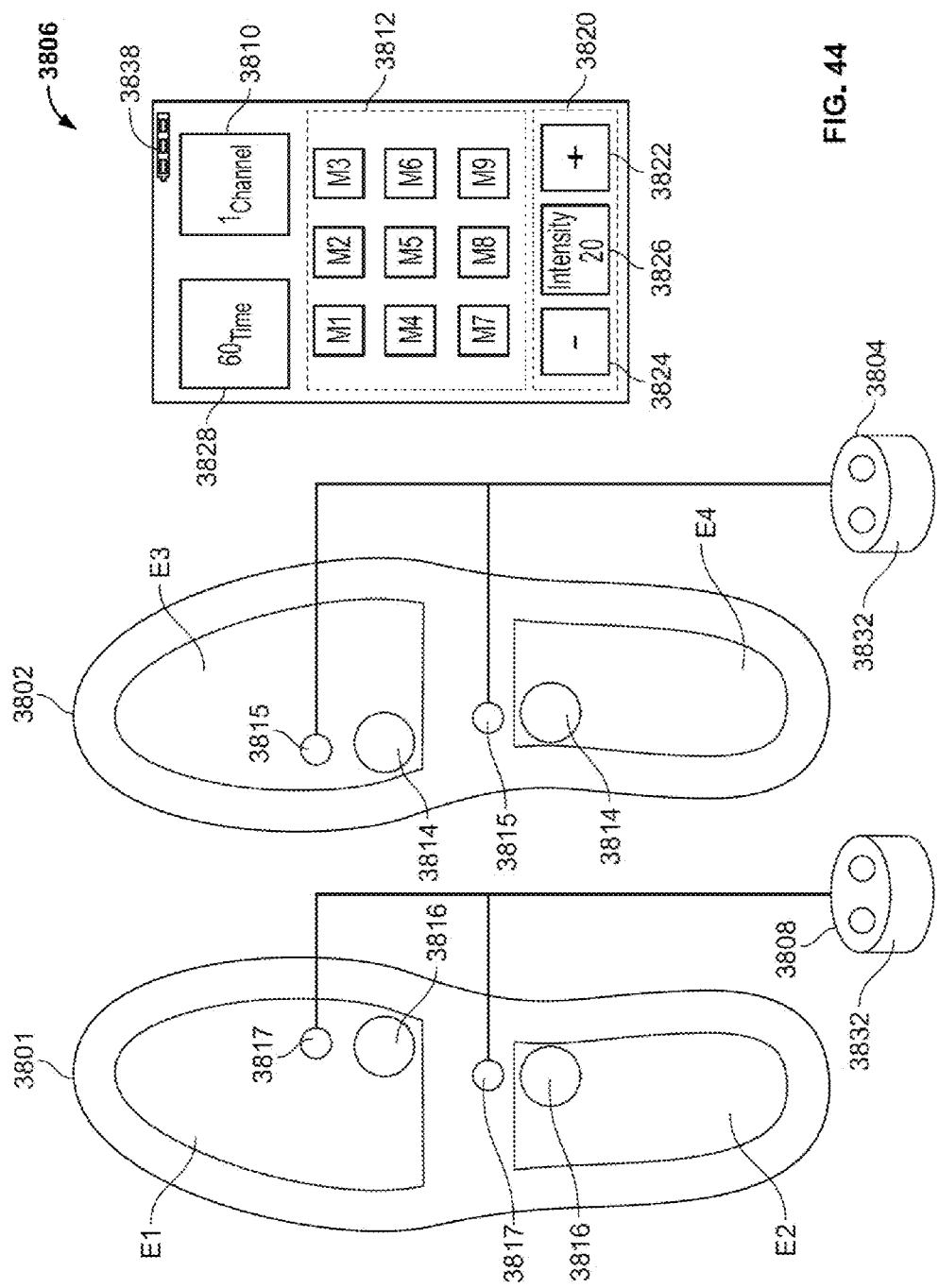
FIG. 44 is an electrical stimulation system according to one example of the present disclosure.

FIG. 44 shows an electrical stimulation system according to one example of the present disclosure. As shown in FIGS. 43 and 44, the base 3801 may have a pair of male metal snaps 3816. With reference to FIG. 44, the pair of male metal snaps 3816 is configured for attachment to a pair of female metal snaps 3817. The pair of male metal snaps 3816 are positioned on the upper surface of the base 3801, such that the pair of male metal snaps 3816 is in direct contact with, or proximate to, the foot. The pair of male metal snaps 3816 are configured for connecting with at least one electrical stimulation unit 3808 by attaching to the pair of female metal snaps 3817.

As shown in FIG. 44, the base 3802 may have a pair of male metal snaps 3814 configured for attachment to a pair of female metal snaps 3815. The pair of male metal snaps 3814 are on the upper surface of the base 3802, such that the pair of male metal snaps 3814 are placed is in direct contact with, or proximate to, the foot. The pair of male metal snaps 3814 are configured for connecting with at least one electrical stimulation unit 3804 by attaching to the pair of female metal snaps 3815.

The pairs of male metal snaps 3814 and 3816, as well as the pairs of female metal snaps 3815 and 3817, can alternatively be some other type or design of fastener for releasably engaging and electrically connecting the stimulation electrodes E1, E2, E3, and E4 to the electrical stimulation unit. The fastener is configured for removably attaching and electrically connecting with the electrical stimulation unit 3804, 3808, respectively, thereby forming an electronic circuit to apply an electrical stimulation pulse to tissue that is in electrical contact with the stimulation electrodes.

In some examples, the pairs of male metal snaps 3814 and 3816, and the pairs of female metal snaps 3815 and 3817, may not be necessary. While electrodes E1 and E2 are insulated from each other, electrodes E1 and E2 may separately conductively connect to the electrical stimulation unit 3808. Electrodes E3 and E4 on the base 3802 may connect to the electrical stimulation unit 3804. Electrodes E1, E2, E3 and E4 may each be made of conductive gels or conductive rubbers.

The electrical stimulation unit 3808 may control electrodes E1 and E2 to generate various electric signals to stimulate the muscles within the foot. Electrodes E3 and E4 may have a similar configuration as electrodes E1 and E2, respectively. Pursuant to such a configuration, the electric signals that stimulate the muscles within the foot may flow between electrodes E1 and E2, and similarly between electrodes E3 and E4. The electrical signals may be AC signals, radio frequency signals, DC signals, or the like. In operation, the first pair of stimulation electrodes E1 and E2 are electromagnetically coupled to a set of muscle groups or nerve areas within a left foot that has been inserted above the base 3801. Likewise, in operation, the second pair of stimulation electrodes E3 and E4 are electromagnetically coupled to a set of muscle groups or nerve areas within a right foot that has been inserted above the base 3802. Thus, the electric signals can be controlled to stimulate the muscles within the foot without flowing through other parts of the body.

When comparing the configurations of FIGS. 43 and 44 with an alternative configuration where a first electrode is placed on the base 3801 and a second electrode is placed on the base 3802, wherein the electric signals have to pass through the body to complete a circuit to stimulate the muscles within the two feet, the configurations disclosed in FIGS. 43 and 44 have clear advantages.

In implementation, the electrical stimulation unit 3808 may be placed proximate to the location of the first pair of electrodes E1 and E2. Likewise, the electrical stimulation unit 3804 may be placed i proximate to the location of the second pair of electrodes E3 and E4. For example, when the bases 3801 and 3802 are part of a pair of sandals, the electrical stimulation unit 3804 may be placed above the base 3802, and in an upper portion of the sandals, such that the electrical stimulation unit 3804 is positioned on top or above the foot. Likewise, the electrical stimulation unit 3808 may be placed above the base 3801, and in an upper portion of the sandals, such that the electrical stimulation unit 3808 is positioned on top or above the foot. Alternatively, the electrical stimulation units 3804 and 3808 may be placed on any part of the sandals that are insulated from the pairs of electrodes E3 and E4, and E1 and E2, respectively. As shown in FIG. 44, the electrical stimulation units 3808 and 3804 may each include a power indicator 3832 to indicate whether the respective electrical stimulation unit 3808 or 3804 is powered on.

Figure 45:
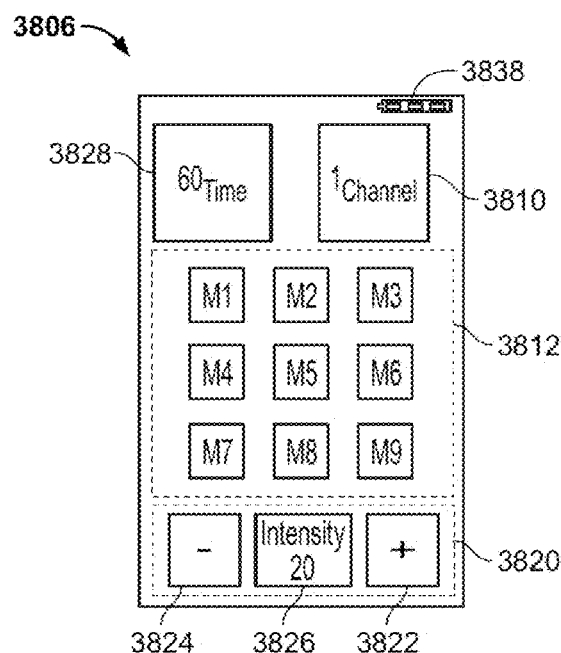
FIG. 45 is a view of a transmitter according to one example of the present disclosure.

As shown in FIGS. 44-45, a transmitter 3806 is a touch-screen controller that may remotely, wirelessly control each of the electrical stimulation units 3804, 3808 to deliver electrical pulses to foot tissue via the pairs of stimulation electrodes E1-E2 and E3-E4 that are connected to the electrical stimulation units 3808 and 3804, respectively. Although the transmitter 3806 is shown as a touch-screen controller, this is for purposes of illustration, as the transmitter 3806 could be implemented using momentary-contact buttons or switches. The number of electrical stimulation units 3804 and 3808 that the transmitter 3806 can control simultaneously may be limited. However, the transmitter 3806 may control any electrical stimulation unit 3804, 3808 after the transmitter 3806 and the electrical stimulation unit 3804, 3808 are paired. Therefore, the transmitter 3806 may control many electrical stimulation units. The transmitter 3806 may be a touch screen controller as shown in FIGS. 44-45. The transmitter 3806 may have different control buttons for a user to tap on to select an operating mode, an operating time period, one or more channels, an intensity level for the electrical stimulation, a massage strength for the electrical stimulation, a frequency for the electrical stimulation, and the like.

As shown in FIG. 45, the transmitter 3806 may include a channel selector 3810 for selecting one electrical stimulation unit 3804 or 3808 (FIG. 44) to control with the transmitter 3806, via a respective channel that is assigned to a corresponding electrical stimulation unit 3804, 3808. In one example, the channel selector 3810 (FIG. 45) is a control button on a touch screen that allows a user to select a channel to remotely, wirelessly transmit operating instructions to one of a plurality of wireless electrical stimulation units 3804 or 3808 (FIG. 44). The electrical stimulation unit 3804 or 3808 may function as a receiver for the transmitter 3806 to receive instructions from the transmitter 3806. However, the electrical stimulation unit 3804 or 3808 may mutually communicate with the transmitter 3806 to receive instructions and send feedback to the transmitter 3806.

The channel selector 3810 (FIG. 45) may have a number indicating which channel is selected, and such number may represent the corresponding electrical stimulation unit 3804 or 3808 that is selected. A user can select different wireless electrical stimulation units by pressing the channel selector 3810, which can cycle through all of the available channels. As indicated previously, each respective channel is associated with a corresponding electrical stimulation unit 3804 or 3808. The channel selector 3810 also can display a number indicating which of the electrical stimulation units has been selected, and/or a number that uniquely identifies the corresponding electrical stimulation unit. For example, as shown in FIG. 45, a number "1" displayed on the channel selector 3810 indicates a communication connection to a corresponding electrical stimulation unit that is identified as electrical stimulation unit number 1. Pressing the channel selector 3810 again changes the respective channel on which the transmitter 3806 operates, and thus changes the corresponding electrical stimulation unit that the transmitter 3806 controls, and changes the number displayed on the channel selector 3810.

At least one of the electrical stimulation units 3804, 3808 has at least two operating modes, each of which applies a time varying electrical signal or pulse to respective pairs of stimulation electrodes E3 and E4, or E1 and E2, in a different waveform or pattern. FIGS. 8-19 illustrate some exemplary waveforms for four exemplary operating modes.

The transmitter 3806 (FIG. 45) may include a mode selector 3812 for selecting an operating mode for each electrical stimulation unit 3804, 3808 (FIG. 44). The mode selector 3812 (FIG. 45) may comprise a plurality of mode selecting buttons M1-M9. Each of buttons M1-M9 may indicate one operating mode. In different operating modes, time-varying electrical signals or pulses of different waveforms may be applied to the stimulation electrodes. Pressing one of the touch screen mode selecting buttons M1-M9 may switch the transmitter 3806 to the operating mode corresponding to the selected button. The operating modes are not limited to nine modes corresponding to the buttons M1-M9.

At least some of the electrical stimulation units are capable of operating with least two intensities or signal levels. As shown in FIGS. 44-45, the transmitter 3806 includes an intensity selector 3820 for selecting different intensities. In the example shown in FIGS. 44-45, the intensity selector 3820 may include an increase button 3822 for increasing the operating intensity (i.e., signal level) for the electrical stimulation unit 3804 or 3808 to be controlled, and a decrease button 3824 for decreasing the operating intensity for the electrical stimulation unit 3804 or 3808 to be controlled.

The increase button 3822 and the decrease button 3824 may be remote control buttons on a touch screen that remotely, wirelessly transmit operating instructions of a user-selected intensity or signal level to a selected one of the plurality of wireless electrical stimulation units 3804 or 3808. The increase and decrease buttons 3822 and 3823 may have "+" and "−" signs respectively, to indicate their function to the user. A user can adjust the operating intensity by pressing the buttons 3822 and 3824 to a level that the user desires. The intensity may be denoted using an illustrative range 1 to 20 which represents a spectrum or range of different intensity levels.

As shown in FIGS. 44-45, the transmitter 3806 can further include a display 3826 for indicating the level of the operating intensity that has been selected. When the user presses either the increase button 3822 or the decrease button 3824, the display 3826 may show a number indicating the level of the intensity.

As shown in FIGS. 44-45, the transmitter 3806 may include a time selector 3828 for selecting an operating time period for at least some of the electrical stimulation units 3804 or 3808. The time selector 3828 may be a single remote control button on the touch screen that remotely, wirelessly transmits operating instructions of a user selected operating time period/duration to a selected electrical stimulation unit 3804 or 3808.

The time selector 3828 may include a display indicating the time or length of time that has been selected. The user can select different operating time periods by continuing to press the time selector 3828. When the user presses the time selector 3828, the number on the display changes and indicates the operating time (may be in minutes) being selected for a selected electrical stimulation unit 3804, 3808 to be activated for applying electrical stimulation to the user. In one example, when the user presses the time selector 3828 once, the number on the display changes in a 10-minute interval and the number of the time displayed may be in a range of 10 to 60 minutes.

Additionally, the transmitter 3806 and each electrical stimulation unit 3804, 3808 may include its own internal power supply (not shown). The internal power supply may be a rechargeable battery, or other suitable energy storage device. Each electrical stimulation unit 3804, 3808 may include a charging indicator 132 as shown in FIG. 21. The charging indicator 132 is on when the electrical stimulation units 3804, 3808 are charging, and turns off when the electrical stimulation units 3804, 3808 are either disconnected form the charging source, or are fully charged. As shown in FIG. 21, each electrical stimulation unit can be charged using a USB connector 134 connecting to an AC adapter 136. The USB connector 134 and the AC adapter 136 can also be used to charge a rechargeable battery in the transmitter 3806. The transmitter 3806 can include a battery display 138 that indicates the state of charge and/or charging status. In some implementations, the transmitter 3806 and the electrical stimulation units 3804 and 3808 may be charged remotely via one or more antennas or inductive loops. For example, an antenna may be placed inside the transmitter 3806 or the electrical stimulation unit 3804 or 3808, and the antenna may accept power remotely and provide the power supply to the transmitter 3806 and the electrical stimulation units 3804 and 3808.

The transmitter 3806 may wirelessly communicate with the electrical stimulation units 3804 and 3808 via an RF protocol, and for purposes of illustration, may be operating in the 2.4 GHz or 5 GHz band. For example, Bluetooth or Wifi technologies may be used. The transmitter 3806 may comprise antennas implementing a wireless communication protocol with the electrical stimulation units 3804 and 3808.

Figure 46:
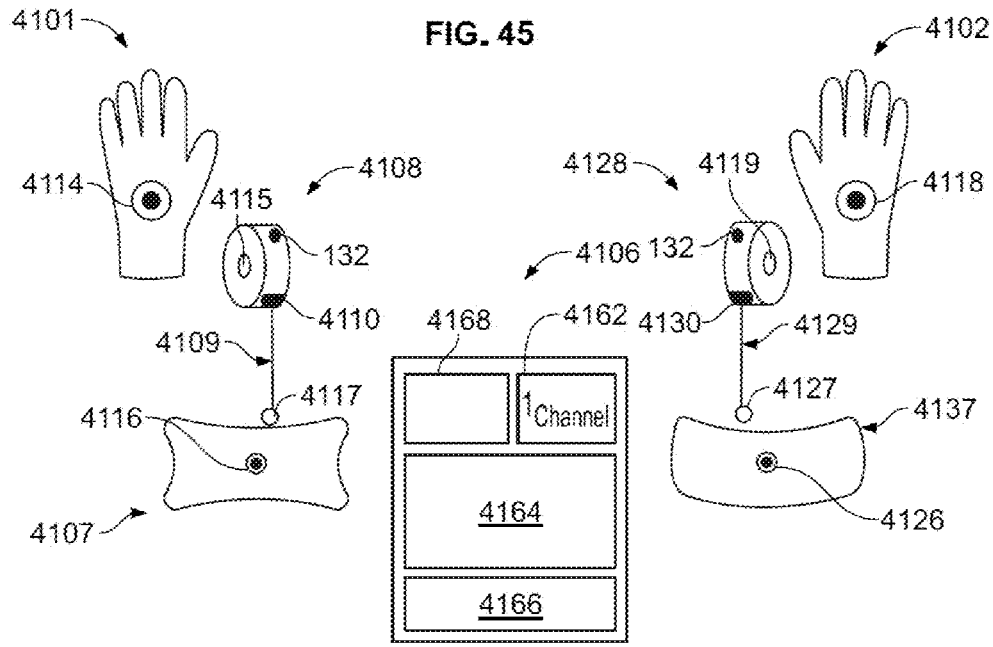
FIG. 46 is a view of a pair of gloves connecting with an electronic unit that is wirelessly controlled by a transmitter according to one example of the present disclosure.
Figure 47:
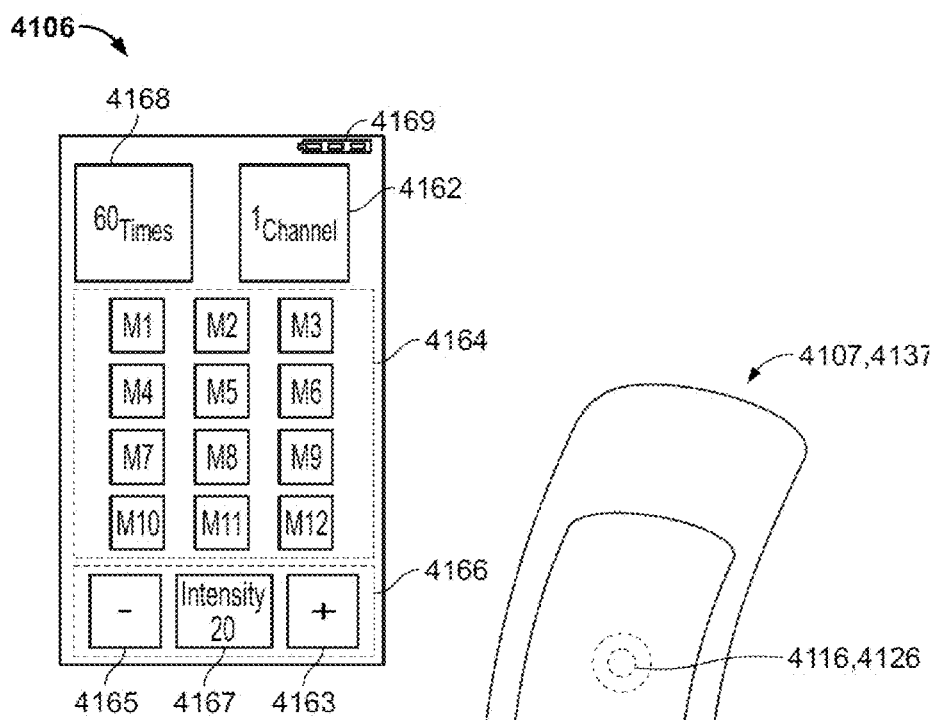
FIG. 47 is a detailed view of a transmitter according to one example of the present disclosure.

FIG. 46 is a view of a pair of gloves connecting with an electronic unit that is wirelessly controlled by a transmitter according to one example of the present disclosure. As shown in FIG. 46, a pair of gloves includes a first glove 4101 for a left hand, and a second glove 4102 for a right hand. The first glove 4101 and the second glove 4102 have similar functional configurations. The following description will mainly describe the first glove 4101 as a representative example.

Figure 49:
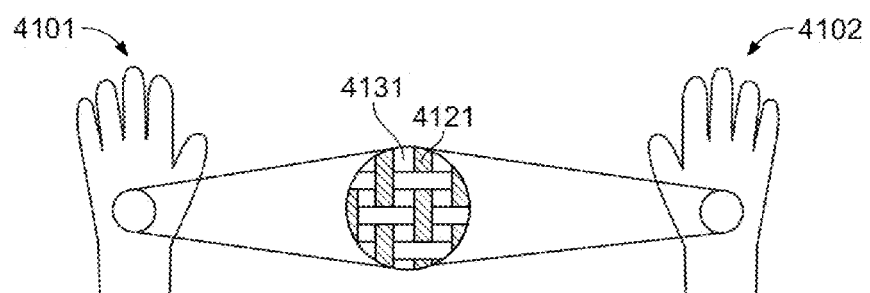
FIG. 49 is a detailed view of a glove including a conductive portion woven with an insulating portion according to one example of the present disclosure.

In one example shown in FIG. 49, the first glove 4101 may include at least one layer. The layer may include at least a conductive portion 4121, so that the layer of the first glove 4101 serves as one electrode. The conductive portion may be made of silver, copper, gold, aluminum, or another conductive material. When silver is used for the conductive portion, the conductivity for the glove is enhanced. In one example, the layer of the first glove 4101 may include silver threads woven with non-conductive threads, serving integratedly as one electrode.

As shown in FIG. 49, the first glove 4101 has a configuration in which an insulating portion 4131 is woven with the conductive portion 4121 of a predetermined thickness. The conductive portion 4121 is a member constituting the entire glove portion of the first glove 4101. The surface of the conductive portion 4121 enables contact with the surface of a person's hand. The conductive portion 4121 is connected to an electrical stimulation unit 4108 as shown in FIG. 46 by attaching conductive snaps as described later, thereby applying electrical pulses to hand tissue.

In one example, the first glove 4101 may further include a male metal snap 4114 for attaching to a female metal snap 4115 on the electrical stimulation unit 4108, as shown in FIG. 46. The male and female metal snaps 4114 and 4115 can alternatively be some other type or design of fastener for releasably engaging and electrically connecting the layer of the first glove 4101 to the electrical stimulation unit 4108.

In one example, the electrical stimulation unit 4108 is remotely and wirelessly controlled by a transmitter 4106, as illustrated in FIG. 46, to deliver time-varying electrical pulses to hand tissue via the layer of the first glove 4101 connected to the electrical stimulation unit 4108. The transmitter 4106 has the same function as the transmitter 3806 as illustrated in FIG. 45.

In one example, the electrical stimulation unit 4108 preferably includes a connector 4110 which may connect to an electrode pad 4107 via an electrode wire 4109. The electrode pad 4107 may have a male metal snap 4116 configured for attachment to a female metal snap 4117 of the electrode wire 4109. The metal snaps 4116, 4117 can alternatively be some other type or design of fastener for releasably engaging and electrically connecting the electrode pad 4107 to the electrical stimulation unit 4108.

The electrode pad 4107 may include a flexible substrate so that it can be easily applied on a surface of a human body, for example, arms, wrists, shoulders, neck, etc. Therefore, the fasteners, such as snaps, on the glove 4101 and the electrode pad 4107, with connection with the electrical stimulation unit 4108, form an electronic circuit to apply an electrical stimulation pulse to tissue in electrical contact with the electrodes. The electrode pad 4107 may be included in the glove 4101, or may be used separately.

In some implementations, a number of sensing points may be set on the electrode pad 4107. When the electrode pad 4107 is placed on a body surface, the electrical resistance between any two of the sensing points on the electrode pad 4107 may be measured by using the electrical stimulation unit 4108 when the electrical stimulation unit 4108 is electrically connected to the electrode pad 4107. The electrical resistance measured may be sent back to the transmitter 4106 via the electrical stimulation unit 4108 when the electrical stimulation unit 4108 is connected to the transmitter 4106. The measured electrical resistance between the number of sensing points may be used to determined that a spot of the body skin has an electrical resistance that is higher or lower than other spots on the body skin covered by the electrode pad 4107. The electric signals may be generated and may be directed for the spot that has the electrical resistance that is higher or lower than other spots on the covered body skin. Because two electrode pads may serve as two electrodes to form an electrical circuit to stimulate muscles covered the two electrode pads, the measurement of the electrical resistance may be conducted for two electrode pads together by measuring the electrical resistance between two of a number of sensing points on the body skin covered by the two electrode pads. The two electrode pads may be connected to one electrical stimulation unit 4108 that may be connected with the transmitter 4106. A sensor or the like may be placed on the electrode pad 4107 for each of the number of sensing points.

In some examples, the glove 4101 may include two electrodes. The two electrodes on the glove 4101 may be insulated from each other. Thus, the conductive portion 4121 for the glove 4101 may be divided into two portions that are insulated from each other. Alternatively, two electrode pads 4107 may be attached to the glove 4101. Each of the two portions may be electrically connected to the electrical stimulation unit 4108 or a controller which is remotely and wirelessly controlled by the transmitter 4106. The electrical stimulation unit 4108 (or a controller) may communicate with the transmitter 4106 and receive instructions and drive the two electrodes to create electric signals to stimulate muscles on a hand within the glove 4101. The electrical stimulation unit 4108 (or a controller) may also send information back to the transmitter 4106. When the glove 4101 comprises two portions that are insulated from each other, the electrically connected electrical stimulation unit 4108 (or the controller) may be placed on the glove 4101. The electrical stimulation unit 4108 (or the controller) may be placed anywhere on the glove 4101. The placement of the electrical stimulation unit 4108 or the controller may not change the fact that a first portion and a second portion of the glove 4101 are insulated from each other, even though any one of the first or second portions may include conductive materials.

Similarly, as shown in FIGS. 46 and 49, the second glove 4102 may include at least one layer. The layer may include at least a conductive portion 4121, so that the layer of the second glove 4102 serves as one electrode. The conductive portion may be made of silver, gold, copper, aluminum, or another conductive material. When silver is used for the conductive portion, the conductivity of the glove is enhanced. In one example, the layer of the second glove 4102 may include silver threads woven with non-conductive threads, and the resulting weave serving as one electrode. When the first glove 4101 is to serve as a first electrode, and the second glove 4102 is to serve as a second electrode, both the first glove 4101 and the second glove 4102 may connect to a single electrical stimulation unit 4108 (or to a controller). The electrical stimulation unit 4108 may receive instructions from the transmitter 4106 for driving the first and second electrodes to create electric signals to stimulate muscles on both hands. However, in this implementation, the electric signals that stimulate muscles on both hands may also pass through other part of the body, including the heart. However, pursuant to a further example, the first glove 4101 may be configured to provide two conductive portions that are insulated from each other. Likewise, the second glove 4102 may be configured to provide two conductive portions that are insulated from each other. Using two conductive portions is advantageous because the electric signals generated to stimulate muscles on one hand will not pass through any other part of the body such as the heart.

In one example, as shown in FIG. 49, the second glove 4102 may have a configuration in which an insulating portion 4131 may be woven with the conductive portion 4121, such that the resulting weave or layer has a predetermined thickness. The conductive portion 4121 may be a member constituting the entire glove portion of the second glove 4102 and is connected to an electrical stimulation unit 4128 by attaching snaps, thereby applying electrical stimulation pulses to hand tissue. The surface of the conductive portion 4121 enables contact with the surface of a person's hand.

In one example, the second glove 4102 may further include a male metal snap 4118 configured for attachment to a female metal snap 4119 on the electrical stimulation unit 4128, as shown in FIG. 46. The metal snaps 4118, 4119 can alternatively be some other type or design of fastener for releasably engaging and electrically connecting the layer of the second glove 4102 to the electrical stimulation unit 4128.

In one example, the electrical stimulation unit 4128 is remotely and wirelessly controlled by the transmitter 4106, as illustrated in FIG. 46, to deliver time-vary electrical waveforms or pulses to hand tissue via the layer of the second glove 4102 connected to the electrical stimulation unit 4128.

Figure 48:
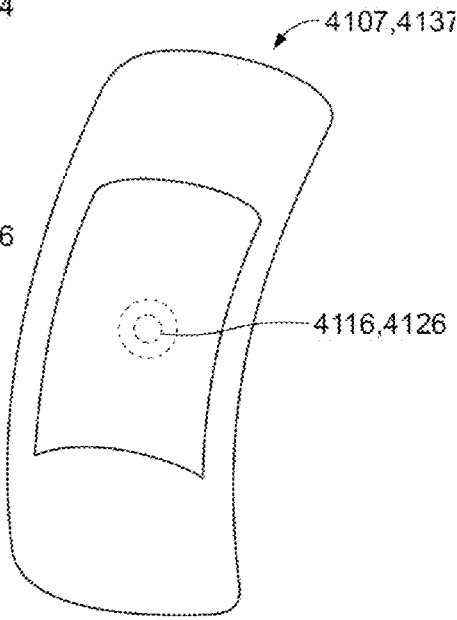
FIG. 48 is a view of an electrode pad configured for connecting with an electrical stimulation unit according to one example of the present disclosure.

In one example, the electrical stimulation unit 4128 may include a connector 4130 which may connect to an electrode pad 4137 via an electrode wire 4129. With reference to FIGS. 46 and 48, the electrode pad 4137 may have a male metal snap 4126 configured for attachment to a female metal snap 4127 of the electrode wire 4129. The metal snaps 4126, 4127 can alternatively be some other type or design of fastener for releasably engaging and electrically connecting the electrode pad 4137 to the electrical stimulation unit 4128.

The electrode pad 4137 may include a flexible substrate so that it can be easily applied on a body surface, for example, arms, wrists, shoulders, neck, etc. Therefore, the fasteners, such as snaps, on the glove second 4102 and the electrode pad 4137, with connection to the electrical stimulation unit 4128, form an electronic circuit to apply an electrical stimulation pulse to tissue in electrical contact or in electromagnetic coupling with the electrodes.

As shown in FIG. 46, the transmitter 4106 may remotely, wirelessly control each of the electrical stimulation units 4108, 4128 to deliver time-vary electrical pulses to tissue via the stimulation electrodes connected with the electrical stimulation units 4108, 4128. The transmitter 4106 can be a remote controller as shown in FIG. 45. Illustratively, the transmitter 4106 can be implemented using a touch-screen controller, or a controller that uses momentary-contact switches or buttons. The transmitter 4106 can have different control buttons for a user to tap on to select an operating mode, an operating time period, a channel, an intensity or signal level, massage strength for the electrical stimulation, and frequency of the electrical stimulation.

Additionally, the transmitter 4106 and each electrical stimulation unit 4108, 4128 may include its own internal power supply (not shown). The internal power supply may be a rechargeable battery, or other suitable energy storage device. The transmitter 4106 and each electrical stimulation unit 4108, 4128 may also be charged wirelessly via a built-in antenna or inductive loop to accept power wirelessly. Each electrical stimulation unit may include a charging indicator 132 as shown in FIG. 46. The charging indicator 132 is on when the respective electrical stimulation unit 4108 or 4128 is charging. The charging indicator 132 turns off when the respective electrical stimulation unit 4108 or 4128 is either disconnected form the charging source or is fully charged. Each electrical stimulation unit 4108 or 4128 may be charged using a USB connector connecting to an AC adapter. The USB connector and the AC adapter can also be used to charge a rechargeable battery in the transmitter 4106. The transmitter 4106 may include a battery display indicating the state of charge and/or charging status.

The transmitter 4106 wirelessly communicates with the electrical stimulation units 4108 and 4128 via RF protocol which, for illustrative purposes, may be operating in the 2.4 GHz or 5 GHz band. For example, Bluetooth or WIFI technologies may be used. The transmitter 4106 may comprise antennas implementing a wireless communication protocol with the electrical stimulation units.

Figure 50:
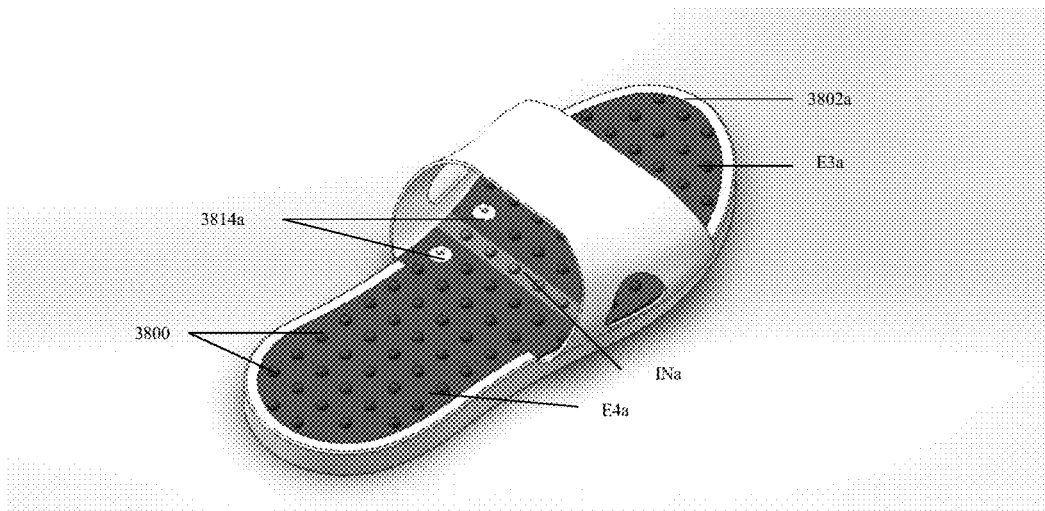
FIG. 50 is a top view of a sandal according to one example of the present disclosure.

FIG. 50 is a top view of a sandal according one example of the present disclosure. The sandal, as illustrated in FIG. 50, comprises an insole being integrated in the sandal and in direct contact of foot. The insole comprises a foot shaped base 3802a. A pair of stimulation electrodes E3a and E4a are placed on the base 3802a. E3a and E4a are made of conductive materials and E3a and E4a are insulated from each other. An insulation area INa, as illustrated in FIG. 50, divides the base 3802a into two parts—the upper part and the lower part. The upper part may correspond to E3a and the lower part may correspond to E4a. The insulation area INa insulates E3a from E4a.

As shown in FIG. 50, the base 3802a may have a pair of male metal snaps 3814a that may be configured for attachment to a pair of female metal snaps 3815 (as shown in FIG. 44). The pair of male metal snaps 3814a are on the upper surface of the base 3802a, such that the pair of male metal snaps 3814a are placed is in direct contact with, or proximate to, the foot. One male metal snap 3814a may be placed on the stimulation electrode E3a while the other male metal snap 3814a may be placed on the stimulation electrode E4a. The pair of male metal snaps 3814a are configured for connecting with at least one electrical stimulation unit 3804 (as shown in FIG. 44) by attaching to the pair of female metal snaps 3815 (as shown in FIG. 44).

As shown in FIG. 50, a plurality of electrode protuberances 3800 may be integrally formed with the base 3802a. The electrode protuberances 3800 may be distributed over the upper surface of the base 3802a in a way that corresponds to the way in which acupoints are distributed in a human sole. As most people's soles are not entirely flat but are concavely curved on the inner side (where the arch is), the electrode protuberances 3800 may vary in height so that when a user's sole stamps on the surface of the base 3802a, the tips of the electrode protuberances 3800 are pressed against the corresponding acupoints in the user's sole. The pair of male metal snaps 3814a may be placed on the upper surface of the base 3802a corresponding in position to the arch.

Figure 51:
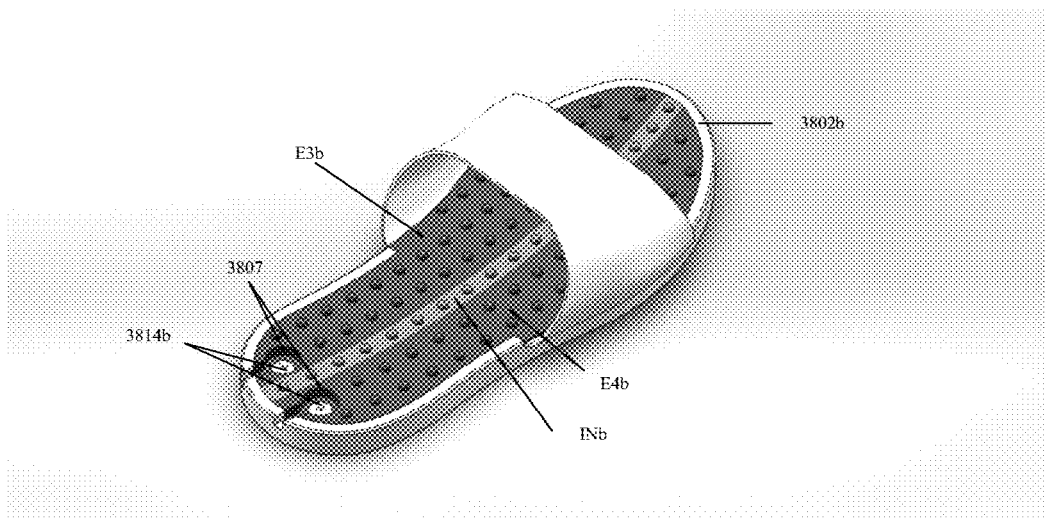
FIG. 51 is a top view of a sandal according to one example of the present disclosure.

FIG. 51 is a top view of a sandal according one example of the present disclosure. The sandal, as illustrated in FIG. 51, comprises an insole being integrated in the sandal and in direct contact of foot. The insole comprises a foot shaped base 3802b. A plurality of electrode protuberances may be integrally formed with the base 3802b. A pair of stimulation electrodes E3b and E4b are placed on the base 3802b. E3b and E4b are made of conductive materials and E3b and E4b are insulated from each other. An insulation area INb, as illustrated in FIG. 51, divides the base 3802b into two parts—the left part and the right part. The left part may correspond to E3b and the second part may correspond to E4b. The insulation area INb insulates E3b from E4b.

As shown in FIG. 51, the base 3802b may have a pair of male metal snaps 3814b that may be configured for attachment to a pair of female metal snaps 3815 (as shown in FIG. 44). One male metal snap 3814b may be placed on the stimulation electrode E3b while the other male metal snap 3814b may be placed on the stimulation electrode E4b. Each of the pair of male metal snaps 3814b may be placed in a groove 3807. The two grooves 3807 are concaved at the heel portion of the base 3802b. The grooves 3807 may be of the shape of the male metal snaps 3814b so as to accommodate the pair of male metal snaps 3814b. Additionally, the grooves 3807 may extend until the heel edge so as to accommodate the cables that connect the pair of male metal snaps 3814b with the electrical stimulation unit 3804 (as shown in FIG. 44) by attaching the pair of male metal snaps 3814b with the pair of female metal snaps 3815 (as shown in FIG. 44).

Figure 52:
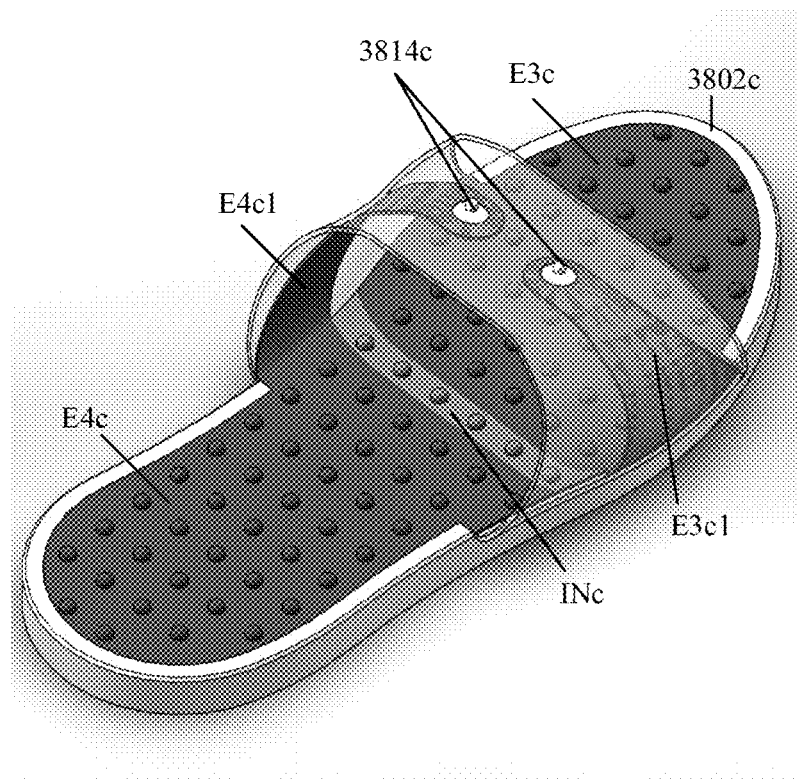
FIG. 52 is a top view of a sandal according to one example of the present disclosure.

FIG. 52 is a top view of a sandal according to one example of the present disclosure. The sandal, as illustrated in FIG. 52, comprises an insole being integrated in the sandal and in direct contact of foot. The insole comprises a foot shaped base 3802c. A plurality of electrode protuberances may be integrally formed with the base 3802c. An insulation area INc, as illustrated in FIG. 52, divides the base 3802c into two parts—the upper part and the lower part. The two parts may separately correspond to stimulation electrodes E3c and E4c. The pair of stimulation electrodes E3c and E4c are placed on the base 3802c. E3b and E4b are made of conductive materials and E3a and E4a are insulated from each other. As shown in FIG. 52, the stimulation electrode E3c comprises an extension portion E3cl extending along an upper strap of the sandal. And the stimulation electrode E4c comprises an extension portion E4cl extending along the upper strap of the sandal.

Figure 54:
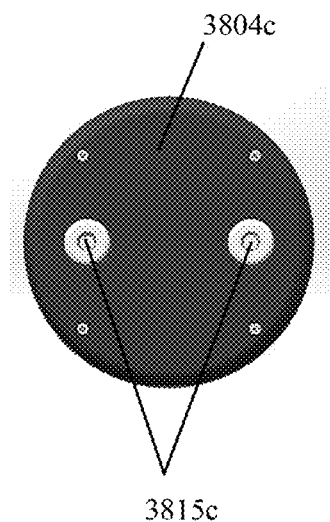
FIG. 54 is a rear view of the electrical stimulation unit of FIG. 53.

As shown in FIG. 52, the base 3802c may have a pair of male metal snaps 3814c that may be configured for attachment to a pair of female metal snaps 3815c (as shown in FIG. 54). The pair of male metal snaps 3814c may be placed on the upper strap of the sandal. And the pair of male metal snaps 3814c may face outside that is away from the foot.

One of the pair of male metal snaps 3814c is placed on the extension portion E3cl while the other metal snap 3814c is placed on the extension portion E4cl.

Figure 53:
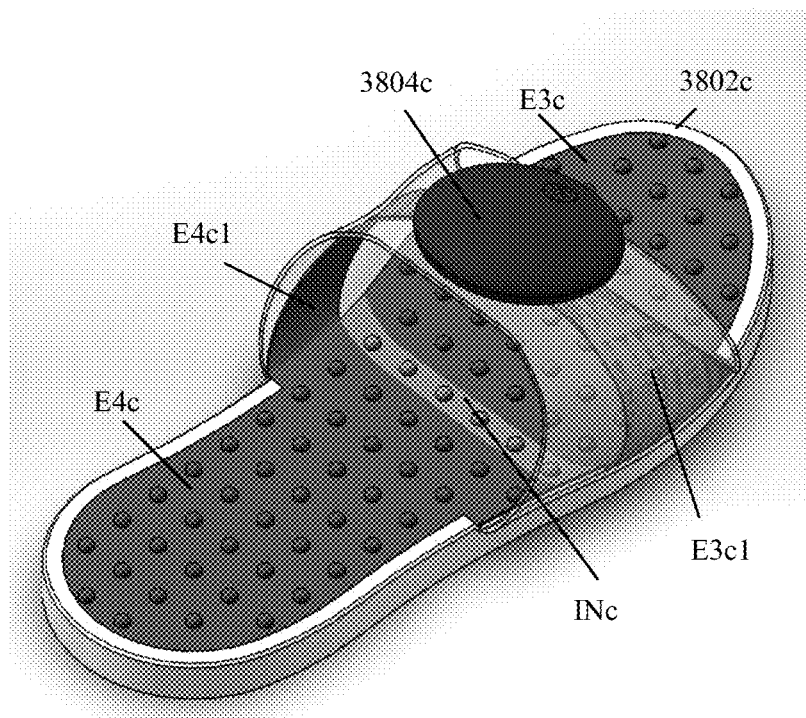
FIG. 53 is a top view of the sandal of FIG. 52 connected with an electrical stimulation unit.

As shown in FIG. 53, the pair of male metal snaps 3814c are connected with an electrical stimulation unit 3804c by attaching to the pair of female metal snaps 3815c (as shown in FIG. 54), thereby forming an electronic circuit to apply an electrical stimulation pulse to tissue that is in electrical contact with the stimulation electrodes E3c and E4c. The electrical stimulation unit 3804c may communicate with a transmitter, for example, the transmitter 3806 as shown in FIG. 44, wirelessly or with cable.

Figure 55:
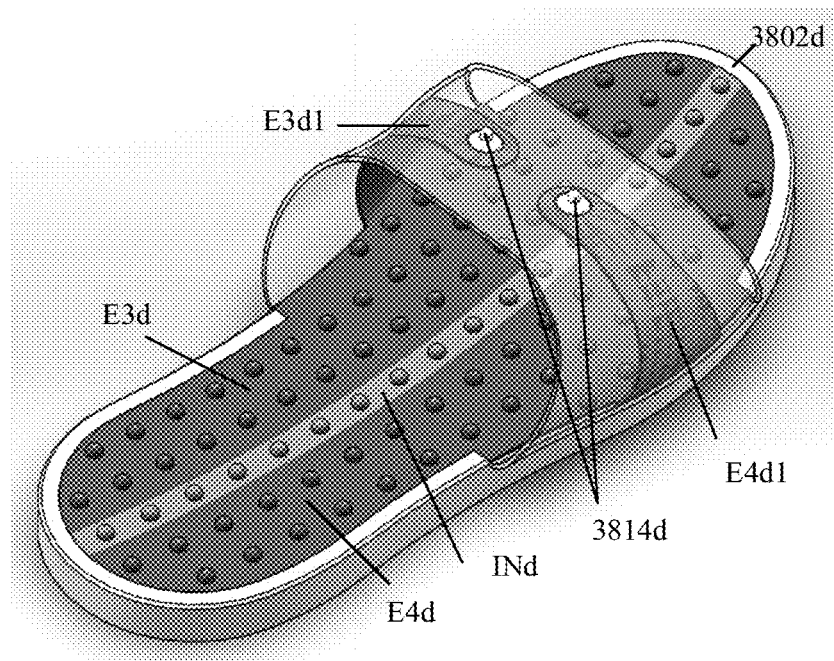
FIG. 55 is a top view of a sandal according to one example of the present disclosure.

FIG. 55 is a top view of a sandal according to one example of the present disclosure. The sandal, as illustrated in FIG. 55, comprises an insole being integrated in the sandal and in direct contact of foot. The insole comprises a foot shaped base 3802d. A plurality of electrode protuberances may be integrally formed with the base 3802d. An insulation area INd, as illustrated in FIG. 55, divides the base 3802d into two parts—the left part and the right part. The left part may correspond to the stimulation electrode E3d, and the right part may correspond to the stimulation electrode E4d. The pair of stimulation electrodes E3d and E4d are placed on the base 3802d. E3d and E4d are made of conductive materials and E3d and E4d are insulated from each other. As shown in FIG. 55, the stimulation electrode E3d comprises an extension portion E3dl extending along an upper strap of the sandal. And the stimulation electrode E4d comprises an extension portion E4dl extending along the upper strap of the sandal.

Figure 57:
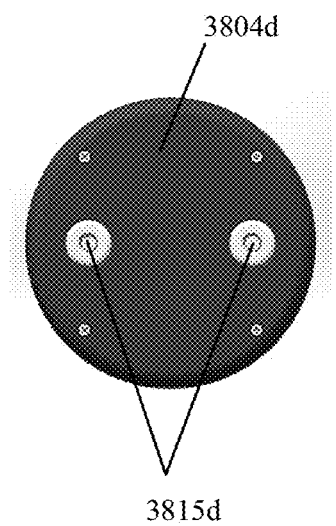
FIG. 57 is a rear view of the electrical stimulation unit of FIG. 56.

As shown in FIG. 55, the base 3802d may have a pair of male metal snaps 3814d that may be configured for attachment to a pair of female metal snaps 3815d (as shown in FIG. 57). The pair of male metal snaps 3814d may be placed on the upper strap of the sandal. And the pair of male metal snaps 3814d may face outside that is away from the foot. One of the pair of male metal snaps 3814d is placed on the extension portion E3dl while the other metal snap 3814d is placed on the extension portion E4dl.

Figure 56:
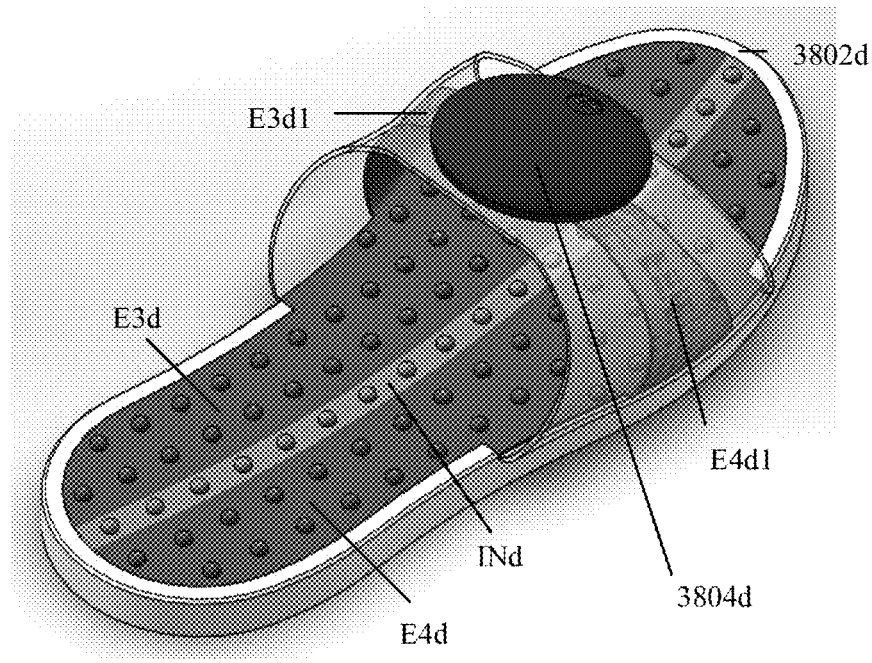
FIG. 56 is a top view of the sandal of FIG. 55 connected with an electrical stimulation unit.

As shown in FIG. 56, the pair of male metal snaps 3814d are connected with an electrical stimulation unit 3804d by attaching to the pair of female metal snaps 3815d (as shown in FIG. 57), thereby forming an electronic circuit to apply an electrical stimulation pulse to tissue that is in electrical contact with the stimulation electrodes E3d and E4d. The electrical stimulation unit 3804d may communicate with a transmitter, for example, the transmitter 3806 as shown in FIG. 44, wirelessly or with cable.

Figure 58:
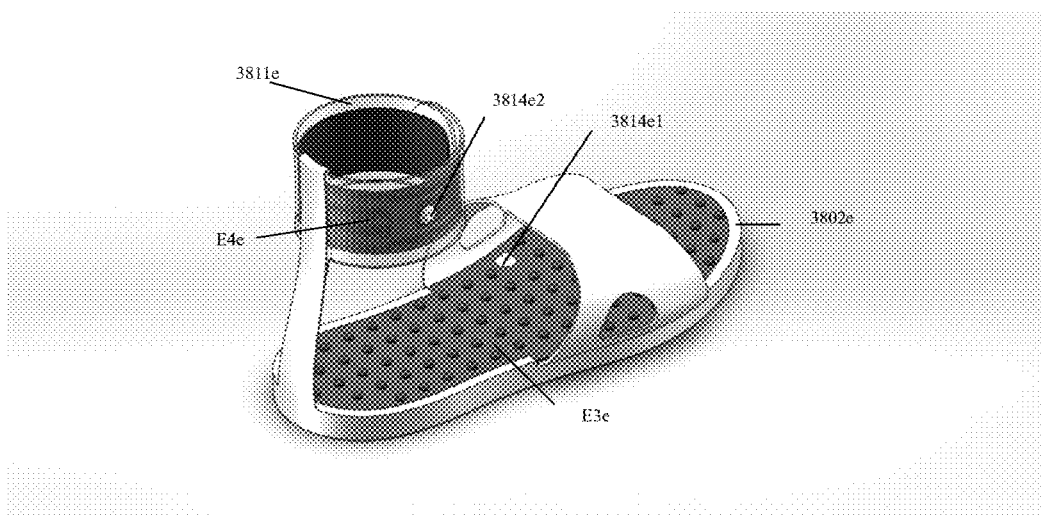
FIG. 58 is a top view of a sandal according to one example of the present disclosure.

FIG. 58 is a top view of a sandal according to one example of the present disclosure. The sandal, as illustrated in FIG. 58, comprises an insole being integrated in the sandal and in direct contact of foot. The insole comprises a foot shaped base 3802e. A plurality of electrode protuberances may be integrally formed with the base 3802e. The base 3802e comprises a stimulation electrode E3e that is made of conductive material. The sandal may also comprise an ankle strap 3811e. The inner portion of the ankle strap 3811e comprises a stimulation electrode E4e that is of a strap shape and in contact of a user's skin around ankle.

As shown in FIG. 58, a male metal snap 3814e1 is placed on the stimulation electrode E3e and may be configured for attachment to a female metal snaps 3815 (as shown in FIG. 44). And another male metal snap 3814e2 is placed on the stimulation electrode E4e, and the male metal snap 3814e2 faces outside that is away from the user's ankle. The male metal snaps 3814e1 and 3814e2 are configured for connecting with at least one electrical stimulation unit 3804 (as shown in FIG. 44) by attaching to the pair of female metal snaps 3815 (as shown in FIG. 44).

The present disclosure provides an electrical stimulation system for providing electrical stimulation to a subject's body. The system include a wireless controller; an electrical stimulation unit generating electrical stimulation signals, responsive to the wireless controller; at least two electrodes adapted to be disposed in electrical contact with the subject's body spaced apart from the electrical stimulation unit and from each other; and a cable electrically connecting the electrical stimulation unit to the at least two electrodes to apply electrical stimulation signals from the electrical stimulation unit to the electrodes positioned remotely from the electrical stimulation unit.

The system may also include a substrate adapted to be applied to a body surface, where the at least two electrodes may be carried on the substrate.

According to the system disclosed above, the substrate may be an article of clothing to be worn by the subject, and the article of clothing may be a sock.

According to the system, the cable may be a Y-cable that includes a stem and two branches, with a plug disposed on the end of the stem, and a connector disposed on each of the branches, the plug being configured to couple with a socket on the electrical stimulation unit and each of the connectors being configured for attaching to, and electrically connecting to an electrode.

According to the system, the connectors may be configured for permanently attaching to the electrodes.

According to the system, each of the connectors may include a metal fastener configured for removably attaching with corresponding structures configured on the at least two electrodes.

According to the system, the cable may be an X-cable that include first and second input branches, and first and second output branches, connectors on each of the input branches adapted to be connected to the electrical stimulation unit, and connectors on each of the output branches adapted to connected to an electrode.

According to the system, the connectors on the input branches of the X-cable may be configured for permanently attaching with the electrical stimulation unit.

According to the system the connectors on the input branches of the X-cable may include metal fasteners configured for removably coupling with corresponding structures of the electrical stimulation unit.

According to the system, the connectors on the output branches of the X-cable may be configured for permanently attaching with an electrode.

According to the system, the connectors on the output branches of the X-cable may include metal fasteners configured for removably coupling with corresponding structures on the electrodes.

The present disclosure may also provide a method for controlling a plurality of electrodes disposed in electrical contact with a subject's body. The method may include remotely, wirelessly transmitting operation instructions to an electrical stimulation unit from a remote controller; providing electrical stimulation signals via the electrical stimulation unit in response to the operating instructions; transmitting the electrical stimulation signals from the electrical stimulation unit to the plurality of electrodes positioned remotely from the electrical stimulation unit that is electrically connected with the electrodes using a cable; and applying the electrical stimulation signals on the subject's body in electrical contact with the plurality of electrodes.

According to the method, the electrical stimulation unit may be electrically connected to the plurality of electrodes using a Y-cable or an X-cable.

According to the method, the electrical stimulation unit may be electrically connected to the plurality of electrodes using an X-cable.

According to the method, the operation instructions may be wirelessly transmitted to at least two electrical stimulation units from the remote controller on separate channels at different frequencies.

The present disclosure also provides a wireless electrical stimulation system. The system may include: at least two electrical stimulation units, each electrical stimulation unit having electrodes connected to the electrical stimulation unit; and a wireless controller for remotely, wirelessly controlling each of the electrical stimulation units by transmitting operating instructions to each of the electrical stimulation units on separate channels at different frequencies using a single remote control before sending instructions to selectively apply a time-varying electric potential to the electrodes to provide an electrical stimulation to tissue in electrical contact with the electrodes.

The system may further include a cable electrically connecting the electrical stimulation unit to the electrodes to apply electrical stimulation signals from the electrical stimulation unit to the electrodes positioned remotely from the electrical stimulation unit.

According to the system, the cable may be a Y-cable comprising a stem and two branches, with a plug disposed on the end of the stem, and a connector disposed on each of the branches, the plug being configured to couple with a socket on the electrical stimulation unit and each of the connectors being configured for attaching to, and electrically connecting to an electrode.

According to the system, the cable may be an X-cable that include first and second input branches, and first and second output branches, connectors on each of the input branches adapted to be connected to the electrical stimulation unit, and connectors on each of the output branches adapted to connected to an electrode.

In an example, the present disclosure provides a wireless controller for controlling an electrical stimulation device that is attachable on a surface of a body to provide electrical stimulation to the body.

Additionally, a wireless controller may be provided for controlling an electrical stimulation device that is attachable on a surface of a body to provide electrical stimulation to the body. The wireless controller may include a control circuit, a display circuit and a communication circuit.

The control circuit may select, via a user interface, one of a plurality of modes, one of a plurality of intensities and one of a plurality of channels; the display circuit may display, via the user interface, the selected mode, the selected intensity and the selected channel.

The communication circuit may send the selected mode, the selected intensity on the selected channel to the electrical stimulation device where the electrical stimulation device may include at least two electrodes insulated from each other that are adapted to be disposed on the body's surface and are in electrical contact with the body's surface, and electrical stimulation device may generate electrical stimulation signals to be output by the at least two electrodes in the selected mode with the selected intensity to provide the electrical stimulation to the body.

According to other examples, an electrical stimulation apparatus is provided. The electrical stimulation apparatus comprises an electrical stimulation unit configured to generate at least one electrical waveform. Two electrodes, operatively coupled to the electrical stimulation unit, are configured to receive the at least one electrical waveform from the electrical stimulation unit. The two electrodes are insulated from each other. The two electrodes are provided in a structure that is wearable on a foot of a human body. The structure is configured for providing electrical stimulation to the foot. A remote controller is configured for controlling the electrical stimulation unit by generating and transmitting one or more control signals, wherein the electrical stimulation unit includes a receiver configured for receiving the one or more control signals from the remote controller. In response to receiving the one or more control signals from the remote controller, the electrical stimulation unit generates the at least one electrical waveform and applies the at least one electrical waveform to the two electrodes. The two electrodes are configured to deliver the generated at least one electrical waveform to a set of muscle groups or nerve areas within the foot that are electromagnetically coupled to the two electrodes. At least one of the two electrodes is configured to be applied externally to the foot, underneath the foot, and in contact with the foot. The one or more control signals cause the electrical stimulation unit to apply an electric potential to the two electrodes to provide an electrical stimulation to the set of muscle groups or nerve areas within the foot that are electromagnetically coupled to the two electrodes.

According to the apparatus, the electrical pulses may be delivered to the muscle groups or nerve areas within the foot without going through any part of the human body other than the foot. The electrical pulses may be delivered to sets of muscle groups or nerve areas within the foot without going through a heart of the human body. This may be helpful because, if only one electrode is applied to each sandal of a pair of sandals, electrical current will flow along a path from one sandal to the other through the human body When two electrodes, one on each sandal, work together to apply signals to simulate the muscles within the two feet, the electrical pulses may go through other parts of the body, such as the heart, unnecessarily. Providing two electrodes on each sandal as disclosed herein can avoid delivery of electrical waveforms to other sensitive parts of the body such as the heart.

According to the apparatus, the two electrodes may be integrated with an insole of a sandal, such that the insole includes at least a first conductive area, and a second conductive area that is insulated from the first conductive area. A first electrode is connected to the first conductive area, and a second electrode is connected to the second conductive area. The electrical stimulation unit may be placed on an upper strap of the scandal. The insole may be substantially made of conductive rubber or conductive gel. The electrical stimulation unit may be releasably connected to two connectors that are provided on the upper strap of the sandal.

According to the apparatus, the structure that is wearable on the foot of the human body may be one of a pair of sandals.

The present disclosure also provides a wireless electrical stimulation system for providing electrical stimulation to a foot of a human body. The system includes an electrical stimulation unit configured to generate at least one electrical waveform. The system also includes two electrodes operatively coupled to the electrical stimulation unit and configured to receive the at least one electrical waveform from the electrical stimulation unit. The two electrodes are insulated from each other, and the two electrodes are provided in a structure that is wearable on the foot. The structure is configured for providing electrical stimulation to the foot. The system further includes a wireless remote controller configured for wirelessly controlling the electrical stimulation unit by generating and transmitting one or more wireless control signals, wherein the electrical stimulation unit includes a wireless receiver configured for wirelessly receiving the one or more control signals from the remote controller. In response to receiving the one or more wireless control signals from the remote controller, the electrical stimulation unit generates the at least one electrical waveform and applies the at least one electrical waveform to the two electrodes. The two electrodes are configured to deliver the generated at least one electrical waveform to a set of muscle groups or nerve areas within the foot that are electromagnetically coupled to the two electrodes. At least one of the two electrodes is configured to be applied externally to the foot, underneath the foot, and in contact with the foot. The one or more control signals cause the electrical stimulation unit to apply an electric potential to the two electrodes to provide an electrical stimulation to the set of muscle groups or nerve areas within the foot that are electromagnetically coupled to the two electrodes.

According to the system, the electrical stimulation unit may be capable of operating with at least two intensities or signal levels. The remote controller may have an intensity selector for selecting one of the at least two intensities of operation for the electrical stimulation unit. The intensity selector may include an increase control and a decrease control.

According to the system, a plurality of electrical stimulation units are provided. The remote controller may include a display for indicating which one of the plurality of electrical stimulation units has been selected. The remote controller may be a smart phone running an application.

The present disclosure provides a method of utilizing an electrical stimulation device. The method includes providing an electrical stimulation unit configured to generate at least one electrical waveform, and providing a structure that is wearable on a foot of a human body. The structure comprises a first electrode, a second electrode, and an insulating material that insulates the first electrode from the second electrode. The structure is configured for providing electrical stimulation to the foot. The method further includes applying the structure to the foot, and applying the generated at least one electrical waveform to the first and second electrodes using a remote controller configured for controlling the electrical stimulation unit by generating and transmitting one or more control signals. The electrical stimulation unit includes a receiver configured for receiving the one or more control signals from the remote controller. The generated at least one electrical waveform is applied by delivering the electrical waveform to a set of muscle groups or nerve areas within the foot that are electromagnetically coupled to the first and second electrodes. At least one of the first and second electrodes is configured to be applied externally to the foot, underneath the foot, and in contact with the foot. The one or more control signals cause the electrical stimulation unit to apply an electric potential across the first electrode and the second electrode to provide an electrical stimulation to the set of muscle groups or nerve areas within the foot.

According to the method, delivering electrical pulses may include delivering electrical pulses to the set of muscle groups or nerve areas within the foot without traveling through any part of the human body other than the foot.

The method may also include integrating the electrical stimulation unit with an insole of a sandal, wherein the electrical stimulation unit is placed on an upper strap of the sandal.

The method may also include separating the insole into at least a first conductive area that is insulated from a second conductive area, connecting the first electrode to the first conductive area, and connecting the second electrode to the second conductive area. The method may also include providing a first connector and a second connector for the upper strap; connecting the first connector to the first conductive area, and connecting the second connector to the second conductive area. The method may also include releasably connecting the transmitter receiver to the first and second connectors of the upper strap of the sandal.

The present disclosure provides an electrical stimulation device for providing electrical stimulation that may include an electrical stimulation unit, a local controller and a heating apparatus.

The electrical simulation unit may have at least two electrodes that are insulated from each other, where the at least two electrodes may be placed on a body surface and may be configured to deliver electrical pulses to muscle groups or nerve areas within the body surface to which the electrodes are applied, where the electrodes may be configured to be applied externally to the body surface.

The local controller of the electrical simulation device may be communicated with a remote controller and may control the electrical stimulation unit by receiving operating instructions remotely and wirelessly from the remote controller, where the operating instructions may correspond to a selected one of a plurality of operating modes to the electrical stimulation unit on a channel, and based on the selected mode, the operating instructions may selectively apply an electric potential to the electrodes to provide an electrical stimulation to the muscle groups or the nerve areas within the body surface that is in electrical contact with the electrodes.

The heating apparatus of the electrical simulation device may be controllable by the local controller and generates heat and may provide the generated heat to the body surface via one or more heating pads that are applied on the proximity of the body surface where the electrodes are applied.

According to the device, the electrical stimulation device may have a substantial belt shape and is capable of adjustably placing around a waist of a human body. The heating apparatus may include a rechargeable battery that is electronically connected to the heating pads and the rechargeable battery enables the heating apparatus to generate the heat. The device may also include a display that shows at least one of: a heat level of the heat generated or a power level of the rechargeable battery.

According to the device, the heating apparatus may include an antenna that is configured to receive power wirelessly to generate the heat. The antenna may receive the power wirelessly via a radio frequency (RF) protocol.

According to the device, the heating apparatus may include both an antenna and a rechargeable, and a heat control switch attached to the electrical stimulation device may be configured to control the heat to be generated by either using the antenna to receive power wirelessly or using the rechargeable battery. The device may also include a functional control switch to control both the local controller and the heating apparatus. The heating apparatus may be controlled to generate the heat at a same time when the local controller is controlled to provide the electrical stimulation.

The heating apparatus may be controlled to generate the heat at a different time from when the local controller is controlled to provide the electrical stimulation.

The present disclosure provides a wireless electrical stimulation system for providing electrical stimulation. The system may include an electrical stimulation unit, a local controller, a remote controller and a heating apparatus.

The electrical simulation unit may have at least two electrodes that are insulated from each other, where the at least two electrodes may be placed on a body surface and may be configured to deliver electrical pulses to muscle groups or nerve areas within the body surface to which the electrodes are applied, where the electrodes may be configured to be applied externally with respect to the body surface.

The local controller of the electrical simulation device may be communicated with the remote controller and may control the electrical stimulation unit by receiving operating instructions remotely and wirelessly from the remote controller, where the operating instructions may correspond to a selected one of a plurality of operating modes to the electrical stimulation unit on a channel, and based on the selected mode, the operating instructions may selectively apply an electric potential to the electrodes to provide an electrical stimulation to the muscle groups or the nerve areas within the body surface that is in electrical contact with the electrodes.

The heating apparatus of the electrical simulation device may be controllable by the local controller and may generate heat and may provide the generated heat to the body surface via one or more heating pads that are applied on the proximity of the body surface where the electrodes are applied.

According to the system, each electrical stimulation unit may be capable of operating at at least two intensities, and where the remote controller may have an intensity selector for selecting one of the at least two intensities of operation for each electrical stimulation unit. The intensity selector may include an increase control and a decrease control.

According to the system, the remote controller may include a display for indicating which of the electrical stimulation units has been selected. The remote controller may be a smart phone running an application.

The present disclosure provides a method of utilizing an electrical stimulation device for providing electrical stimulation. The method may include providing an electrical stimulation unit, a local controller and a heating apparatus; insulating at least two electrodes of the electrical simulation unit from each other, and placing the at least two electrodes on a body surface; delivering electrical pulses to muscle groups or nerve areas within the body surface to which the electrodes are applied, where the electrodes may be configured to be applied externally with respect to the body surface.

The method may also include communicating, via the local controller of the electrical simulation device, with a remote controller and controls the electrical stimulation unit by receiving operating instructions remotely and wirelessly from the remote controller, where the operating instructions may correspond to a selected one of a plurality of operating modes to the electrical stimulation unit on a channel, and based on the selected mode, the operating instructions may selectively apply an electric potential to the electrodes to provide an electrical stimulation to the muscle groups or the nerve areas within the body surface that is in electrical contact with the electrodes.

The method may include controlling, via the local controller, the heating apparatus of the electrical simulation device to generate heat and provide the generated heat to the body surface via one or more heating pads that are applied on the proximity of the body surface where the electrodes are applied.

The method may also include providing a rechargeable battery for the heating apparatus; electronically connecting the rechargeable battery to the heating pads; and enabling the heating apparatus to generate the heat using the rechargeable battery. The method may include providing a display for the heating apparatus; and using the display to show at least one of: a heat level of the heat generated or a power level of the rechargeable battery.

The method may include providing an antenna for the heating apparatus; and receiving power wirelessly to generate the heat using the antenna. The method may also include providing an antenna and a rechargeable battery for the heating apparatus; attaching a heat control switch to the electrical stimulation device; and controlling, via the heat control switch to control the heat to be generated by either using the antenna to receive power wirelessly or using the rechargeable battery.

The controller may include a control circuit, a display circuit and a communication circuit. The control circuit may select, via a user interface, one of a plurality of modes, one of a plurality of intensities and one of a plurality of channels. The display circuit may display, via the user interface, the selected mode, the selected intensity and the selected channel. The communication circuit may send the selected mode, the selected intensity on the selected channel to the electrical stimulation device where the electrical stimulation device may include at least two electrodes insulated from each other that are adapted to be disposed on the body's surface and are in electrical contact with the body's surface, and electrical stimulation device may generate electrical stimulation signals to be output by the at least two electrodes in the selected mode with the selected intensity to provide the electrical stimulation to the body.

Examples are provided so that this disclosure will be thorough, and will fully convey the scope to those who are skilled in the art. Numerous specific details are set forth such as examples of specific components, devices, and methods, to provide a thorough understanding of examples of the present disclosure. It will be apparent to those skilled in the art that specific details need not be employed, that examples may be embodied in many different forms and that neither should be construed to limit the scope of the disclosure. In some examples, well-known processes, well-known device structures, and well-known technologies are not described in detail. In addition, advantages and improvements that may be achieved with one or more examples of the present disclosure are provided for purpose of illustration only and do not limit the scope of the present disclosure, as examples disclosed herein may provide all or none of the above mentioned advantages and improvements and still fall within the scope of the present disclosure.

Specific dimensions, specific materials, and/or specific shapes disclosed herein are examples in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The present disclosure may include dedicated hardware implementations such as application specific integrated circuits, programmable logic arrays and other hardware devices. The hardware implementations can be constructed to implement one or more of the methods described herein. Applications that may include the apparatus and systems of various examples can broadly include a variety of electronic and computing systems. One or more examples described herein may implement functions using two or more specific interconnected hardware modules or devices with related control and data signals that can be communicated between and through the modules, or as portions of an application-specific integrated circuit. Accordingly, the system disclosed may encompass software, firmware, and hardware implementations. The terms "module," "sub-module," "circuit," "sub-circuit," "circuitry," "sub-circuitry," "unit," or "sub-unit" may include memory (shared, dedicated, or group) that stores code or instructions that can be executed by one or more processors. The module refers herein may include one or more circuit with or without stored code or instructions. The module or circuit may include one or more components that are connected.

The terminology used herein is for the purpose of describing particular examples only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally," "about," and "substantially," may be used herein to mean within manufacturing tolerances. Or for example, the term "about" as used herein when modifying a quantity of an ingredient or reactant of the invention or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the examples.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the examples has been provided for purposes of illustration and description. It is not intended to be exhaustive or to limit the disclosure. Individual elements or features of a particular example are generally not limited to that particular example, but, where applicable, are interchangeable and can be used in a selected example, even if not specifically shown or described. The same may also be varied in many ways. Such variations are not to be regarded as a departure from the disclosure, and all such modifications are intended to be included within the scope of the disclosure.

What is claimed is:

1. A wireless electrical stimulation system for providing electrical stimulation, the system comprising:
- an electrical stimulation unit configured to generate at least one electrical waveform,
- two electrodes operatively coupled to the electrical stimulation unit and configured to receive the at least one electrical waveform from the electrical stimulation unit, wherein the two electrodes are insulated from each other, wherein the two electrodes are configured to be placed on or in proximity to a surface of a human body, wherein the two electrodes are configured to deliver the at least one electrical waveform to muscle groups or nerve areas within the surface to which the electrodes are applied, and wherein the electrodes are configured to be applied externally to the surface;
- a wireless remote controller configured for controlling the electrical stimulation unit by generating and wirelessly transmitting a first set of one or more control signals, wherein the electrical stimulation unit includes a wireless receiver configured for receiving the first set of one or more control signals from the wireless remote controller and wherein, in response to receiving the first set of one or more control signals from the wireless remote controller, the electrical stimulation unit generates the at least one electrical waveform and applies the at least one electrical waveform to the two electrodes; and
- a heating device operatively coupled to the wireless receiver of the electrical stimulation unit, the heating device comprising one or more heating pads configured for generating heat in response to a second set of one or more control signals received from the wireless remote controller, and further configured for providing the generated heat to the surface proximate to where the electrodes are applied;
- wherein the electrical stimulation unit comprises a flexible substrate configured to be directly in contact with the surface, wherein the wireless receiver is removably and directly connected to the flexible substrate, and the one or more heating pads are removably connected to the flexible substrate, wherein the wireless receiver comprises at least two button-shaped fasteners that are removably and directly connected to at least two button-shaped fasteners on the flexible substrate so that the wireless receiver is removably and directly connected to the flexible substrate, wherein the at least two button-shaped fasteners of the wireless receiver are located within an outer boundary of the wireless receiver;
- a belt, wherein the two electrodes are located in an interlayer of the belt, the interlayer is configured to be between an outer portion and an inner portion of the belt, wherein the one or more heating pads are located on the inner portion of the belt, and a position of each electrode of the two electrodes on the outer portion at least partially overlaps a position of a respective heating pad of the one or more heating pads on the inner portion so that an overlapped part of each electrode of the two electrodes and the respective heating pad provides heat to the surface so as to improve the therapeutic effect of the at least one electrical waveform delivered by the two electrodes;
- wherein the wireless remote controller is further configured for controlling the heating device by generating and transmitting a second set of one or more control signals, wherein the electrical stimulation unit includes the wireless receiver configured for wirelessly receiving the second set of one or more control signals from the wireless remote controller; and wherein, in response to receiving the second set of one or more control signals from the wireless remote controller, the electrical stimulation unit activates the heating device to generate heat and to provide the generated heat to the surface proximate to where the electrodes are applied.

2. The wireless electrical stimulation system of claim 1, wherein the electrical stimulation unit is configured for applying at least two different intensities or signal levels to the two electrodes, and wherein the wireless remote controller has an intensity selector for selecting one of the at least two different intensities or signal levels for the electrical stimulation unit.

3. The wireless electrical stimulation system of claim 2, wherein the intensity selector comprises an increase control and a decrease control.

4. The wireless electrical stimulation system of claim 1, wherein the electrical stimulation unit further comprises a plurality of electrical stimulation units, wherein the wireless remote controller further comprises a selector for selecting one of the plurality of electrical stimulation units, and a display for indicating which of the plurality of electrical stimulation units has been selected.

5. The wireless electrical stimulation system of claim 1, wherein the wireless remote controller is a smart phone running an application.

* * * * *